(12) United States Patent
Carpenter et al.

(10) Patent No.: US 7,041,438 B2
(45) Date of Patent: *May 9, 2006

(54) USE OF HUMAN EMBRYONIC STEM CELLS FOR DRUG SCREENING AND TOXICITY TESTING

(75) Inventors: Melissa K. Carpenter, London (CA); Margaret S. Inokuma, San Jose, CA (US); Chunhui Xu, Palo Alto, CA (US)

(73) Assignee: Geron Corporation, Menlo Park, CA (US)

( * ) Notice: Subject to any disclaimer, the term of this patent is extended or adjusted under 35 U.S.C. 154(b) by 333 days.

This patent is subject to a terminal disclaimer.

(21) Appl. No.: 10/039,956

(22) Filed: Oct. 23, 2001

(65) Prior Publication Data

US 2002/0137204 A1 Sep. 26, 2002

Related U.S. Application Data

(63) Continuation of application No. 09/859,291, filed on May 16, 2001, which is a continuation of application No. PCT/US01/01030, filed on Jan. 10, 2001, which is a continuation-in-part of application No. 09/688,031, filed on Oct. 10, 2000, now Pat. No. 6,667,176.

(60) Provisional application No. 60/175,581, filed on Jan. 11, 2000, provisional application No. 60/213,740, filed on Jun. 22, 2000, provisional application No. 60/213,739, filed on Jun. 22, 2000, provisional application No. 60/216,387, filed on Jul. 7, 2000, provisional application No. 60/220,064, filed on Jul. 21, 2000.

(51) Int. Cl.
*C12Q 3/00* (2006.01)
*C12Q 1/02* (2006.01)
*C12N 5/00* (2006.01)
*C12N 5/02* (2006.01)
*C12N 5/06* (2006.01)
*C12N 5/08* (2006.01)

(52) U.S. Cl. .............. 435/4; 435/29; 435/325; 435/363; 435/366; 435/374; 435/377; 435/383; 435/391

(58) Field of Classification Search ............... 435/325, 435/363, 366, 374, 404, 405, 4, 29, 377, 435/383, 394
See application file for complete search history.

(56) References Cited

U.S. PATENT DOCUMENTS

| | | | |
|---|---|---|---|
| 5,104,795 A | 4/1992 | Lee et al. | 435/69.1 |
| 5,166,065 A | 11/1992 | Williams et al. | 435/240.1 |
| 5,234,809 A | 8/1993 | Boom et al. | 435/91 |
| 5,332,672 A | 7/1994 | Conover et al. | 435/240.2 |
| 5,405,772 A | 4/1995 | Ponting | 435/240.31 |
| 5,453,357 A | 9/1995 | Hogan | 435/7.21 |
| 5,523,226 A | 6/1996 | Wheeler | 435/240.2 |
| 5,583,016 A | 12/1996 | Villeponteau et al. | 435/91.3 |
| 5,639,618 A | 6/1997 | Gay | 435/7.21 |
| 5,643,761 A | 7/1997 | Fisher et al. | 435/91.1 |
| 5,672,499 A | 9/1997 | Anderson et al. | 435/240.4 |
| 5,789,158 A | 8/1998 | Knowles et al. | 435/6 |
| 5,840,484 A | 11/1998 | Seilhamer et al. | 435/6 |
| 5,843,780 A | 12/1998 | Thomson | 435/363 |
| 5,856,136 A | 1/1999 | Au-Young | 435/69.3 |
| 5,914,268 A | 6/1999 | Keller et al. | 435/325 |
| 5,922,597 A | 7/1999 | Verfaillie et al. | 435/372.1 |
| 5,942,435 A | 8/1999 | Wheeler | 435/325 |
| 5,961,165 A | 10/1999 | Aizawa et al. | 435/4 |
| 5,968,829 A | 10/1999 | Carpenter | 435/467 |
| 6,040,180 A | 3/2000 | Johe | 435/377 |
| 6,261,556 B1 | 7/2001 | Weinrich et al. | 424/94.5 |

FOREIGN PATENT DOCUMENTS

| | | |
|---|---|---|
| EP | 0695 351 B1 | 12/1999 |
| FR | 2744133 | 8/1997 |
| WO | WO 94/07997 | 4/1994 |
| WO | WO 96/17627 | 6/1996 |
| WO | WO 97/21802 | 6/1997 |
| WO | WO 97/28253 | 8/1997 |
| WO | WO 97/30151 | 8/1997 |
| WO | WO 97/47734 | 12/1997 |

| WO | WO 98/00540 | 1/1998 |
| WO | WO 98/30679 | 7/1998 |
| WO | WO 98/43679 | 10/1998 |
| WO | WO 99/01552 | 1/1999 |
| WO | WO 99/10535 | 3/1999 |
| WO | WO 99/20741 | 4/1999 |
| WO | WO 99/42122 | 8/1999 |
| WO | WO 99/43785 | 9/1999 |

OTHER PUBLICATIONS

Lim et al. Proteomics, 2:1187-1203(2002).*
Amit, M., et al., Clonally Derived Human Embryonic Stem Cell Lines Maintain Pluripotency and Proliferative Potential for Prolonged Periods of Culture, Dev. Biology, 227:000-000 (2000).
Andrews, P., "Retinoic Acid Induces Neuronal Differentiation of a Cloned Human Embryonal Carcinoma Cell Line in Vitro," Dev. Biol., 103:285 (1984).
Baribault, H., et al., "Embryonic Stem Cell Culture and Gene Targeting in Transgenic Mice," Mol. Biol. Med. 6:481 (1989).
Becton Dickinson, "Product Specification Sheet: Matrigel Basement Membrane Matrix, Phenol-Red Free".
Berger, C., et al., "Self Renewal of Embryonic Stem Cells in the Absence of Feeder Cells and Exogenous Leukaemia Inhibitory Factor," Growth Factors, 14:145 (1997).
Bodnar, a., et al., "Extension of Life-Span by Introduction of Telomerase into Normal Human Cells," Science, 279:349 (1998).
Bongso, A., et al., "Improved Quality of Human Embryos When Co-Cultured with Human Ampullary Cells," Hum. Reprod., 4:706 (1989).
Bradley, A., et al., "Modifying the Mouse: Design and Desire," Biotechnology, 10:534 (1992).
Brook, F., et al., "The Origin and Efficient Dirivation of Embryonic Stem Cells in the Mouse," Proc. Natl. Acad. Sci., 94:5709 (1997).
Carnegie, J., "Immunolocalization of Fibronectin and Laminin Within Rat Blastocysts Cultured Under Serum-Free Conditions," j. Reprod. Fert., 91:423 (1991).
Carninci, P., et al., "High-Efficiency Full-Length cDNA Cloning," Methods Enzymol., 303:19 (1999).
Clontech Laboratories, SMART cDNA Library Construction Kit, Catalog #K1051-1.
Corrick, C., et al., "Construction of a Mouse Blastocyct cDNA Library by PCR Amplification From Total RNA," Molecular Reproduction and Development, 43:7 (1996).
Deleersnijder, W., et al., "Isolation of markers for chondro-osteogenic differentiation using cDNA library subtraction. Molecular cloning and characterization of a gene belonging to a novel multigene family of integral membrane proteins", J Biol Chem, 271:19475 (1996).
Eisen, M., "Cluster Analysis and Display of Genome-wide Expression Patturns," Proc. Natl. Acad. Sci., 95:14868 (1998).
Elges, R., et al., "Establishment of Human Embryonic Stem Cell-Transfected Clones Carrying a Marker for Undifferentiatied Cells," Curr Biol, 11:514 (2001).
Evans, M., et al., "Establishment in Culture of Pluripotential Cell from Mouse Embryos," Nature, 292:154 (1981).
Fenderson, B., et al., "Carbohydrate Antigens of Embryonal Carcinoma Cells: Changes Upon Differentiation," APMIS Suppl. 27, 100:109 (1992).
Finley, M., et al., "Synapse Formation and Establishment of Neuronal Polarity by P19 Embryonic Carcinoma Cells and Embryonic Stem Cells," J. Neuroscience, 16:1056 (1996).

Gardner, D., et al., "Culture and Transfer of Human Blastocysts Increases Implantation Rates and Reduces the Need for Multiple Embryo Transfers," Fertil. Steril, 69:84 (1998).
Gendall, A., et al., "Isolation and Characterization of a Leukemia Inhibitory Factor-Independent Embryonic Stem Cell Line," Int. J. Biochem Cell Biol., 29:829 (1997).
Gendron, R., et al., "Induction of Embryonic Vasculogenesis by bFGF and LIF in Vitro and in Vivo," Developmental Biology, 177:332 (1996).
GibcoBrl Life Technologies Catalogue and Ref. Guide, pp. 1-2 through 1-4, 1-94 and 1-95 (1993).
Itoh, M., et al., "Automated Filtration-Based High-Throughput Plasmid Preparation System," Genome Res., 9:463 (1999).
Itskovitz-Eldor, J., et al., "Differentiation of Human Embryonic Stem Cells into Embryoid Bodies Comprising the Three Embryonic Germ layers," Mol. Med., 6:68 (2000).
Keller, G., "In Vitro Differentiation of Embryonic Stem Cells," Cell Biology, 7:862 (1995).
Kelly, DL., et al., "DNA Microarray Analyses of Genes Regulated During the Differentiation of Embryonic Stem Cells," Mol Reprod. Dev., 56:113 (2000).
Ko, M., et al., " Large-scale cDNA analysis Reveals Phased Gene Expression Patterns During Preimplantation Mouse Development," Development, 127:1737 (2000).
Koshimizu, U., et al., "Functional Requirement of gp130-mediated Signaling for Growth and Survival of Mouse Primordial Germ Cells In Vitro and Derivation of Embryonic Germ (EG) Cells," Develoment, 122:1235 (1996).
Koshimizu, U., et al., "Rapid Communication Retinoic Acid Is a Potent Growth Activator of Mouse Primordial Germ Cells In Vitro," Developmental Biology, 168:683 (1995).
Life Technologies, Inc., "SuperScript II; Rnase H Reverse Transcriptase," Product Brochure; pp. 1-4.
Matsuda, T., et al., "STAT3 Activiation is Sufficient to Maintain an Undifferentiated State of Mouse Embryonic Stem Cells," EMBO J., 18:4261 (1999).
Matsui, Y., et al., "Derivation of Pluripotential Embryonic Stem Cells from Murine Primordial Germ Cells in Culure," Cell, 70:841 (1992).
Nichols, J., et al., "Establishment of Germ-line-Competent Embryonic Stem (ES) Cells Using Differentiation Inhibiting Activity," Development, 110:1341 (1990).
Nichols, J., et al., "Derivation of Germline Competent Embryonic Stem Cells with a Combination of Interleukin-6 and Soluble Interleukin-6 Receptor," Experimetnal Cell Research, 215:237 (1994).
O'Shea, K., "Embryonic Stem Cell Models of Development," New Anat., 257:32 (1999).
Pease, S., et al., "Isolation of Embryonic Stem (ES) Cells in Media Supplemented with Recombinant Leukemia Inhibitory Factor (LIF)," Developmetnal Biology, 141:344 (1990).
Pera, M., "Human Pluripotent Stem Cells: a Progress Report," Curr Opin Genet Dev, 11:595 (2001).
Pedersen, R., "Studies of In Vitro Differentiation with Embryonic Stem Cells," Reprod. Fertil. Dev., 6:543 (1994).
Pedersen, R., "Embryonic Stem Cell for Medicine," Scientif. Am., 280:68 (1999).
Rathjen, J., et al., "Formation of a Primitive Ectoderm Like Cell Population, EPL Cells, from ES Cells in Response to Biologically Derived Factors," J. of Cell Sci., 112:601 (1999).
Rehman, N., et al., "Development of IVM-IVF Produced 8-Cell Bovine Embryos in Simple, Serum-Free Media After Conditioning of Co-Culture With Buffalo Rat Liver Cells," Mol. Repro. Dev, 38:251 (1994).

Reubinoff, B., et al., "Embryonic Stem Cell Lines From Human Blastocysts: Somatic Differentiation In Vitro," Nat. Biotechnology, 18:399 (2000).

Robertson, E., "Derivation and Maintenance of Embryonic Stem Cell Cultures," Methods in Mol. Bio., 75:173 (1997).

Rose, T., et al., "Oncostatin M (OSM) Inhibits the Differentiation of Pluripotent Embryonic Stem Cells In Vitro," Cytokine, 6:48 (1994).

Shamblott, M., et al., "Human Embryonic Germ Cell Derivatives Express a Broad Range of Developmentally Distinct Markers and Proliferate Extensively in Vitro," PNAS, 98: 118 (2001).

Shamblott, M., et al., "Derivation of Pluripotent Stem Cells from Cultured Human Primordial Germ Cells," Proc. Natl. Acad. Sci. USA, 95:13726 (1998).

Smith, A., et al., "Inhibition of Pluripotential Embryonic Stem Cell Differentiation by Purified Polypeptides," Nature, 336:668 (1998).

Smith A., et al., "Buffalo Rat Liver Cells Produce a Diffusible Activity Which Inhibits the Differentiation of Murine Embryonal Carcinoma and Embryonic Stem Cells," Dev. Biol., 121:1 (1987).

Sigma, Product Information for Laminins for Cell Culture.

Takahashi, N., et al., "Toward a Whole cDNA Catalog: Construction of an Equalized cDNA library from Mouse Embryos," Genomics, 23:202 (1994).

Thomson, J., et al., "Embryonic Stem Cell Lines Derived from Human Blastocysts," Science, 282:145 (1998).

Thomson, J., et al., "Neural Differentiation of Rhesus Embryonic Stem Cells," APMIS, 106:149 (1998).

Thomson, J., et al., "Isolation of a Primate Embryonic Stem Cell Line," Proc. Natl. Acad. Sci. USA, 92:7844 (1995).

Thomson, J., et al., "Primate Embryonic Stem Cells," Current Topics in Developmental Biology, 38:133 (1998).

Vassilieva, S., et al., "Establishment of SSEA-1- and Oct-4-Expressing Rat Embryonic Stem-like Cell Lines and Effects of Cytokines of the IL-6 Family on Clonal Growth," Exper. Cell Research, 258:361 (2000).

Worrall, D., et al., "A Carrot Leucine-Rich-Repeat Protein That Inhibits Ice Recrystallization," Science, 282:115 (1998).

Wenk, J., et al., "Glycolipids of Germ Cell Tumors: Extended Globo-Series Glycolipids are a Hallmark of Human Embryonal Carinoma Cells," Int. J. Cancer, 58:108 (1994).

Williams, R., et al., "Myeloid Leukaemia Inhibitory Factor Maintains the Developmental Potential of Embryonic Stem Cells," Nature, 336:684 (1988).

Woltjen, K., et al., "Retro-recombination Screening of a Mouse Embryonic Stem Cell Genomic Library," Nucleic Acids Research, 28:e41 (2000).

Xiong, J., et al., "Large-Scall Screening for Developmental Genes in Embryonic Stem Cells and Embryoid Bodies Using Retroviral Entrapment Vectors," Dev. Dynamics, 212:181 (1998).

Zandstra, P., et al., "Leukenia Inhibitory Factor (LIF) Concentration Modulates Embryonic Stem Cell Self-Renewal and Differentiation Independently of Proliferation," Biotechnol. Bioeng., 69:607 (2000).

\* cited by examiner

*Primary Examiner*—Joseph Woitach
*Assistant Examiner*—Thaian N. Ton
(74) *Attorney, Agent, or Firm*—J. Michael Schiff; David J. Earp

(57) ABSTRACT

This disclosure provides an improved system for culturing human pluripotent stem (pPS) cells in the absence of feeder cells. The role of the feeder cells can be replaced by supporting the culture on an extracellular matrix, and culturing the cells in a conditioned medium. Permanent cell lines are provided that can produce conditioned medium on a commercial scale. Methods have also been discovered to genetically alter pPS cells by introducing the cells with a viral vector or DNA/lipid complex. The system described in this disclosure allows for bulk proliferation of pPS cells for use in studying the biology of pPS cell differentiation, and the production of important products for use in human therapy.

27 Claims, 15 Drawing Sheets

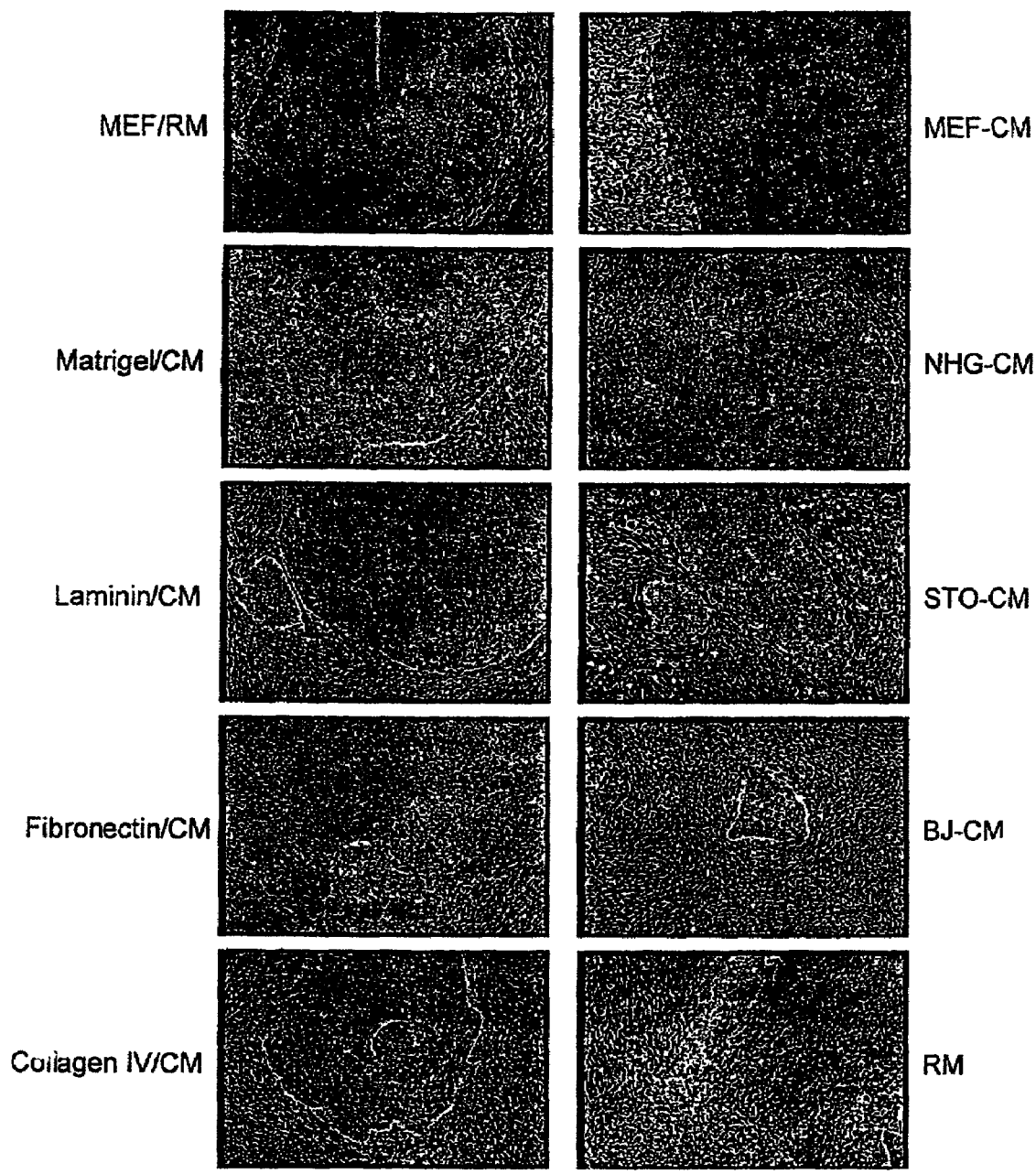

Figure 1C:
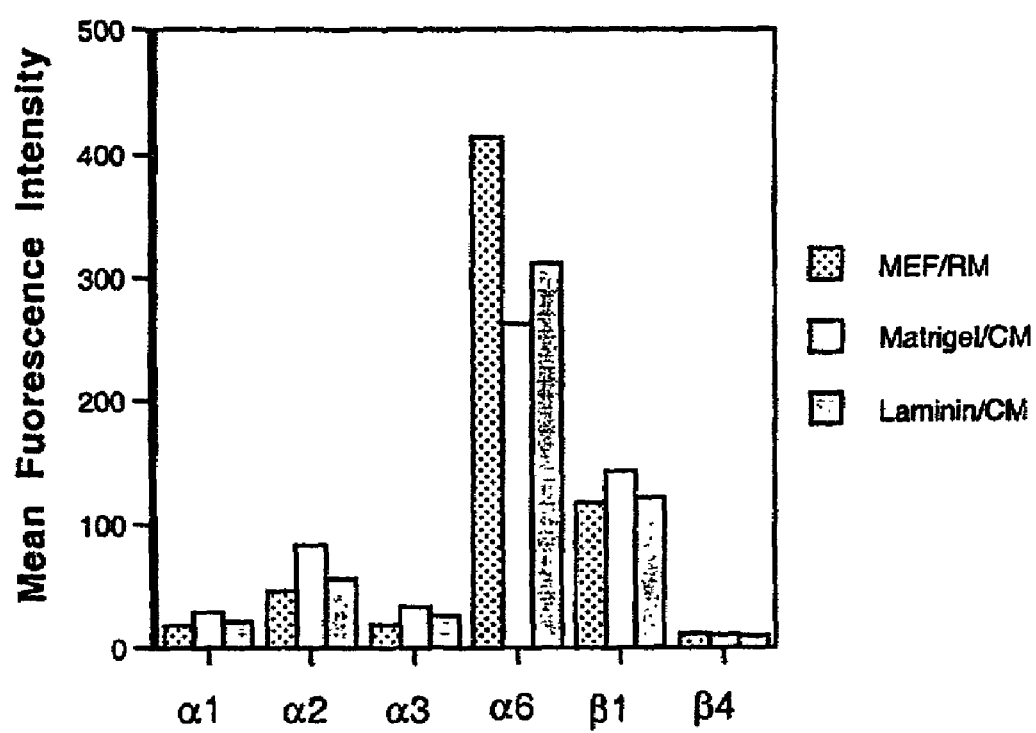

Figure 11
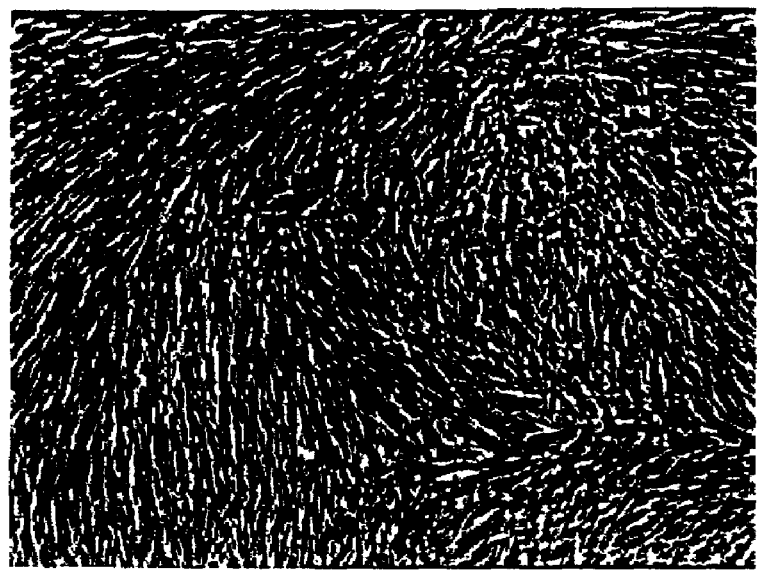
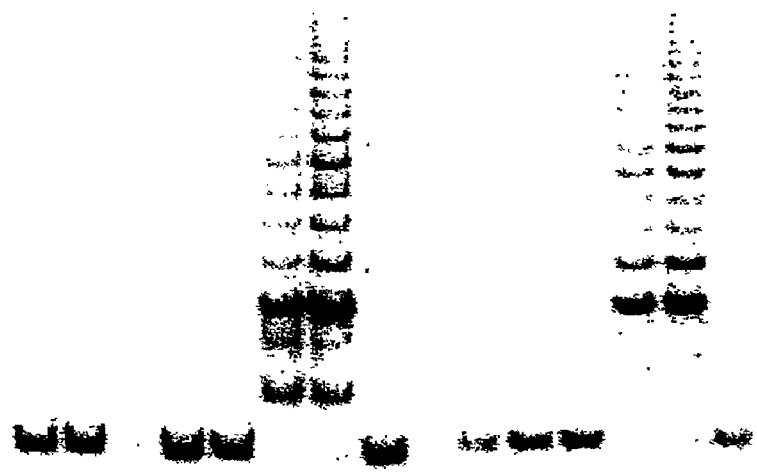

Figure 13
HEF1-hTERT
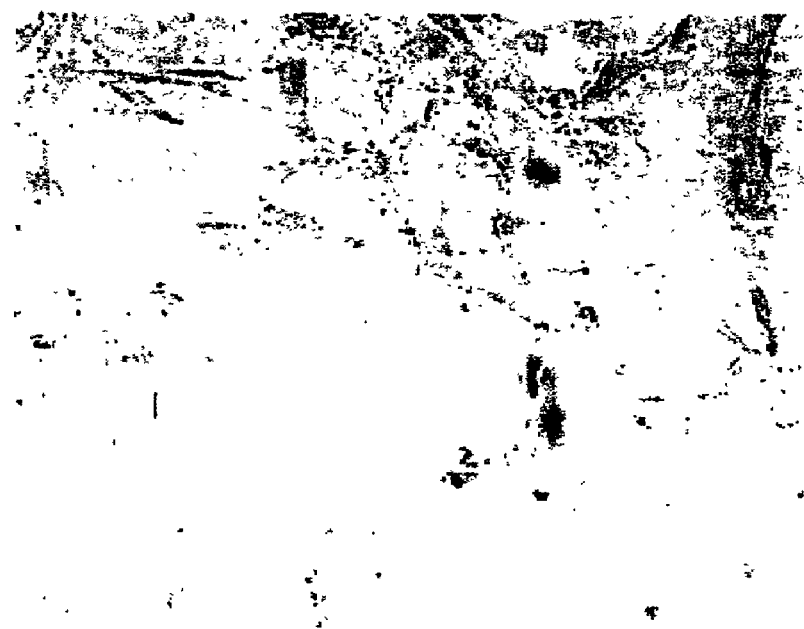
HEF1-control

```
                           SEQUENCE LISTING

<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: primer

<400> SEQUENCE: 1
aggtcgacga gagag                                                      15

<210> SEQ ID NO 2
<211> LENGTH: 15
<212> TYPE: DNA
<213> ORGANISM: Artificial Sequence
<220> FEATURE:
<223> OTHER INFORMATION: primer

<400> SEQUENCE: 2
ctctctcgtc gacct                                                      15

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
cttgctgcag aagtgggtgg aggaa                                           25
```

```
<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ctgcagtgtg ggtttcgggc a                                      21

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cggaagagtg tctggagcaa                                        20

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
ggatgaagcg gagtctgga                                         19
```

USE OF HUMAN EMBRYONIC STEM CELLS FOR DRUG SCREENING AND TOXICITY TESTING

REFERENCE TO RELATED APPLICATIONS

This application is a continuation of U.S. Ser. No. 09/859,291, filed May 16, 2001 (pending) which is a continuation of PCT/US01/01030, designating the U.S. and filed Jan. 10, 2001 (published as WO 01/51616 on Jul. 19, 2001), which is a continuation-in-part of U.S. Ser. No. 09/688,031, filed Oct. 10, 2000 (now U.S. Pat. No. 6,667,176) and claims priority to U.S. Ser. No. 60/175,581, filed Jan. 11, 2000; U.S. Ser. No. 60/213,740, filed Jun. 22, 2000; U.S. Ser. No. 60/213,739, filed Jun. 22, 2000; U.S. Ser. No. 60/216,387, filed Jul. 7, 2000; and U.S. Ser. No. 60/220,064, filed Jul. 21, 2000.

The priority applications are hereby incorporated herein by reference in their entirety.

TECHNICAL FIELD

This invention relates generally to the field of cell biology of embryonic cells. More specifically, it relates to the propagation of human pluripotent stem cells, culture conditions that facilitate propagation, and their use for genetic alteration, producing cDNA libraries, and producing differentiated cells for tissue regeneration.

BACKGROUND

Recent discoveries have raised expectations that stem cells may be a source of replacement cells and tissues that are damaged in the course of disease, infection, or because of congenital abnormalities. Various types of putative stem cells differentiate when they divide, maturing into cells that can carry out the unique functions of particular tissues, such as the heart, the liver, or the brain. A particularly important discovery has been the development of pluripotent stem cells, which are thought to have the potential to differentiate into almost any cell type.

Early work on pluripotent stem cells was done in mice (reviewed in Robertson, Meth. Cell Biol. 75:173, 1997; and Pedersen, Reprod. Fertil. Dev. 6:543, 1994). Mouse stem cells can be isolated from both early embryonic cells and germinal tissue. Desirable characteristics of pluripotent stem cells are that they be capable of indefinite proliferation in vitro in an undifferentiated state, retain a normal karyotype, and retain the potential to differentiate to derivatives of all three embryonic germ layers (endoderm, mesoderm, and ectoderm).

The development of preparations of human pluripotent stem cells has involved overcoming a number of technical difficulties, and is considerably less advanced than work with mouse cells.

Thomson et al. (U.S. Pat. No. 5,843,780; Proc. Natl. Acad. Sci. USA 92:7844, 1995) were the first to successfully isolate and propagate pluripotent stem cells from primates. They subsequently derived human embryonic stem (hES) cell lines from human blastocysts (Science 282:114, 1998). Gearhart and coworkers derived human embryonic germ (hEG) cell lines from fetal gonadal tissue (Shamblott et al., Proc. Natl. Acad. Sci. USA 95:13726, 1998; and U.S. Pat. No. 6,090,622).

Both hES and hEG cells are reported to have the long-sought characteristics of pluripotent stem cells: they are capable of long-term proliferation in vitro without differentiating, they have a normal karyotype, and they remain capable of producing a number of different cell types. Because of this, they hold considerable promise for use in human therapy, acting as a reservoir for regeneration of almost any tissue compromised by genetic abnormality, trauma, or a disease condition.

A significant challenge to the use of pluripotent stem cells for therapy is that they are traditionally cultured on a layer of feeder cells to prevent differentiation (U.S. Pat. No. 5,843,780; U.S. Pat. No. 6,090,622). Without feeder cells in the culture environment, hPS cells soon die, or differentiate into a heterogeneous population of committed cells. Leukemia inhibitory factor (LIF) inhibits differentiation of mouse PS cells, but it does not replace the role of feeder cells in preventing differentiation of human PS cells. Unfortunately, using feeder cells increases production costs, impairs scale-up, and produces mixed cell populations that require the pluripotent stem cells to be separated from feeder cell components.

Another challenge is to control differentiation of stem cells into the particular type of tissue required for treatment of each patient. It is a hypothesis of this invention that better understanding of the differentiation process will be obtained by observing gene expression during growth and differentiation of pluripotent stem cells.

International Patent Publication WO 99/20741 (Geron Corp.) is entitled *Methods and Materials for the Growth of Primate-Derived Primordial Stem Cells*. A cell culture medium is provided for growing primate-derived primordial stem cells in a substantially undifferentiated state, having a low osmotic pressure and low endotoxin levels. The basic medium is combined with a serum effective to support the growth of primate-derived primordial stem cells on a substrate of feeder cells or a feeder cell matrix. The medium further includes non-essential amino acids, an anti-oxidant, and growth factors that are either nucleosides or a pyruvate salt.

Sequence-based studies of early human development have focused on libraries produced from fetal organs and tissues for example, fetal libraries from the I.M.A.G.E. consortium; http://image.llnl.gov/). International Patent Publication WO 98/00540 (Incyte) reports partial sequences of stem cell antigens, isolated from cDNA libraries derived from THP-1 cells and bladder tumors.

New technology to facilitate growing and manipulating undifferentiated pluripotent stem cells would be a major achievement towards realizing the full potential of embryonic cell therapy.

SUMMARY OF THE INVENTION

This disclosure provides an improved system for culturing primate pluripotent stem (pPS) cells in the absence of feeder cells. The role of the feeder cells is replaced by supporting the culture on an extracellular matrix, and culturing the cells in a conditioned medium. Permanent cell lines are provided that can produce conditioned medium on a commercial scale. Methods have also been discovered to genetically alter pPS cells by introducing the cells with a viral vector or DNA/lipid complex. The system described in this disclosure allows for bulk proliferation of pPS cells for use in studying the biology of pPS cell differentiation, and the production of important products for use in human therapy.

Described in this disclosure are compositions comprising proliferating pPS cells that are essentially free of feeder cells. The compositions may also comprise a conditioned medium produced by collecting medium from a culture of feeder cells, and a substrate coated with extracellular matrix components. pPS cells may be passaged and expanded in this growth environment in the undifferentiated state.

This disclosure also provides a method for producing a conditioned medium suitable for culturing primate pluripotent stem (pPS) cells in a growth environment essentially free of feeder cells, comprising conditioning medium by culturing cells in the medium, and harvesting the conditioned medium. The cells used to condition the medium may have one or more desirable features, such as being from a non-malignant source and having a normal karyotype, being capable of extensive culture (such as 60 days or more), have morphological features or cell markers characteristic of fibroblasts, and be immortalized (for example by being genetic altered to express telomerase reverse transcriptase). Methods for producing suitable human feeder cell lines from human embryonic stem cells are described.

This disclosure provides a method of producing a differentiated cell population, comprising causing or permitting pPS cells in feeder-free culture to differentiate.

This disclosure also provides a method for producing differentiated cells from pPS cells (cultured with or without feeder cells) by direct differentiation. A suspension of cells is prepared from an undifferentiated donor culture before there is overgrowth, formation of colonies, embryoid bodies, or other aggregates, and then plating directly onto a solid surface. The surface may bear a poly-cation (such as polylysine or poly-ornithine). Differentiation down certain cell lineages can also be promoted by withdrawing serum or factors that inhibit differentiation and/or adding a factor that promotes differentiation, either in feeder-free culture or after replating.

This disclosure also provides a method of screening a compound for cellular toxicity or modulation of the cell, comprising contacting a differentiated cell of this invention with the compound, determining any phenotypic or metabolic changes in the cell that result from contact with the compound, and correlating the change with cellular toxicity or any other change in cell function or biochemistry.

Gene and protein expression can be compared between different cell populations obtained from pPS cells, and used to identify and characterize factors upregulated or downregulated in the course of differentiation, and produce nucleotide copies of the affected genes.

This disclosure also provides methods for producing genetically altered primate pluripotent stem (pPS) cells. In one variation, pPS cells are transfected in feeder-free cultures. In another variation, pPS cells are transfected in cultures containing feeder cells that are drug-resistant, and will withstand drug selection of the successfully transfected pPS cells. The vector used for transfection often comprises a protein encoding region operably linked to a promoter that promotes transcription in undifferentiated pPS cells. Also provided is a population of primate pluripotent stem (pPS) cells or cells differentiated therefrom, in which a substantial proportion of the cells have been stably transfected with a polynucleotide, or are the progeny of such cells that have inherited the polynucleotide.

This disclosure also provides a method of producing an mRNA preparation or a cDNA library from primate pluripotent stem (pPS) cells before or after differentiation, comprising providing a culture of undifferentiated pPS cells essentially free of feeder cells, optionally permitting the pPS cells to differentiate, and isolating mRNA from the undifferentiated or differentiated cells. These techniques can be used to prepare cDNA expression and subtraction libraries. When the mRNA is obtained from feeder-free pPS cultures, the cDNA libraries may comprise at least 1,000 genes expressed at the mRNA level in either undifferentiated pPS cells, or cells differentiated from pPS cells, and be essentially free of cDNA of other vertebrates. Sequence information for genes expressed in undifferentiated pPS cells, and their differentiated progeny, can be used to prepare cDNA and protein derivatives of the expressed genes, and specific antibody to the gene product.

These and other aspects of the invention will be apparent from the description that follows.

DRAWINGS

FIG. 1 is a half-tone reproduction of photomicrographs showing the morphology of hES cells in feeder-free culture. Panel A (Left Side) shows morphology of hES cells cultured on feeder cells in regular culture medium (mEF/RM), or on Matrigel®, laminin, fibronectin, or collagen IV in mEF conditioned medium. Panel B (Right Side) shows morphology of hES cells maintained on Matrigel® in medium conditioned by mEF, NHG190, STO and BJ 5Ta cells, compared with unconditioned regular medium (RM). hES cells in regular medium differentiated within the first week of culture. hES cells in certain types of conditioned media contained colonies with appropriate morphology for undifferentiated cells. Panel C is a bar graph showing integrin expression measured in hES cells maintained on feeders in regular medium (mEF/RM) or on Matrigel® or laminin in mEF conditioned medium. Integrin components α6 and β1 may play a role in adherence of hES cells to extracellular matrix.

Figure 2:
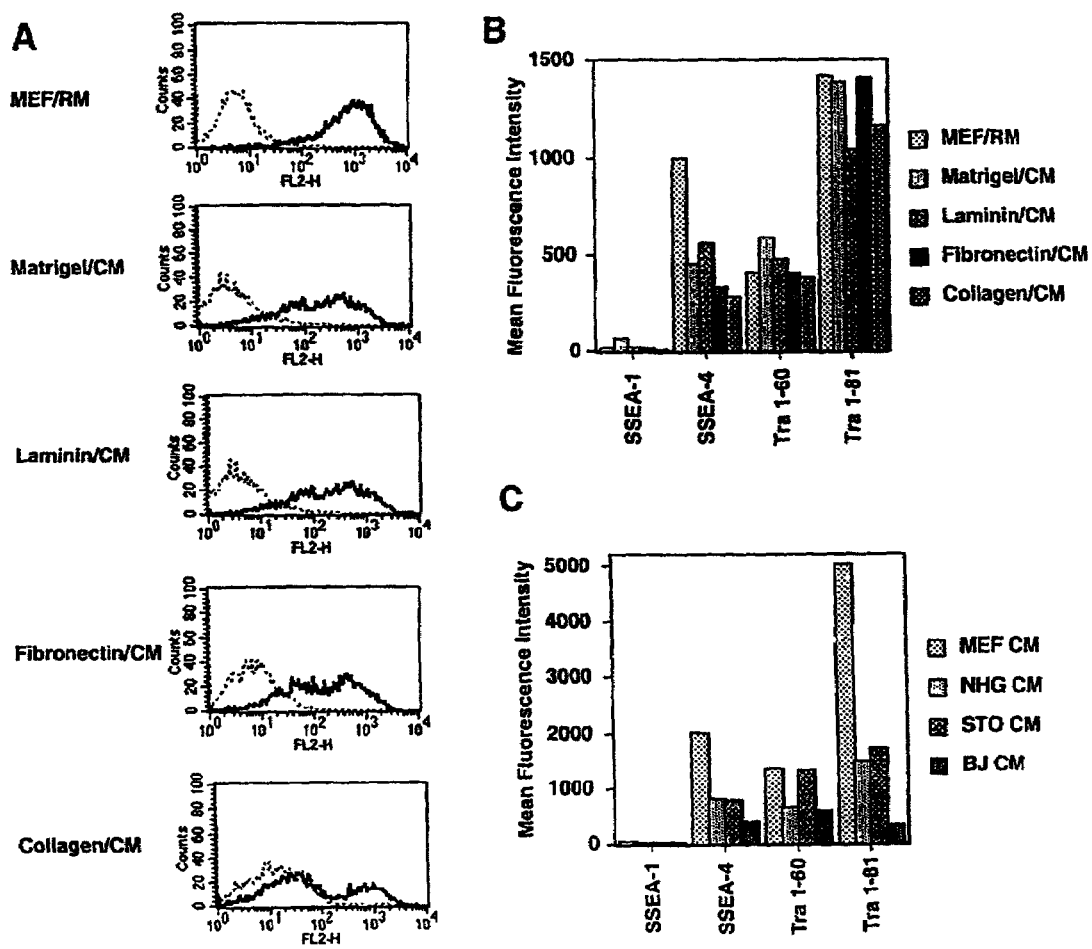

FIG. 2 shows surface marker expression in feeder-free cells by FACS analysis. Panel A is a FACS scan profile showing expression of SSEA-4, a glycoprotein expressed by hES cells grown on feeders in regular medium (mEF/RM), or on extracellular matrix with conditioned medium. Panel B is a bar graph showing fluorescence intensity of surface markers for hES cells cultured on different matrices. Panel C is a bar graph showing surface markers for hES cells cultured on Matrigel® in conditioned medium from different cell lines.

Figure 3:
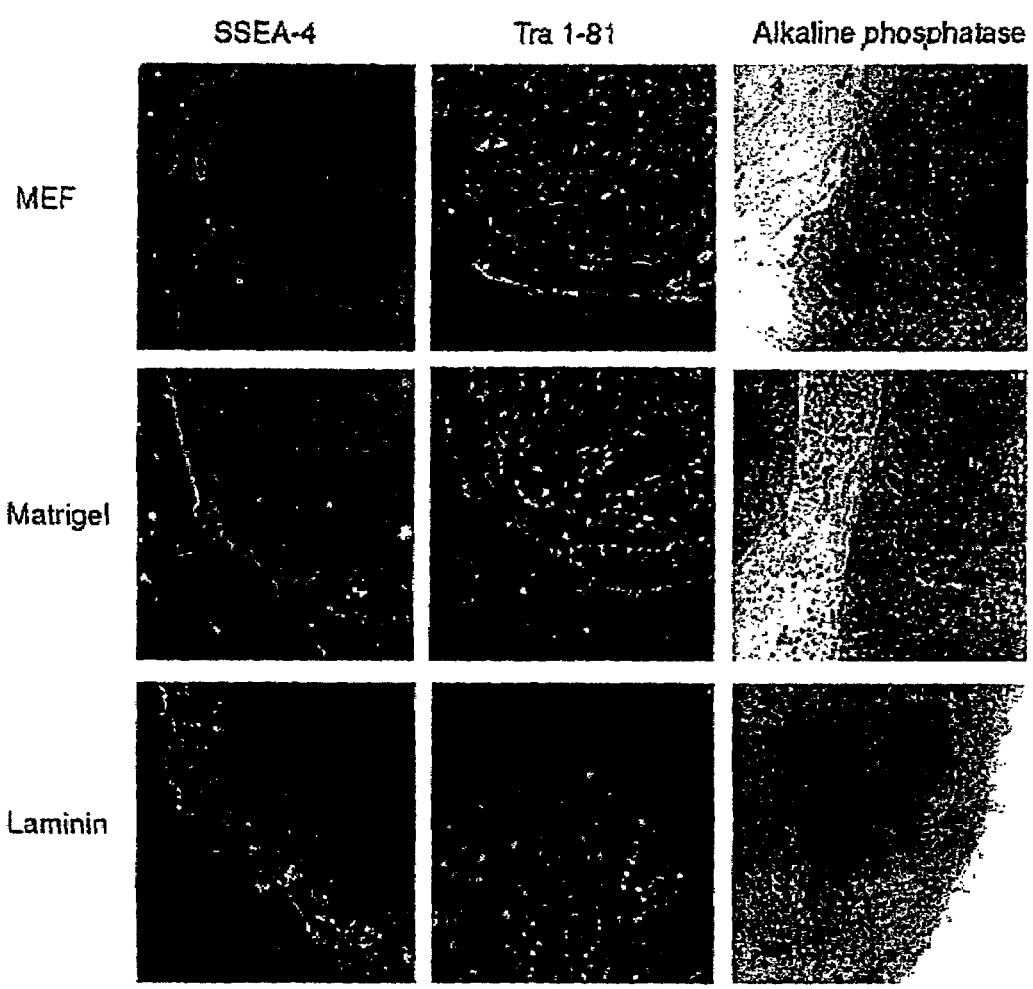

FIG. 3 is a half-tone reproduction of micrographs showing marker expression detected by immunocytochemistry for cells grown with primary feeder cells (mEF) or on the extracellular matrices Matrigel® or laminin in conditioned medium. hES cells grown in feeder-free culture have phenotypic markers similar to those of hES grown on mouse fibroblast feeder cells.

Figure 4:
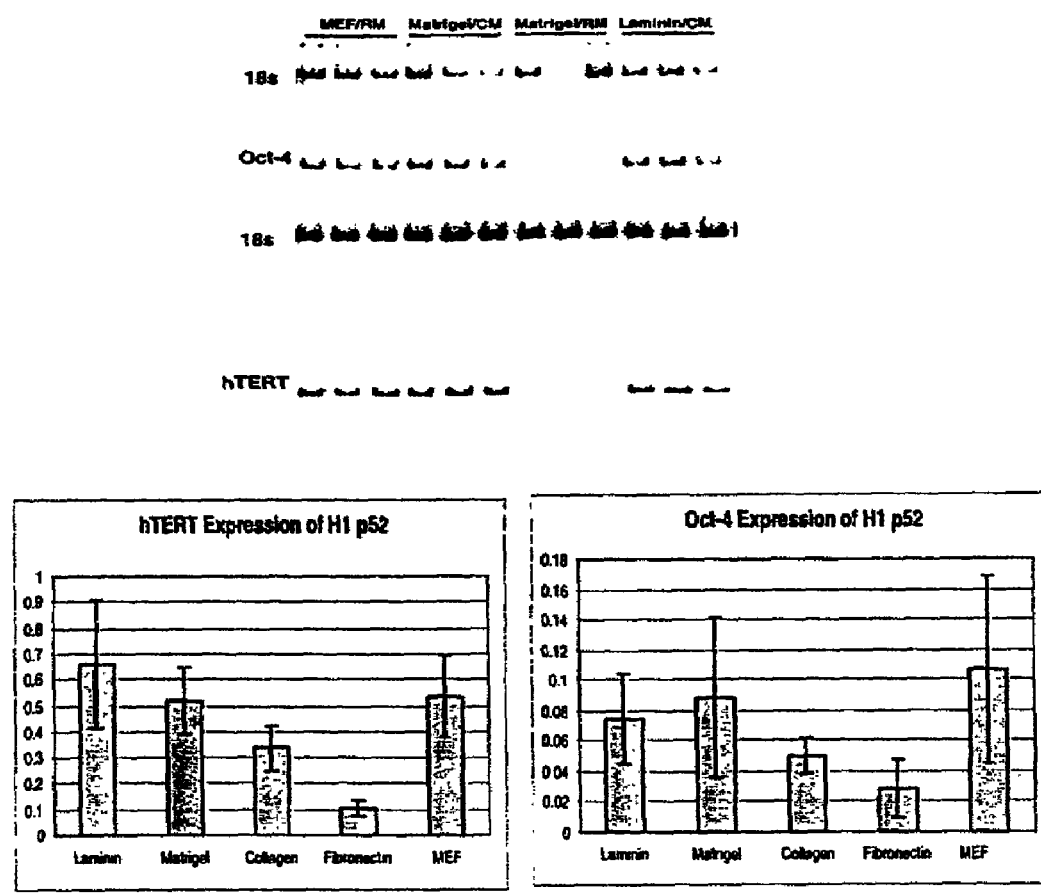

FIG. 4 provides an analysis of OCT-4 and hTERT expression in hES cells cultured with feeder cells (mEF) or extracellular matrix (Matrigel® or laminin) with regular medium (RM) or conditioned medium (CM). The upper panel is a copy of a gel showing OCT-4 and hTERT expression at the mRNA level by RT-PCR. The lower panel is a bar graph comparing the level of expression for cells grown on different substrates, expressed as the ratio of OCT-4 or hTERT to the 18s standard. hES cells grown on Laminin and Matrigel® in conditioned medium have similar expression patterns to those of cells grown on a feeder layer.

Figure 5:
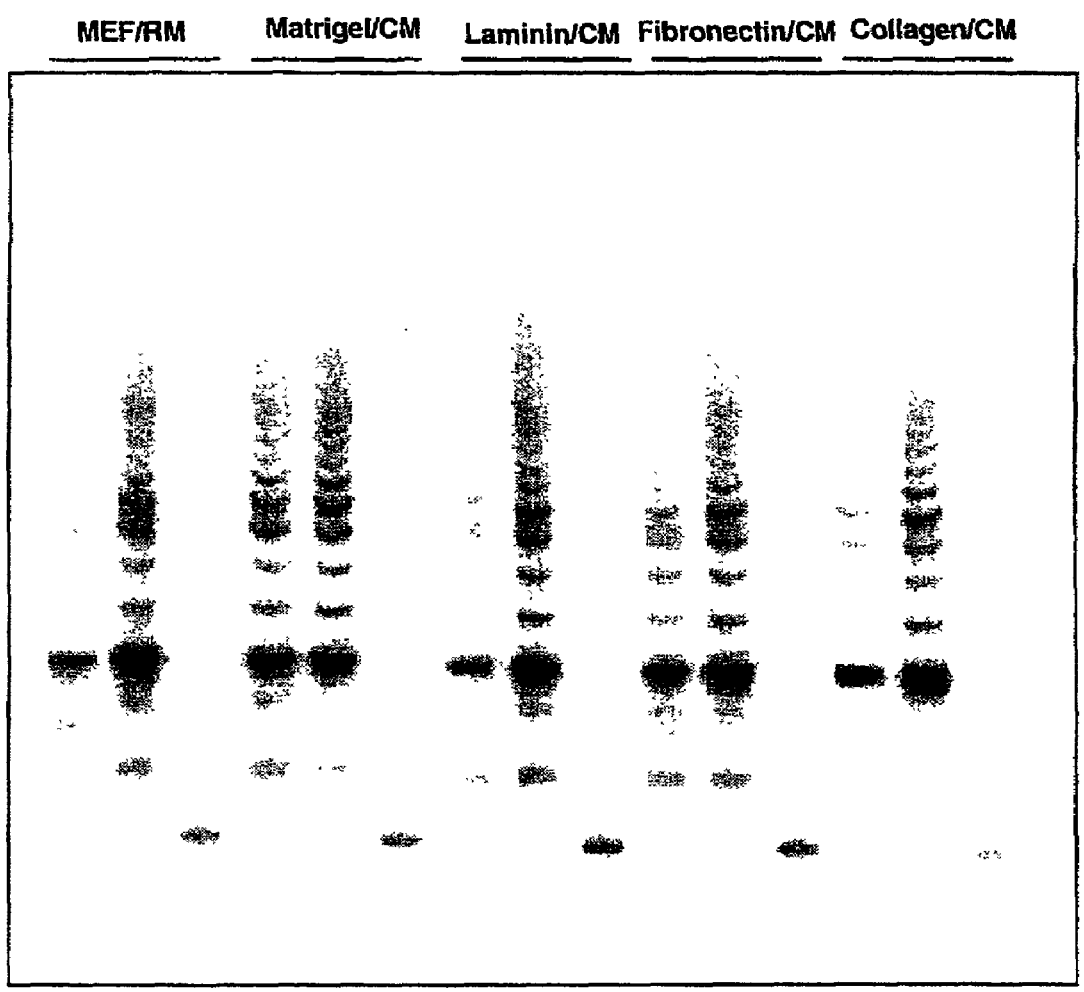

FIG. 5 is a half-tone reproduction of a gel showing telomerase activity measured in cultured hES cells by TRAP assay. All the culture conditions showed positive telomerase activity after 40 days in feeder-free culture.

Figure 6:
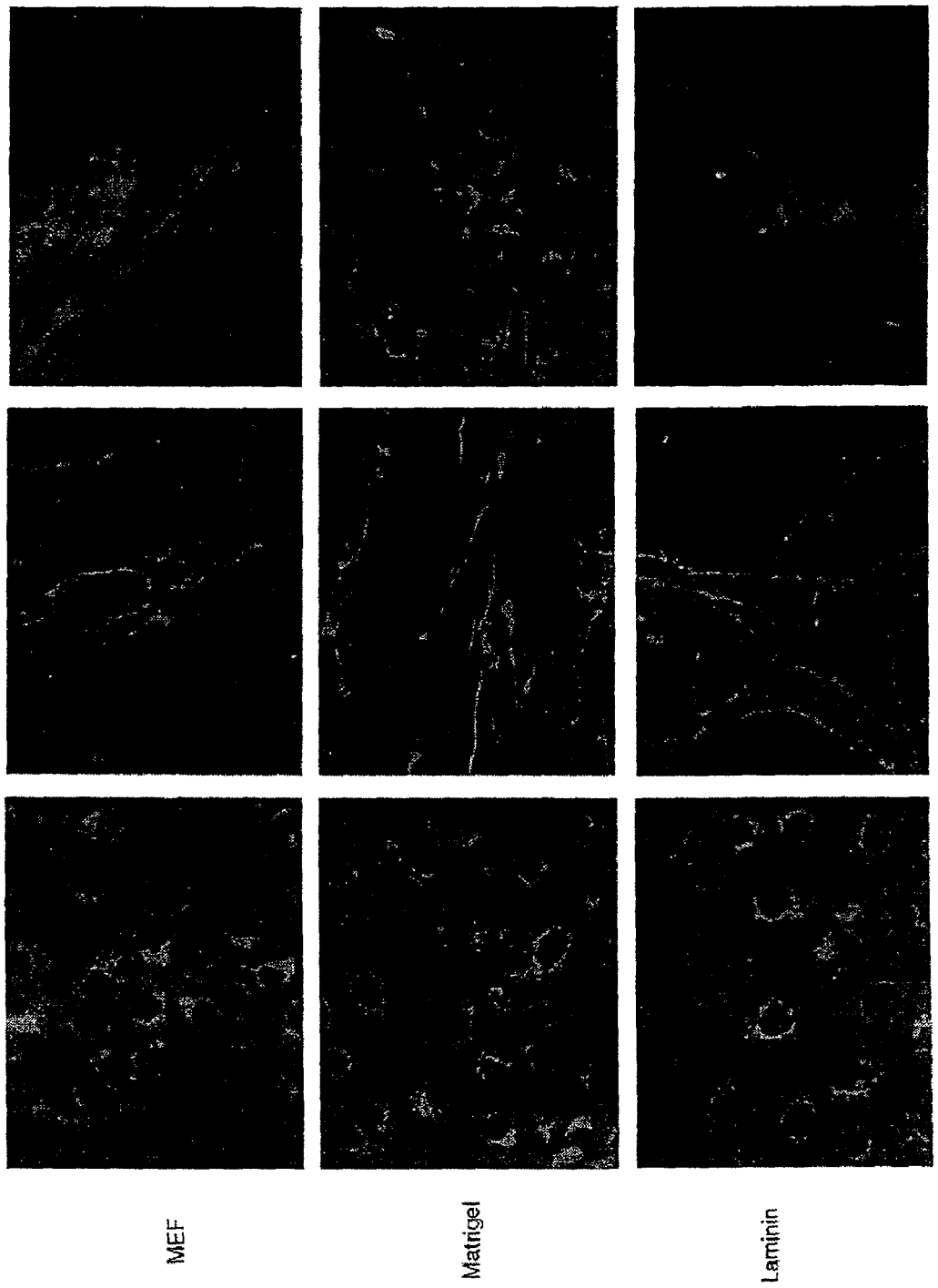

FIG. 6 is a half-tone reproduction of immunocytochemistry performed on cultured hES cells that were allowed to differentiate through embryoid body formation. Regardless of whether the hES had been cultured on feeders or on extracellular matrix, the staining patterns are consistent with a potential for differentiation into different cell types. The staining patterns show cells of the neuron and cardiomyocyte lineages (β-tubulin III and cardiac troponin I, respectively. There are also cells staining for α-fetoprotein, a marker of endoderm lineage.

Figure 7:
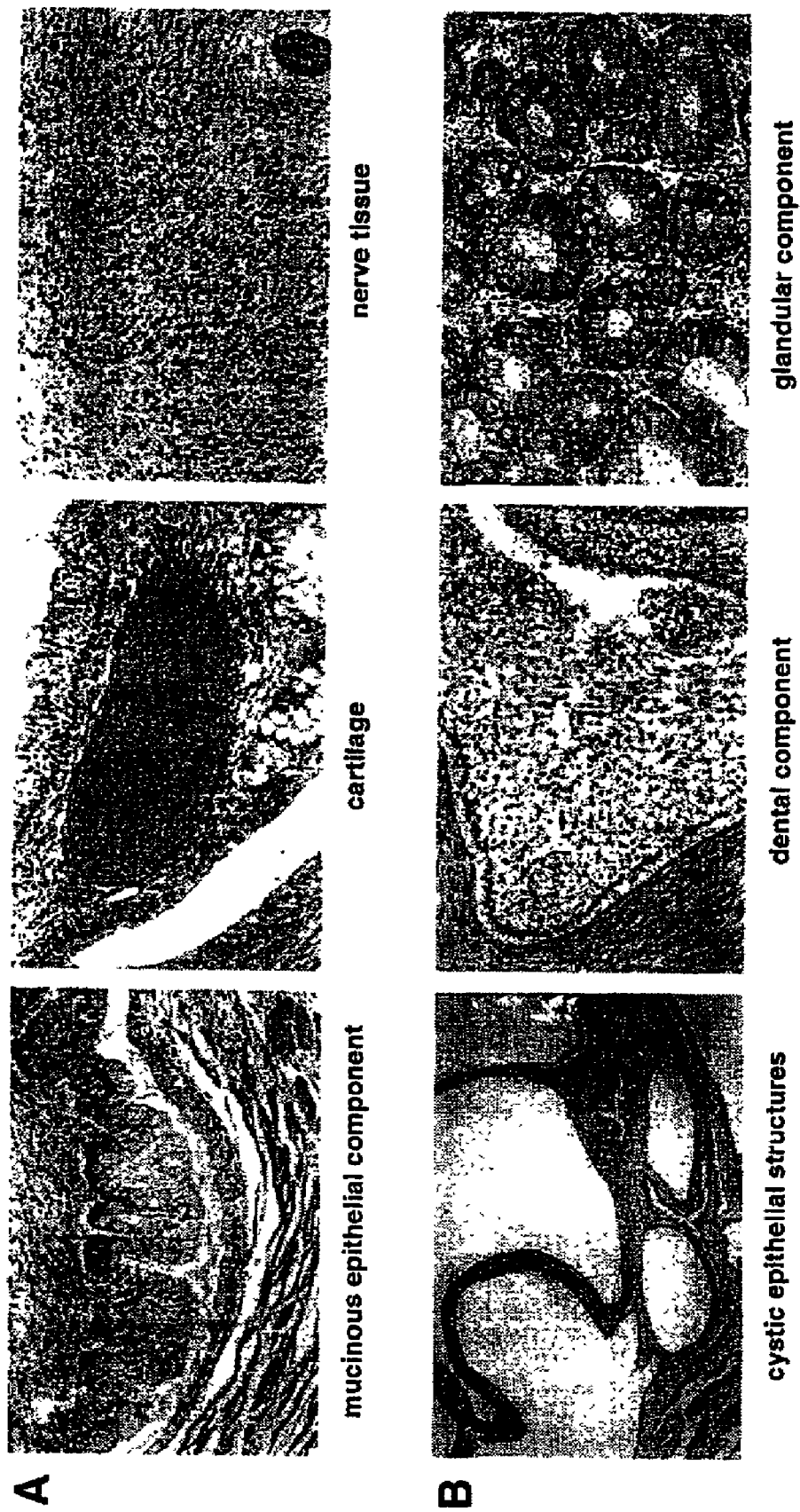

FIG. 7 is a half-tone reproduction of the histopathology of teratomas derived from hES cells, as another indicator of their ability to differentiate into different cell lineages. Panel A (Upper Row) shows a number of different cells in teratomas from hES grown on mEF feeder cells. Panel B (Lower Row) shows different cells in teratomas from hES grown in feeder-free culture.

Figure 8:
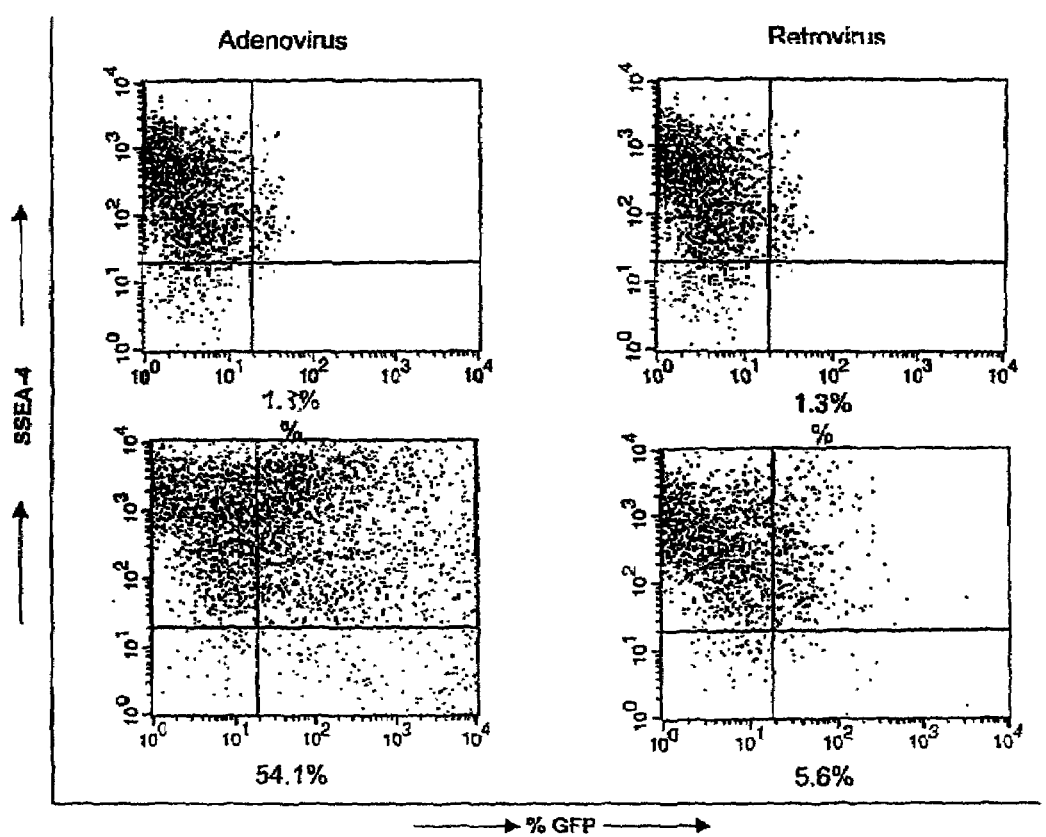

FIG. 8 is a FACS profile of transduced hES cells for GFP expression and SSEA-4, a marker of undifferentiated cells. hES cells were plated on feeder layers and infected 48 h later with either the adenoviral vector Ad5GFP or the retroviral vector GRN354, both of which include a GFP expression cassette. The cells were harvested, stained with an antibody against SSEA-4, and assessed for GFP expression by flow cytometry. Upper panels show the background fluorescence and SSEA-4 positive staining in mock-infected cultures. Lower panels show the level of green fluorescence resulting from expression of the GFP.

Figure 9:
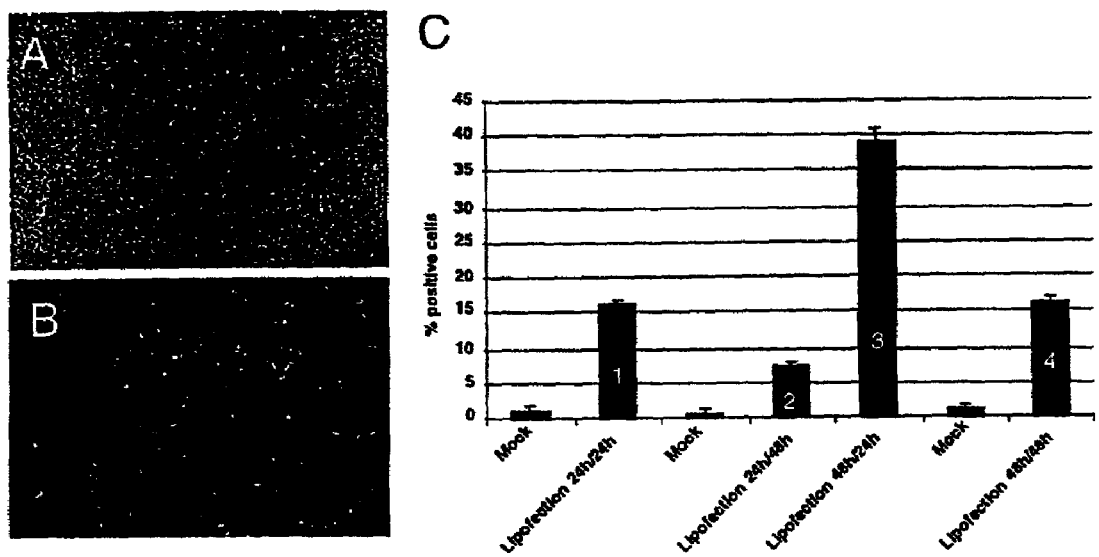

FIG. 9 shows the results of an experiment in which hES were genetically altered in feeder-free culture by lipofection. Panel A is a half tone of a light micrograph showing morphology of hES cells on laminin after they have been transfected for GFP expression. Panel B is a half tone of a fluorescence micrograph showing GFP expression in the same colony. Panel C is a bar graph showing percentage of cells expressing GFP under various conditions.

FIG. 10 is a bar graph showing the percentage of GFP-positive cells in SSEA-4 positive cell population (undifferentiated ES cells). Panel A: Bright green cells were observed in undifferentiated hES colonies of feeder-free cultures. In contrast, very few green cells were found in hES cell colonies grown on feeders. FACS analysis showed that 16% of cells on Matrigel® and 14% of cells on laminin were GFP positive in the SSEA-4 positive (undifferentiated) cell population, while only 5% of cells on feeders were positive, suggesting that transfection efficiency is significantly increased by using feeder-free conditions. Panel B shows transfection efficiencies of a GFP reporter plasmid using different conditions of Upofectamine 2000™ (L) or FuGENE™ (F).

FIG. 11 shows features of a human cell line capable of producing conditioned medium that supports hES cells in feeder-free culture. Panel A is a copy of a phase contrast micrograph, showing that the HEF1 cell line has morphological characteristics of fibroblasts. Panel B (below) is a copy of the results of a TRAP assay, showing that HEF1 cells transduced with a retroviral vector for telomerase reverse transcriptase (hTERT) acquired telomerase activity.

Figure 12:
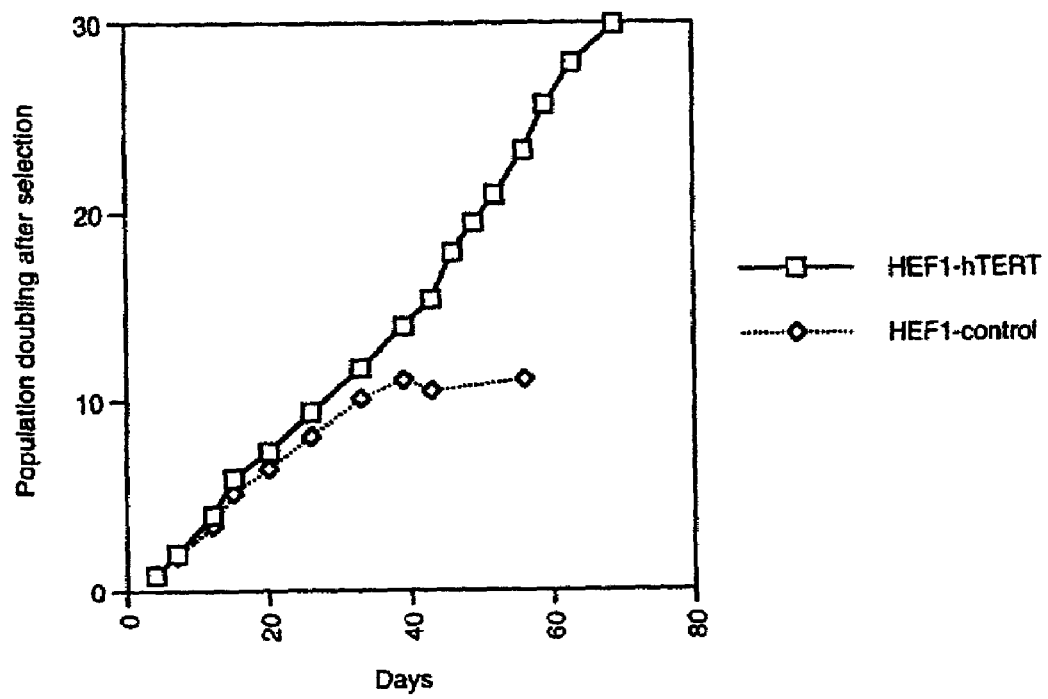

FIG. 12 is a graph showing growth of hTERT-transduced HEF1 cells, and cells transduced with vector control. Both lines initially doubled about once every 2 days. However, the control cells stopped proliferating at 38 days, while the hTERT-transfected cells continued proliferating over 60 days at a consistent growth rate.

FIG. 13 is a micrograph of the hTERT transduced cells and control cells, after staining for senescence-associated β-galactosidase, a known biomarker for cellular aging. Transfection with hTERT extends the life-span of the cell line and forestalls senescence.

Figure 14:
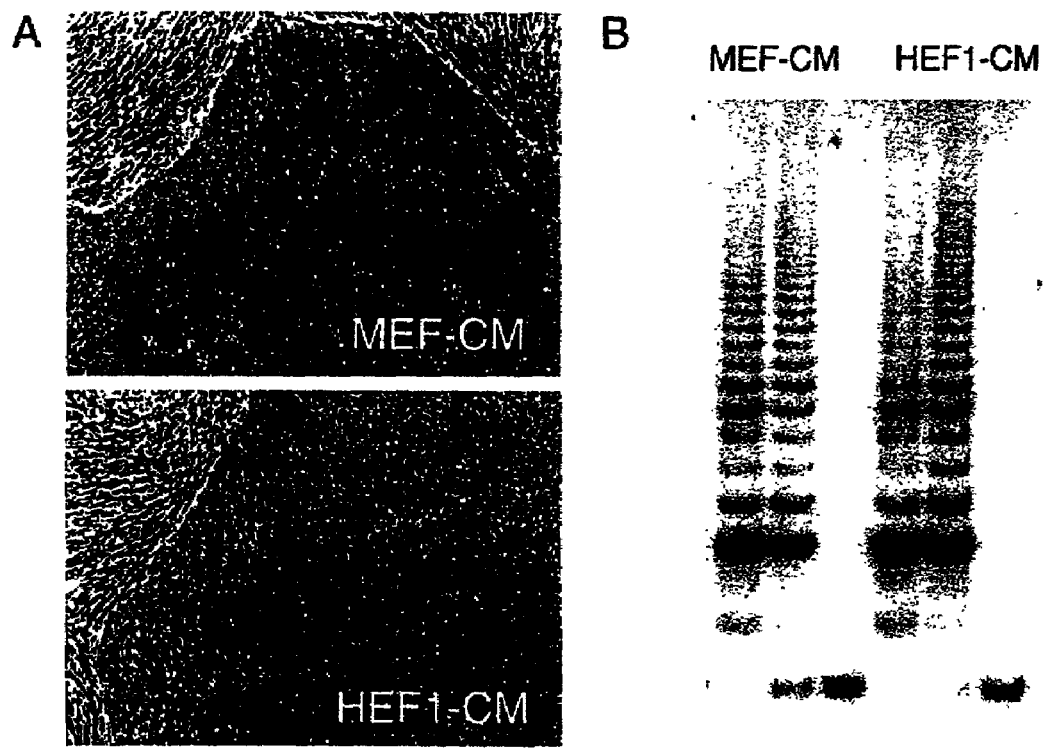

FIG. 14 shows colonies of hES cells after passaging into conditioned medium. Panel A is a copy of a light micrograph, showing undifferentiated colonies in cultures of hES cells maintained in medium conditioned by primary mouse embryonic fibroblasts (mEF), or by the human fibroblast-like cell line HEF1. Panel B (right) is a copy of the results of a TRAP, showing that hES cells maintained using HEF1 conditioned medium show telomerase activity characteristic of undifferentiated cells.

DETAILED DESCRIPTION

This disclosure provides a system for growing primate pluripotent stem (pPS) cells in vitro without requiring a layer of feeder cells to inhibit differentiation.

It has been found that the role of the feeder cells can be replaced by features in the culture environment that support proliferation of the cells without differentiation. One such feature is a suitable substrate on the culture surface, such as extracellular matrix exemplified by Matrigel® and laminin. Another feature is the use of culture media containing factors that in some way effectively inhibit differentiation, exemplified by conditioned media. Cells for conditioning media to support pPS cells include primary embryonic fibroblasts, telomerized fibroblasts, and fibroblast-like cells differentiated and selected from cultured pPS cells.

In an exemplary preparation, undifferentiated hES colonies were harvested from hES cultures on feeders, and then seeded onto a Matrigel® substrate in conditioned medium at approximately 15 colonies to each 9.6 cm² well. The day after seeding, undifferentiated hES cells were visible as small colonies of about 100–2,000 cells, and there were single cells in-between the colonies that appeared to be differentiating or dying. As the hES cells proliferated, colonies became large and compact, representing the majority of surface area of the culture dish. Near confluence, most of the cells had morphological characteristics of undifferentiated cells, and differentiated cells in between the colonies represented less than 10% of the cells in the culture.

Doubling rate was of the order of 20–40 hours, which is comparable to hES grown on feeder cells. Medium was changed daily, and the cells were split and passaged every 6 or 7 days. Nineteen days after initial seeding, the cells were tested for cell surface phenotype by immunofluorescence. Over 90% of the cells stained positively for SSEA-4 and Tra-1-60; over 80% stained positively for Tra-1-81, but less than 15% stained positively for SSEA-1. This indicates that at least ~80% of the cells in the preparation had the phenotype expected for undifferentiated hES cells.

It has also been discovered that feeder cells can be immortalized and maintained in long-term culture without causing them to lose the ability to produce high quality conditioned medium. For example, primary mouse embryonic fibroblasts can be immortalized by genetically altering them to express telomerase reverse transcriptase (Example 8). It has also been discovered that human cells suitable for conditioning medium can be obtained by differentiating embryonic stem cells in vitro. hES cells were differentiated by forming embryoid bodies in suspension, and then culturing in such a manner such that a homogeneous population of fibroblast-like cells is obtained (Examples 12 and 13).

Both the untransduced and the telomerized hEF cell lines proliferated in continual cell culture, and were used to produce conditioned medium. Cultures of hES cells grown in the medium were found to form colonies with morphology characteristic of undifferentiated hES cells, indistinguishable from hES cells grown directly on a layer of primary mEF feeders (FIG. 14, Panel A). This is important, because it obviates the need to repeatedly prepare primary feeder cultures to continue the culture, allowing pPS cells to be produced on a commercial scale of consistently high quality.

Culturing pPS cells in an environment free of feeder cells has a number of important advantages. For example:

Production of pPS cells and their derivatives is more easily scalable to commercial production. There is no need to produce feeder cells on an ongoing basis to support the culture, and passaging of the cells can be done mechanically.

Differentiation of the cells into committed precursors or terminally differentiated cells is facilitated in feeder-free culture. Embryoid bodies formed from feeder-free culture produce a more consistent cell population. Alternatively, direct differentiation can be performed by plating feeder-free stem cells directly onto a suitable solid-phase support. Depending on the conditions cell populations that are remarkably homogeneous can be obtained.

Being able to produce pPS cells without feeders and using human cells to condition the medium is attractive from the perspective of regulatory scrutiny—the pPS cells contain no xenogeneic components and no components of cancerous origin from other cells in the culture.

Screening of pharmaceuticals, toxins, or potential modulators of differentiation is also facilitated. Substances can be added to the culture medium without a collateral effect on feeder cells used to support the culture.

High quality mRNA and cDNA libraries can be produced easily using feeder-free pPS cell cultures. The yield of mRNA per $cm^2$ culture area is higher. The library will not be contaminated by transcripts from the feeder cells (cDNA of a different species, or different human genotype), and the expression pattern may reflect as much as 90% undifferentiated pPS cell phenotype. Subtraction libraries can also be obtained that are enriched for full-length cDNA of genes modulated during development.

Genetic transfection of feeder-free cultures facilitates selection of transfected cells by drug resistance markers, and gives much higher levels of transient expression. Methods have been discovered for genetically altering pPS cells without causing them to differentiate, either on drug-resistant feeders, or in feeder-free culture. The feeder-free system has the additional advantage of improving the efficiency of transfection. In model experiments, ~15% of cells in feeder-free culture have been transfected with a marker gene, whereas the transfection efficiency on primary feeder layers is typically only 5% of undifferentiated hES cells transfected on primary feeder layers were positive, indicating that transfection efficiency is significantly enhanced using feeder-free culture conditions.

The techniques provided in this invention represent an important advance in the potential use of pluripotent stem cells for research and therapeutic use. Further advantages of the invention will be understood from the sections that follow.

DEFINITIONS

Prototype "primate Pluripotent Stem cells" (pPS cells) are pluripotent cells derived from pre-embryonic, embryonic, or fetal tissue at any time after fertilization, and have the characteristic of being capable under the right conditions of producing progeny of several different cell types. pPS cells are capable of producing progeny that are derivatives of each of the three germinal layers: endoderm, mesoderm, and ectoderm, according to a standard art-accepted test, such as the ability to form a teratoma in a suitable host.

Included in the definition of pPS cells are embryonic cells of various types, exemplified by human embryonic stem (hES) cells, as described by Thomson et al. (Science 282: 1145, 1998); embryonic stem cells from other primates, such as Rhesus or marmoset stem cells described by Thomson et al. (Proc. Natl. Acad. Sci. USA 92:7844, 1995; Developmental Biology 38:133, 1998); and human embryonic germ (hEG) cells, described in Shamblott et al. (Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. For many embodiments of the invention, it is beneficial to use pPS cells that are karyotypically normal and not derived from a malignant source.

pPS cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated pPS cells, and may contain at least 40%, 60%, or 80% in order of increasing preference (in terms percentage of cells with the same genotype that are undifferentiated). Using the methods described in this disclosure, it is sometimes possible to develop or passage cultures that contain a relatively low proportion of differentiated pPS cells (even as low as 5 r 10%) into cultures that are substantially undifferentiated.

Whenever a culture or cell population is referred to in this disclosure as proliferating "without differentiation", what is meant is that after proliferation, the composition is substantially undifferentiated according to the preceding definition. Populations that proliferate through at least four passages (~20 doublings) without differentiation will contain substantially the same proportion of undifferentiated cells (or possibly a higher proportion of undifferentiated cells) when evaluated at the same degree of confluence as the originating culture.

"Feeder cells" or "feeders" are cells of one type that are co-cultured with cells of another type, to provide an environment in which the cells of the second type can grow. The feeder cells are optionally from a different species as the cells they are supporting. For example, certain types of pPS cells can be supported by primary cultures of mouse embryonic fibroblasts, immortalized mouse embryonic fibroblasts, or human fibroblast-like cells differentiated from hES cells, as described later in this disclosure. In coculture with pPS cells, feeder cells are typically inactivated by irradiation or treatment with an anti-mitotic agent such as mitomycin c, to prevent them from outgrowing the cells they are supporting. For use in producing conditioned medium, inactivation of the cells may be optional, and depends in part on mechanical aspects of medium production.

pPS cell populations are said to be "essentially free" of feeder cells if the cells have been grown through at east one round after splitting in which fresh feeder cells are not added to support the growth of the pPS. It is recognized that if a previous culture containing feeder cells is used as a source of pPS for the culture to which fresh feeders are not added, there will be some feeder cells that survive the passage. For example, hES cells are often cultured in a 9.6 cm² well on a surface of ~375,000 primary irradiated embryonic fibroblasts near confluence. By the end of the culture, perhaps 150,000 feeder cells are still viable, and will be split and passaged along with hES that have proliferated to a number of ~1 to 1.5 million. After a 1:6 split, the hES cells generally resume proliferation, but the fibroblasts will not grow and only a small proportion will be viable by the end of ~6 days of culture. This culture is essentially free of feeder cells, with compositions containing less than about 5% feeder cells. Compositions containing less than 1%, 0.2%, 0.05%, or 0.01% feeder cells (expressed as % of total cells in the culture) are increasingly more preferred.

Whenever a culture or cell population is referred to in this disclosure as "feeder-free", what is meant is that the composition is essentially free of feeder cells according to the preceding definition, subject only to further constraints if explicitly required.

A "growth environment" is an environment in which cells of interest will proliferate in vitro. Features of the environment include the medium in which the cells are cultured, the temperature, the partial pressure of $O_2$ and $O_2$, and a supporting structure (such as a substrate on a solid surface) if present.

A "nutrient medium" is a medium for culturing cells containing nutrients that promote proliferation. The nutrient medium may contain any of the following in an appropriate combination: isotonic saline, buffer, amino acids, antibiotics, serum or serum replacement, and exogenously added factors. A "conditioned medium" is prepared by culturing a first population of cells in a medium, and then harvesting the medium. The conditioned medium (along with anything secreted into the medium by the cells) may then be used to support the growth of a second population of cells.

"Restricted developmental lineage cells" are cells derived from embryonic tissue, typically by differentiation or partial differentiation of pPS cells. These cells are capable of proliferating and differentiating into several different cell types, but the range of their repertory is restricted. Examples are hematopoietic cells, which are pluripotent for blood cell types, and hepatocyte progenitors, which are pluripotent for sinusoidal endothelial cells, hepatocytes, and potentially other liver cells. Another example is neural restricted cells, which can generate glial cell precursors that progress to oligodendrocytes and astrocytes, and neuronal precursors that progress to neurons.

The term "polynucleotide" refers to a polymeric form of nucleotides of any length. Included are genes and gene fragments, mRNA, tRNA, rRNA, ribozymes, cDNA, recombinant polynucleotides, branched polynucleotides, plasmids, vectors, isolated DNA and RNA, nucleic acid probes, and primers. As used in this disclosure, the term polynucleotides refers interchangeably to double- and single-stranded molecules. Unless otherwise specified or required, any embodiment of the invention that is a polynucleotide encompasses both a double-stranded form, and each of the two complementary single-stranded forms known or predicted to make up the double-stranded form.

When comparison is made between polynucleotides for degree of identity, it is implicitly understood that complementary strands are easily generated, and the sense or antisense strand is selected or predicted that maximizes the degree of identity between the polynucleotides being compared. Percentage of sequence identity is calculated by first aligning the polynucleotide being examined with the reference counterpart, and then counting the number of residues shared between the sequences being compared as a percentage of the region under examination, without penalty for the presence of obvious insertions or deletions.

A "control element" or "control sequence" is a nucleotide sequence involved in an interaction of molecules that contributes to the functional regulation of a polynucleotide, such as replication, duplication, transcription, splicing, translation, or degradation of the polynucleotide. Transcriptional control elements include promoters and enhancers.

Genetic elements are "operatively linked" if they are in a structural relationship permitting them to operate in a manner according to their expected function. For instance, a promoter is operatively linked to a coding region if the promoter helps initiate transcription of the coding sequence. There may be intervening sequence between the promoter and coding region so long as this functional relationship is maintained.

A "cloning vector" is a polynucleotide vehicle (such as a plasmid, bacteriophage, or plant or animal virus) that permits replication of a sequence inserted into the vehicle in a host cell. In the case of a cDNA library, the replicated vectors contain heterogeneous polynucleotide inserts copied from a heterogeneous mRNA preparation transcribed from a plurality of genes. If the inserts are operatively linked to a transcriptional regulatory control element that permit expression of the insert at the protein or mRNA level in a host cell, the vehicle can also referred to as an "expression vector".

The terms "polypeptide", "peptide" and "protein" are used interchangeably in this disclosure to refer to polymers of amino acids of any length. The polymer may comprise modified amino acids, it may be linear or branched, and it may be interrupted by non-amino acids. Percentage of sequence identity is calculated for polypeptides by first aligning the polypeptide being examined with the reference counterpart or prototype, and then counting the number of residues shared between the sequences being compared as a percentage of the region under examination, without penalty for the presence of insertions or deletions. Where substitutions are made, conservative substitutions (in which one amino acid is substituted by another with similar charge, size, hydrophobicity, or aromaticity) are typically better tolerated. Desirable sequences preserve the function of the prototype: for example, the enzymatic activity, the binding of specific substrates, and the binding of specific antibody as detectable in a standard competition inhibition immunoassay.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. Also included are genetic alterations by any means that result in functionally altering or abolishing the action of an endogenous gene.

The genetic alteration is said to be "inheritable" if progeny of the altered cell has the same alteration. Determination of whether the genetic alteration is inheritable can be made by detecting presence of the polynucleotide template (e.g., by PCR amplification), or by detecting a phenotypic feature (such as expression of a gene product or effect thereof) that depends on the genetic alteration to be manifest.

The genetic alteration is said to be "stable" if it is inheritable through at least 4 rounds of cell replication, detectable as the presence of the polynucleotide template in a $7^{th}$ generation cell. Expression of a phenotype (at the mRNA, protein, or functional level) is said to be "stable" if the phenotypic feature in the $7^{th}$ generation cell is at least 10% (and often at least 50%) of that in the parental genetically altered cell. Stable expression indicates that the genetic alteration is also stable. The genetic alteration is said to be "transient" if the polynucleotide template is absent from progeny of the original genetically altered cell by the $7^{th}$ cell division. Expression of a phenotype is said to be "transient" if the phenotypic feature in the $7^{th}$ generation cell is no more than 5% of that in the original genetically altered cell, whether due to loss of the template or because of some mechanism inhibiting expression of the template.

A "cell line" is a population of cells that can be propagated in culture through at least 10 passages. The population can be phenotypically homogeneous, or the population can be a mixture of measurably different phenotypes. Characteristics of the cell line are those characteristics of the population as a whole that are essentially unaltered after 10 passages.

A cell is described as "telomerized" if it has been genetically altered with a nucleic acid encoding a telomerase reverse transcriptase (TERT) of any species in such a manner that the TERT is transcribed and translated in the cell. The term also applies to progeny of the originally altered cell that have inherited the ability to express the TERT encoding region at an elevated level. The TERT encoding sequence is typically taken or adapted from a mammalian TERT gene, exemplified by human and mouse TERT, as indicated below.

A cell line is described as "permanent" or "immortalized" if it has at least one of the following properties: 1) it has been genetically altered for elevated expression of telomerase reverse transcriptase (TERT), detectable, for example, as increased telomerase activity in TRAP assay; 2) for cell lines otherwise capable of no more than 15 population doublings, it has been genetically altered to extend its replicative capacity under suitable culture conditions to at least 20 population doublings; or 3) for cell lines otherwise capable of more than 15 population doublings, it has been genetically altered to significantly extend the replicative capacity of the cell line under typical culture conditions. It is understood that cells meeting this definition include not only the original genetically altered cells, but also all progeny of such cells that meet the listed criteria.

The term "antibody" as used in this disclosure refers to both polyclonal and monoclonal antibody. The ambit of the term deliberately encompasses not only intact immunoglobulin molecules, but also fragments and derivatives of immunoglobulin molecules (such as single chain Fv constructs), and fragments and derivatives of immunoglobulin equivalents such as T-cell receptors, as may be prepared by techniques known in the art, and retaining the desired antigen binding specificity.

GENERAL TECHNIQUES

For further elaboration of general techniques useful in the practice of this invention, the practitioner can refer to standard textbooks and reviews in cell biology, tissue culture, and embryology. Included are *Teratocarcinomas and embryonic stem cells: A practical approach* (E. J. Robertson, ed., IRL Press Ltd. 1987); *Guide to Techniques in Mouse Development* (P. M. Wasserman et al., eds., Academic Press 1993); *Embryonic Stem Cell Differentiation in Vitro* (M. V. Wiles, Meth. Enzymol. 225:900, 1993); *Properties and uses of Embryonic Stem Cells: Prospects for Application to Human Biology and Gene Therapy* (P. D. Rathjen et al., al., 1993). Differentiation of stem cells is reviewed in Robertson, Meth. Cell Biol. 75:173, 1997; and Pedersen, Reprod. Fertil. Dev. 10:31, 1998.

Methods in molecular genetics and genetic engineering are described generally in the current editions of *Molecular Cloning: A Laboratory Manual*, (Sambrook et al.); *Oligonucleotide Synthesis* (M. J. Gait, ed.,); *Animal Cell Culture* (R. I. Freshney, ed.); *Gene Transfer Vectors for Mammalian Cells* (Miller & Calos, eds.); *Current Protocols in Molecular Biology* and *Short Protocols in Molecular Biology*, 3rd Edition (F. M. Ausubel et al., eds.); and *Recombinant DNA Methodology* (R. Wu ed., Academic Press). Reagents, cloning vectors, and kits for genetic manipulation referred to in this disclosure are available from commercial vendors such as BioRad, Stratagene, Invitrogen, and ClonTech.

For general techniques involved in preparation of mRNA and cDNA libraries and their analysis, those skilled in the art have access to *RNA Methodologies: A Laboratory Guide for Isolation and Characterization* (R. E. Farrell, Academic Press, 1998); *cDNA Library Protocols* (Cowell & Austin, eds., Humana Press); *Functional Genomics* (Hunt & Uvesey, eds., 2000); and the *Annual Review of Genomics and Human Genetics* (E Lander, ed., published yearly by Annual Reviews). Techniques can also be inferred from descriptions of other expression libraries, for example: *Developmental Embryonic Mouse Libraries* (U.S. Pat. No. 5,789,158); *Method for Generating a Subtracted cDNA Library* (U.S. Pat. No. 5,643,761); *Comparative Gene Transcript Analysis* (WO 95/20681, Incyte Pharmaceuticals); *A Gene Trap Approach in Mouse Embryonic Stem Cells* (Skames et al., Genes Dev. 6:903, 1992); Sasaki et al., Genomics 49:167, 1998; Adjaye et al., Genomics 46:337, 1997; Nishiguchi et al., J. Biochem. 119:749, 1996; and Phillips et al., Science 288:1635, 2000.

General techniques used in raising, purifying and modifying antibodies, and the design and execution of immunoassays including immunocytochemistry, the reader is referred to *Handbook of Experimental Immunology* (Weir & Blackwell, eds.); *Current Protocols in Immunology* (Coligan et al., eds.); and *Methods of Immunological Analysis* (Masseyeff et al., eds., Weinheim: VCH Verlags GmbH).

General techniques in cell culture and media collection are outlined in *Large Scale Mammalian Cell Culture* (Hu et al., Curr. Opin. Biotechnol. 8:148, 1997); *Serum-free Media* (K. Kitano, Biotechnology 17:73, 1991); *Large Scale Mammalian Cell Culture* (Curr. Opin. Biotechnol. 2:375, 1991); and *Suspension Culture of Mammalian Cells* (Birch et al., Bioprocess Technol. 19:251, 1990). Other reading of interest includes *Understanding Media*. (M. McLuhan, Mentor N.Y., 1964) and *The Medium is the Massage* (M. McLuhan & O. Fiore, Bantam N.Y., 1967).

SOURCES OF PLURIPOTENT STEM CELLS

Suitable source cells for culturing and differentiation according to this invention include established lines of pluripotent cells derived from tissue formed after gestation. Exemplary primary tissue sources are embryonic tissue (such as a blastocyst), or fetal tissue taken any time during gestation, typically but not necessarily before 10 weeks gestation. Non-limiting exemplars are established lines of primate embryonic stem (ES) and embryonic germ (EG) cells. Also contemplated is use of the techniques of this disclosure during the initial establishment or stabilization of such cells, in which case the source cells would be primary pluripotent cells taken directly from the tissues listed.

Media and Feeder Cells

Media for isolating and propagating pPS cells can have any of several different formulas, as long as the cells obtained have the desired characteristics, and can be propagated further. Suitable sources are as follows: Dulbecco's modified Eagles medium (DMEM), Gibco # 11965-092; Knockout Dulbecco's modified Eagles medium (KO DMEM), Gibco # 10829-018; 200 mM L-glutamine, Gibco # 15039-027; non-essential amino acid solution, Gibco 11140-050; β-mercaptoethanol, Sigma # M7522; human recombinant basic fibroblast growth factor (bFGF), Gibco # 13256-029. Exemplary serum-containing ES medium is made with 80% DMEM (typically KO DMEM), 20% defined fetal bovine serum (FBS) not heat inactivated, 0.1 mM non-essential amino acids, 1 mM L-glutamine, and 0.1 mM β-mercaptoethanol. The medium is filtered and stored at 4° C. for no longer than 2 weeks. Serum-free ES medium is made with 80% KO DMEM, 20% serum replacement, 0.1 mM non-essential amino acids, 1 mM L-glutamine, and 0.1 mM β-mercaptoethanol. Not all serum replacements work; an effective serum replacement is Gibco # 10828-028 (proprietary formula; product obtainable from the manufacturer). The medium is filtered and stored at 4° C. for no longer than 2 weeks. Just before use, human bFGF is added to a final concentration of 4 ng/mL.

pPS cells are typically cultured on a layer of feeder cells that support the pPS cells in various ways, such as the production of soluble factors that promote pPS cell survival or proliferation, or inhibit differentiation. Feeder cells are typically fibroblast type cells, often derived from embryonic or fetal tissue. A frequently used source is mouse embryo. Useful feeder cell lines have been obtained by obtaining embryonic fibroblasts, transfecting them to express telomerase, and then passaging them or freezing them for future use. The cell lines are plated to near confluence, irradiated to prevent proliferation, and used to support pPS cell cultures.

In one illustration, pPS cells are first derived and supported on primary embryonic fibroblasts. Mouse embryonic fibroblasts (mEF) can be obtained from outbred CF1 mice (SASCO) or other suitable strains. The abdomen of a mouse at 13 days of pregnancy is swabbed with 70% ethanol, and the decidua is removed into phosphate buffered saline (PBS). Embryos are harvested; placenta, membranes, and soft tissues are removed; and the carcasses are washed twice in PBS. They are then transferred to fresh 10 cm bacterial dishes containing 2 mL trypsin/EDTA, and finely minced. After incubating 5 min at 37° C., the trypsin is inactivated with 5 mL DMEM containing 10% FBS, and the mixture is transferred to a 15 mL conical tube. Debris is allowed to settle for 2 min, the supernatant is made up to a final volume of 10 mL, and plated onto a 10 cm tissue culture plate or T75 flask. The flask is incubated undisturbed for 24 h, after which the medium is replaced. When flasks are confluent (~2–3 d), they are split 1:2 into new flasks.

Feeder cells are propagated in mEF medium, containing 90% DMEM (Gibco # 11965-092), 10% FBS (Hyclone # 30071-03), and 2 mM glutamine. mEFs are propagated in T150 flasks (Corning # 430825), splitting the cells 1:2 every other day with trypsin, keeping the cells subconfluent. To prepare the feeder cell layer, cells are irradiated at a dose to inhibit proliferation but permit synthesis of important factors that support hES cells (~4000 rads gamma irradiation). Six-well culture plates (such as Falcon # 304) are coated by incubation at 37° C. with 1 mL 0.5% gelatin per well overnight, and plated with 375,000 irradiated mEFs per well. Feeder cell layers are used 5 h to 4 days after plating. The medium is replaced with fresh hES medium just before seeding pPS cells.

Preparation of Human Embryonic Stem (hES) Cells

Human embryonic stem (hES) cells can be prepared as described by Thomson et al. (U.S. Pat. No. 5,843,780; Science 282:1145, 1998; Curr. Top. Dev. Biol. 38:133 ff., 1998; Proc. Natl. Acad. Sci. USA 92:7844, 1995).

Briefly, human blastocysts are obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for ES cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 min (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh ES medium, and observed for colony formation. Colonies demonstrating undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1–2 weeks by brief trypsinization, exposure to Dulbecco's PBS (without calcium or magnesium and with 2 mM EDTA), exposure to type IV collagenase (~200 U/mL; Gibco) or by selection of individual colonies by micropipette. Clump sizes of about 50 to 100 cells are optimal.

Preparation of Human Embryonic Germ (hEG) Cells

Human Embryonic Germ (hEG) cells can be prepared from primordial germ cells present in human fetal material taken about 8–11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 mm³ chunks. The tissue is then pipetted through a 100 µL tip to further disaggregate the cells. It is incubated at 37° C. for ~5 min, then ~3.5 mL EG growth medium is added. EG growth medium is DMEM, 4500 mg/L D-glucose, 2200 mg/L mM sodium bicarbonate;

15% ES qualified fetal calf serum (BRL); 2 mM glutamine (BRL); 1 mM sodium pyruvate (BRL); 1000–2000 U/mL human recombinant leukemia inhibitory factor (LIF, Genzyme); 1–2 ng/ml human recombinant basic fibroblast growth factor (bFGF, Genzyme); and 10 µM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced and incubated 1 h or overnight at 37° C., resuspended in 1–3 mL of EG growth medium, and plated onto a feeder layer.

Ninety-six well tissue culture plates are prepared with a sub-confluent layer of feeder cells cultured for 3 days in modified EG growth medium free of LIF, bFGF or forskolin, inactivated with 5000 rad γy-irradiation. Suitable feeders are STO cells (ATCC Accession No. CRL 1503). ~0.2 mL of primary germ cell (PGC) suspension is added to each of the wells. The first passage is conducted after 7–10 days in EG growth medium, transferring each well to one well of a 24-well culture dish previously prepared with irradiated STO mouse fibroblasts. The cells are cultured with daily replacement of medium until cell morphology consistent with EG cells are observed, typically after 7–30 days or 1–4 passages.

Propagation of pPS Cells in the Absence of Feeder Cells pPS cells can be propagated continuously in culture, using a combination of culture conditions that support proliferation without promoting differentiation. It has been determined that hES cells can be grown without differentiation, even in the absence of feeder cells. For feeder-free culture, it is beneficial to provide a compatible culture surface (the substrate), and a nutrient medium that supplies some of the influences provided by the feeder cells.

Particularly suitable as a substrate for feeder-free pPS culture are extracellular matrix components (derived from basement membrane, or forming part of adhesion molecule receptor-ligand couplings). A commercial preparation is available from Becton Dickenson under the name Matrigel®, and can be obtained in regular or Growth Factor Reduced formulation. Both formulations are effective. Matrigel® is a soluble preparation from Engelbreth-Holm-Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations. Laminins are major components of all basal laminae in vertebrates, which interact with integrin heterodimers such as α6β1 and α6β4 (specific for laminins) and other heterodimers (that cross-react with other matrices). Using culture conditions illustrated in the examples, collagen IV supports hES cell growth, while collagen I does not. Substrates that can be tested using the experimental procedures described herein include not only other extracellular matrix components, but also polyamines (such as poly-ornithine, poly-lysine), and other commercially available coatings.

The pluripotent cells are plated onto the substrate in a suitable distribution and in the presence of a medium that promotes cell survival, propagation, and retention of the desirable characteristics. These characteristics benefit from careful attention to the seeding distribution. One feature of the distribution is the plating density. It has been found that plating densities of at least ~15,000 cells cm$^{-2}$ promote survival and limit differentiation. Typically, a plating density of between about 90,000 cm$^{-2}$ and about 170,000 cm$^{-2}$ is used.

Another feature is the dispersion of cells. The propagation of mouse stem cells involves dispersing the cells into a single-cell suspension (Robinson, Meth. Mol. Biol. 75:173, 1997 at page 177). In contrast, passaging primate PS cells has previously thought to require keeping the cells together in small clusters. Enzymatic digestion is halted before cells become completely dispersed (say, ~5 min with collagenase IV). The plate is then scraped gently with a pipette, and the cells are triturated with the pipette until they are suspended as clumps of adherent cells, about 10–2000 cells in size. The clumps are then plated directly onto the substrate without further dispersal.

It has now been discovered that primate PS cells can be passaged between feeder-free cultures as a finer cell suspension, providing that an appropriate enzyme and medium are chosen, and the plating density is sufficiently high. By way of illustration, confluent human embryonic stem cells cultured in the absence of feeders are removed from the plates by incubating with a solution of 0.05% (wt/vol) trypsin (Gibco) and 0.053 mM EDTA for 5–15 min at 37° C. With the use of pipette, the remaining cells in the plate are removed and the cells are triturated with the pipette until the cells are dispersed into a suspension comprising single cells and some small clusters. The cells are then plated at densities of 50,000–200,000 cells/cm$^2$ to promote survival and limit differentiation. The phenotype of ES cells passaged by this technique is similar to what is observed when cells are harvested as clusters by collagen digestion. As another option, the cells can be harvested without enzymes before the plate reaches confluence. The cells are incubated ~5 min in a solution of 0.5 mM EDTA alone in PBS, washed from the culture vessel, and then plated into a new culture without further dispersal.

pPS cells plated in the absence of fresh feeder cells benefit from being cultured in a nutrient medium. The medium will generally contain the usual components to enhance cell survival, including isotonic buffer, essential minerals, and either serum or a serum replacement of some kind. The medium can be conditioned by culturing with another cell population, or it can comprise a synthetic mixture of factors that promote growth of the hPS cells while inhibiting differentiation.

Conditioned medium can be prepared by culturing irradiated primary mouse embryonic fibroblasts (or another suitable cell preparation) at a density of ~5–6×10$^4$ cm$^{-2}$ in a serum free medium such as KO DMEM supplemented with 20% serum replacement and 4 ng/mL basic fibroblast growth factor (bFGF). The culture supernatant is harvested after ~1 day at 37° C. Devices for growing anchorage-dependent cells include T-flasks, roller bottles, gas-permeable bags, hollow fiber bioreactors, flat-bed bioreactors, and parallel plate bioreactors. If the cells are mobilized in a three-dimensional matrix, they can be cultured in continuous stirred tank bioreactors or air-lift bioreactors.

As illustrated in the examples below, medium that has been conditioned for 1–2 days is typically used to support pPS cell culture for 1–2 days, and then exchanged. The medium can be used directly after conditioning, it can be stored neat or as an extract (e.g., for 2, 6, or 14 days at 4° C., or frozen at −20° C.). Caution should be taken in filtering the medium: some filters such as cellulose acetate 20 µ non-protein binding membranes (Corning # 430769) can be suitable where others remove activity. In initial studies, medium is typically used undiluted. Efficacy of dilutions and other manipulations can be assessed by maintaining pPS cells with the medium for 7 days or longer, and determining whether the cultures maintain features characteristic of undifferentiated pPS cells.

If desired, conditioned medium can be supplemented before use with additional growth factors that benefit pPS cell culture. For hES, a growth factor like bFGF or FGF-4 is often used. For hEG, culture medium may be supplemented with a growth factor like bFGF, an inducer of gp130, such as LIF or Oncostatin-M, and perhaps a factor that elevates cyclic AMP levels, such as forskolin. Other types of pPS cells may benefit from other factors in the medium, such as stem cell factor (Steel factor, c-kit ligartd), or IL-6. It is often beneficial to add growth factors such as bFGF or FGF-4 to the medium both before conditioning, and then again before using the medium to support the growth of pPS cells. It is recognized that the beneficial effects of fibroblast conditioned medium are derived from soluble factors produced by the embryonic fibroblasts, and that synthetic mixtures having similar components in various combinations may also be beneficial.

It should be recognized that each of the conditions described here can be optimized independently, and certain combinations of conditions will prove effective upon further testing. Such optimization is a matter of routine experimentation, and does not depart from the spirit of the invention provided in this disclosure.

Cell Lines Suitable for Conditioning Media

As an alternative to primary mouse fibroblast cultures, conditioned medium can be prepared from other cell types. Exemplary are telomerized embryonic fibroblast cell lines, and differentiated pPS cells with the morphological features of fibroblasts.

Exemplary Non-human Cell Lines for Conditioning Media

Feeder cells typically contain fibroblast type cells. Primary embryonic or fetal feeder cell cultures are a mixed population of cells, containing cells that have morphology of fibroblasts and of early muscle and neuronal cells. Different cells in the population may play different roles in supporting pPS culture, and the distribution and character of the culture may change.

More permanent feeder cell lines can be developed for producing medium according to this invention using embryonic fibroblasts from a non-human species such as a mouse (prepared as described earlier). The cells are genetically altered with an immortalizing gene, such as a gene that expresses telomerase. Procedures for telomerizing cells and testing for telomerase activity can be found later in this disclosure.

In addition, the cells used for conditioning medium can also be genetically altered to provide one or more additional features. For example, for screening purposes, cells can be provided with drug resistance genes for one or more antibiotics, such as neomycin, hygromycin, or puromycin (Example 8). Cells can be provided with marker genes, such as green fluorescent protein (Example 8), β-galactosidase, or certain cell-surface antigens (such as a truncated NGF receptor) that provide a tag for immunoisolation. Cells can also be provided with genes for the biosynthesis and secretion of factors that supplement the potency of the medium for supporting pPS culture. Exemplary is human basic fibroblast growth factor (bFGF), and other nutritional supplements listed in this disclosure.

To increase the replicative capacity of a cell line used for conditioning medium, they can be telomerized (or otherwise immortalized) as described elsewhere in this disclosure.

Exemplary Human Cell Lines for Conditioning Media

It has been discovered that cells with particular characteristics differentiated from human embryo derived cells can be used to support culture of undifferentiated pPS cells. Certain fibroblast-like cells (or mesenchymal cells) derived from human embryo cells have this property, and can be identified according to the assay described earlier.

An exemplary method for obtaining suitable cells involves differentiating a culture of pPS cells (such as hES cells). Differentiated cells with a particular phenotype are selected from amongst the mixed differentiated cell population, and medium conditioned by culturing with the selected cells is tested for its ability to support growth of pPS cells in a culture environment essentially free of feeder cells.

Differentiation of the pPS can be initiated by first forming aggregates, for example, by overgrowth of a donor pPS cell culture, or by culturing pPS cells in culture vessels having a substrate with low adhesion properties which allows embryoid bodies (EB) to form. Embryoid bodies can be made in suspension culture: undifferentiated pPS cells are harvested by brief collagenase digestion, dissociated into clusters, and plated in non-adherent cell culture plates. The aggregates are fed every few days, and then harvested after a suitable period, typically 4–8 days. The cells are then cultured in a medium and/or on a substrate that promotes enrichment of medium-conditioning cells. Alternatively, the cells can be obtained by direct differentiation of pPS cells by preparing a suspension of undifferentiated pPS cells, and then plating directly onto a substrate that promotes regulated differentiation into medium-conditioning cells. Suitable substrates include glass or plastic coverslips coated with a poly-cationic substance, such as poly-ornithine, or an extracellular matrix.

Once differentiated, the population can be enriched for medium-conditioning cells either according to markers they express (for example, by immunolabeling and fluorescence sorting, by sorting on magnetic beads, or by immune-specific lysis of contaminating cells).

It has been discovered that fibroblast-like cells differentiated from hES cells are especially appropriate for conditioning medium according to this invention. A fibroblast-like cell can be recognized by morphological criteria, particularly the stellate or spindle-shape of the cell with cytoplasmic processes that resemble those of fibroblasts found in connective tissue. Further confirmation of the fibroblast nature of a cell can be obtained by markers and secreted products of the cell, such as collagen matrix, collagenase, and various isotypes of fibroblast growth factor, particularly bFGF. These markers can be detected at the level of transcription or translation.

Differentiated pPS cells can then be tested according to the assay outlined above, to determine if they are suitable for conditioning medium in such a manner that the medium supports pPS cell growth in feeder-free culture.

Cell lines differentiated and selected from hES in this manner typically are capable of replicating in cell culture for at least about 30 days (Examples 12 and 13; FIG. 12). In some embodiments, the cells replicate 60 days or 120 days (~10 doublings, 25 doublings, or 50 doublings). High replicative capacity is in part because these cells are differentiated from stem cells that are practically immortal, and have telomeres of a length compatible with primary embryonic cells. These cells are often suitable for conditioning medium without further adaptation. If desired, the cells can also be genetically altered to express telomerase reverse transcriptase, or otherwise immortalized as described earlier. This forestalls senescence, and increases the replicative capacity beyond that of the unaltered cells, which facilitates commercial production of the medium and improves reproducibility between batches.

Optionally, differentiated human PS cells suitable for conditioning medium can be further adapted—for example, by genetically altering the cells to express a growth factor like bFGF, or to express TERT, or to immortalize the cells, as described in the previous section.

Testing Conditioned Medium and Cells for Producing it

Conditioned medium can be tested for its ability to support pPS cells by swapping it into a feeder-free culture system in place of medium conditioned by primary mouse embryonic fibroblasts (mEF), a proven standard. If pPS cells grow in a substantially undifferentiated state, then the conditioned medium can be characterized as supporting pPS cells in feeder free culture.

A convenient way to determine whether pPS cells are differentiating is to follow the morphological features of the colonies (described below). According to this assay method, conditioned medium will be considered capable of supporting growth of pPS cells if the proportion of undifferentiated pPS cells in a subconfluent culture (typically ~5 days after passaging) does not substantially decline through at least 4 passages in the conditioned medium (optionally supplemented with additional growth factors or otherwise processed as appropriate).

If desired, a quantitative readout of this assay can be obtained to estimate the quality or concentration of pPS cell supportive factors in the medium. In one example, basal medium is conditioned for various periods of time (say, 6 h, 12 h, 24 h, and 48 h), and the conditioned media are each tested for their ability to support feeder-free pPS cell culture for consecutive 24 h periods. Media rendered effective by briefer conditioning periods may be desired because of less processing time. In another example, basal medium conditioned for 24 h is tested by dilution analysis (diluting in basal medium, optionally supplemented with other nutrients) for its ability to support pPS culture. Media that are effective after greater dilution (for example, 1:1, 1:2, and 1:4 conditioned medium:diluent medium) may be desired for ease of storage. Choice of particular features will depend on the application.

Cell lines can be tested for their ability to produce conditioned medium by culturing the cells in a basal medium for an appropriate time, and then testing the medium for its ability to support feeder-free pPS cell cultures as described above. If the conditioned medium does not support feeder-free pPS cultures, the method of conditioning can be adjusted in various parameters, such as culture time, basal medium used, cell density, and possible post-culture processing of the medium or supplementation with additional additives. Adjustment of these and other parameters can be performed empirically, and as a matter of routine experimentation. A cell line will be considered to have passed the test if it produces conditioned medium that support feeder-free pPS cultures after routine optimization of any of the culture parameters during conditioning.

If desired, conditioned media and cells for producing them can be further evaluated based on other characteristics of the pPS cells they support, as described below.

Batch Production of Conditioned Media

A conditioned medium of this invention is produced by culturing cells in the medium, and then harvesting the conditioned medium from the cell culture.

The cells used for the conditioning have the ability to condition medium in a manner that gives it the capacity to support pPS cells in feeder-free form, as already described. The base medium used for conditioning can have any of several different formulae, depending in part on the types of cells used. The medium must be able to support culture of at least the cell line used for the conditioning of the medium. It is convenient that the medium also support culture of pPS after conditioning. However, as an alternative, the medium can be supplemented with other factors or otherwise processed after conditioning to adapt it for culturing the pPS cells.

For supporting pPS cells in feeder-free culture, suitable base media can be made from the following components: Dulbecco's modified Eagle's medium (DMEM), Gibco #11965-092; Knockout Dulbecco's modified Eagle's medium (KO DMEM), Gibco # 10829-018; Ham's F12/50% DMEM basal medium; 200 mM L-glutamine, Gibco # 15039-027; non-essential amino acid solution, Gibco 11140-050; β-mercaptoethanol, Sigma # M7522; human recombinant basic fibroblast growth factor (bFGF), Gibco # 13256-029. Exemplary serum-containing ES medium is made with 80% DMEM (typically KO DMEM), 20% defined fetal bovine serum (FBS) non heat inactivated, 0.1 mM non-essential amino acids, 1 mM L-glutamine, and 0.1 mM β-mercaptoethanol. The medium is filtered and stored at 4° C. for no longer than 2 weeks. Serum-free ES medium is made with 80% KO DMEM, 20% serum replacement, 0.1 mM non-essential amino acids, 1 mM L-glutamine, and 0.1 mM β-mercaptoethanol. Not all serum replacements work; an effective serum replacement is Gibco # 10828-028 (proprietary formula; product obtainable from the manufacturer). The medium is filtered and stored at 4° C. for no longer than 2 weeks. Just before combining with the cells used for conditioning, human bFGF can be added to a final concentration of 4 ng/mL.

The selected medium is then combined with the cells used for conditioning in an environment that allows the cells to release into the medium the components that support pPS cells. Optionally, the cells can be inactivated (i.e., rendered incapable of substantial replication) by radiation (e.g., ~4,000 rads), treatment with a chemical inactivator like mitomycin c, or by any other effective method. The inactivation of the cells may not be necessary in instances where the medium is separated from the conditioning cells before use in supporting pPS cell cultures.

The cells are cultured in the medium for sufficient time to allow adequate concentration of released factors that support pPS cell culture. Typically, medium conditioned by culturing for 24 h at 37° C. contains a concentration of factors that support pPS cell culture for 24 hours. However, the culturing period can be adjusted upwards or downwards, determining empiricaily (or by assaying for the concentration of essential factors) what constitutes an adequate period. After collecting a batch of conditioned medium, the cells can be used to condition a further batch of medium over a further culture period, for as many cycles as desired as long as the cells retain their ability to condition the medium in an adequate fashion. For example, fibroblast-like cells derived from differentiation of embryonic stem cells can be used to condition medium over 1-day periods for 1–2 weeks (Examples 12 and 13).

Selection of culture apparatus for conditioning medium can be made based on the scale and purpose of medium collection. In initial studies and for screening purposes, it is often convenient to produce cultured medium in standard culture flasks or multi-well plates. Initial scale-up can be done in larger vessels with multiple surfaces, such as Nunc cell factories. Large scale, automated, or GMP compliant production can involve the use of more specialized devices.

Continuous cell culture systems are reviewed by J. Furey (Genetic Eng. News 20:10, May 15, 2000). Perfusion culture involves removal of medium from the culture chamber, and replenishment with fresh medium. In the spin basket system, a basket-like device is attached to a drive shaft and covered by a porous screen through which medium can be exchanged. In the external filter perfusion system, a culture is circulated from a vessel, through a hollow-fiber filter module, and back to the vessel, with a pump attached to the loop to provide the circulation. A particular perfusion system, the ATF System (available commercially from Refine Technology, Edison N.J.) consists of a diaphragm pump on one end of a hollow-fiber housing, the other end of which is connected to a bioreactor. Alternating tangential flow through the fibers generates low shear laminar flow, which provides high flow rates, scalability, and adaptability to different bioreactors.

Large-scale culture systems are also available from Aastrom Sciences Inc., Ann Arbor Mich. The Aastrom Replicell™ System provides for expansion from small starting cell populations (Koller et al., Bone Marrow Transpl. 21:653, 1009; Koller et al., Blood 86:1784, 1995). Cellstasis® culture technology is marketed by Genespan Corp., Bothell Wash. Cells reside in extracapilliary spaces, and hollow fibers bring fresh media and oxygen into the culture environment (R. Lewis, Genetic Eng. News 18(9), May 1, 1998). Any other suitable device can be used with this invention. U.S. Pat. No. 4,501,815 describes a device for culturing differentiated cells. U.S. Pat. No. 4,296,205 describes cell culture and continuous dialysis flasks and their use. U.S. Pat. No. 5,994,129 describes a portable cassette for use in maintaining biological cells. U.S. Pat. No. 5,362,642 describes a containment system for storing, reconstituting, dispensing, and harvesting cell culture media. U.S. Pat. No. 6,022,742 describes a culture device and method.

A particular embodiment of this invention is a device adapted for preparing conditioned medium, having a culture chamber containing cells of this invention capable of conditioning medium, and an outlet port that is optionally sealable for withdrawing medium from the culture chamber after conditioning by the cells. The device may also have a mass-transfer microporous surface in the form of a plate, a hollow fiber, or other structure that partitions the cultured cells from medium that has been conditioned, which allows free passage of the medium, and which provides passage to the outlet port. The device may also have one or more ports for introducing fresh medium, introducing additional cells, or removing expired cells and cell debris. For continuous flow systems, a pump may be attached to the medium inlet or outlet port to provide circulation.

Following collection of the conditioned medium, it can be used to support pPS cell growth directly, if appropriate. If the medium is filtered, frozen, or otherwise processed for the first time using a new technique, it is worthwhile to test a small batch to determine if the activity is still present in the reconstituted medium.

In certain embodiments, the conditioned medium is supplemented before use with additional growth factors that benefit pPS cell culture. For hES, a growth factor like bFGF is often used. It has been found that the ability of the medium to support hES cells in feeder-free culture may benefit by adding bFGF both before and after the conditioning of the medium (Example 11). For hEG, culture medium may be supplemented with a growth factor like bFGF, an activator of gp 130, such as LIF, IL-6, or Oncostatin-M, and perhaps a factor that elevates cyclic AMP levels, such as forskolin or cholera toxin. Other types of pPS cells may benefit from other factors in the medium, such as stem cell factor (also known as Steel factor, c-kit ligand).

In certain embodiments, the conditioned medium is further processed. For example, it can be concentrated by salt precipitation or selective filtration, or it can be extracted to separate or store the effective components. Medium extracts can then be reconstituted or supplemented with fresh culture medium before use to support pPS cultures.

After preparation, the medium can be used to support pPS cells in feeder-free culture, as described earlier. It is also suitable for other purposes, and can be used for such purposes without restriction. For example, the medium can be added to pPS cultured in the presence of feeder cells, in order to further support the proliferation of the cells or limit differentiation. The medium can also be used to maintain or promote proliferation of other types of cultured precursor cells or terminally differentiated cells, as may be determined empirically.

Characteristics of pPS Cells Grown in the Absence of Feeder Cells

Human ES cells have the characteristic morphological features of undifferentiated stem cells. In the two dimensions of a standard microscopic image, hES cells have high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes. It is desirable to obtain cells that have a "normal karyotype", which means that the cells are euploid, wherein all human chromosomes are present and are not noticeably altered.

hES and hEG cells can also be characterized by expressed cell markers. In general, the tissue-specific markers discussed in this disclosure can be detected using a suitable immunological technique—such as flow cytometry for membrane-bound markers, immunocytochemistry for intracellular markers, and enzyme-linked immunoassay, for markers secreted into the medium. The expression of protein markers can also be detected at the mRNA level by reverse transcriptase-PCR using marker-specific primers. See U.S. Pat. No. 5,843,780 for further details.

Stage-specific embryonic antigens (SSEA) are characteristic of certain embryonic cell types. Antibodies for SSEA-1, SSEA-3 and SSEA-4 are available from the Developmental Studies Hybridoma Bank of the National Institute of Child Health and Human Development (Bethesda Md.). Other useful markers are detectable using antibodies designated Tra-1-60 and Tra-1-81 (Andrews et al., *Cell Lines from Human Germ Cell Tumors*, in E. J. Robertson, 1987, supra). Mouse ES cells can be used as a positive control for SSEA-1, and as a negative control for SSEA-4, Tra-1-60, and Tra-1-81. SSEA-4 is consistently present on human embryonal carcinoma (hEC) cells Differentiation of pPS cells in vitro results in the loss of SSEA-4, Tra-1-60, and Tra-1-81 expression and increased expression of SSEA-1. SSEA-1 is also found on hEG cells. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.). Expression of hTERT and OCT-4 (detectable by RT-PCR) and telomerase activity (detectable by TRAP assay) are also characteristic of many types of undifferentiated pPS cells (Example 3).

Another desirable feature of propagated pPS cells is a potential to differentiate into cells of all three germinal layers: endoderm, mesoderm, and ectoderm tissues. Pluripotency of hES cells can be confirmed by injecting approximately $3.0 \times 10^6$ cells into the rear leg muscles of 8–12 week old male SCID mice. The resulting tumors can be fixed in 4% paraformaldehyde and examined histologically after paraffin embedding at 8–16 weeks of development. Teratomas develop that demonstrate tissues of all three germ layers; for example cartilage, smooth muscle, or striated muscle (mesoderm); stratified squamous epithelium with hair follicles, neural tube with ventricular, intermediate, or mantle layers (ectoderm); and ciliated columnar epithelium and villi lined by absorptive enterocytes or mucus-secreting goblet cells (endoderm). Pluripotency of pPS cells can be further tested for differentiation into particular cell lines, according to procedures described later in this disclosure.

An exemplary preparation of hES cells grown in the absence of feeders is described below in Example 1. At 19 days of culture, >80% of the cells stained positively for SSEA-4, Tra-1 -60 and Tra-1 -81, while >15% of the cells stained positively for SSEA-1.

Certain cell populations described in this disclosure are substantially undifferentiated, and can be passaged between multiple cultures to which no new feeder cells are added. It is recognized that during certain passages, some cells may differentiate (particularly when replated as single cells at low density, or when large clusters are allowed to form). However, cultures typically reestablish a larger proportion of undifferentiated cells during the culture period. Of particular interest are cells that can be propagated in the feeder-free system for at least ~3 months. Optimally, the propagated cells will have a doubling time of no more than about 20–40 hours.

Where it is desirable to increase the replicative capacity of pPS cells, or cells differentiated from them, they can be immortalized or telomerized (either before or after differentiation) using the methods described below.

Direct Differentiation of Propagated pPS Cells

This invention also provides a new system for differentiating pPS cells into committed precursor cells or fully differentiated cells without forming embryoid bodies as an intermediate step.

General principles in culturing embryoid bodies are reported in O'Shea, Anat. Rec. (New Anat. 257:323, 1999). pPS cells are cultured in a manner that permits aggregates to form, for which many options are available: for example, by overgrowth of a donor pPS cell culture, or by culturing pPS cells in culture vessels having a substrate with low adhesion properties which allows EB formation. Embryoid bodies can also be made in suspension culture. pPS cells are harvested by brief collagenase digestion, dissociated into clusters, and plated in non-adherent cell culture plates. The aggregates are fed every few days, and then harvested after a suitable period, typically 4–8 days. The cells can then be cultured in a medium and/or on a substrate that promotes enrichment of cells of a particular lineage. The substrate can comprise matrix components such as Matrigel® (Becton Dickenson), laminin, collagen, gelatin, or matrix produced by first culturing a matrix-producing cell line (such as a fibroblast or endothelial cell line), and then lysing and washing in such a way that the matrix remains attached to the surface of the vessel. Embryoid bodies comprise a heterogeneous cell population, potentially having an endoderm exterior, and a mesoderm and ectoderm interior.

It has now been discovered that pPS cells can be differentiated into committed precursor cells or terminally differentiated cells without forming embryoid bodies or aggregates as an intermediate step. Briefly, a suspension of undifferentiated pPS cells is prepared, and then plated onto a solid surface that promotes differentiation. In general, cultures of pPS cells are typically harvested when they have proliferated to an adequate density, but not to the point of over-confluence, because the cells will differentiate in an uncontrolled fashion if allowed to overgrow. A suitable suspension can be prepared by incubating the culture dish with Collagenase IV for about 5–20 min, and then scraping the cells from the dish. The cells can be dissociated, for example, by triturating in a pipette. For many types of differentiation, it is recommended that the cells not be completely dissociated, so that the majority of pPS is in clumps of about 10 to 200 cells.

The suspension is then plated onto a substrate that promotes regulated differentiation into committed precursor cells. Suitable substrates include glass or plastic surfaces that are adherent. For example, glass coverslips can be coated with a poly-cationic substance, such as a polyamine like poly-lysine, poly-ornithine, or other homogeneous or mixed polypeptides or other polymers with a predominant positive charge. The cells are then cultured in a suitable nutrient medium that is adapted to promote differentiation towards the desired cell lineage.

In some instances, differentiation is promoted by withdrawing serum or serum replacement from the culture medium. This can be achieved by substituting a medium devoid of serum and serum replacement, for example, at the time of replating, by withdrawing one or more components of the medium that promotes growth of undifferentiated cells or inhibits differentiation. Examples include certain growth factors, mitogens, leukocyte inhibitory factor (LIF), basic fibroblast growth factor (bFGF), and other components in conditioned medium.

In some instances, differentiation is promoted by adding a medium component that promotes differentiation towards the desired cell lineage, or inhibits the growth of cells with undesired characteristics. For example, to generate cells committed to neural or glial lineages, the medium can include any of the following factors or medium constituents in an effective combination: Brain derived neurotrophic factor (BDNF), neutrotrophin-3 (NT-3), NT-4, epidermal growth factor (EGF), ciliary neurotrophic factor (CNTF), nerve growth factor (NGF), retinoic acid (RA), sonic hedgehog, FGF-8, ascorbic acid, forskolin, fetal bovine serum (FBS), and bone morphogenic proteins (BMPs).

General principals for obtaining tissue cells from pluripotent stem cells are reviewed in Pedersen (Reprod. Fertil. Dev. 6:543, 1994), and U.S. Pat. No. 6,090,622. For neural progenitors, neural restrictive cells and glial cell precursors, see Bain et al., Biochem. Biophys. Res. Commun. 200:1252, 1994; Trojanowski et al., Exp. Neurol. 144:92, 1997; Wojcik et al., Proc. Natl. Acad. Sci. USA 90:1305-130; Mujtaba et al., Dev. Biol. 214:113, 1999; and U.S. Pat. Nos. 5,851,832, 5,928,947, 5,766,948, and 5,849,553. For cardiac muscle and cardiomyocytes see Chen et al., Dev. Dynamics 197: 217, 1993 and Wobus et al., Differentiation 48:173, 1991.

For hematopoietic progenitors, see Burkert et al., New Biol. 3:698, 1991 and Biesecker et al., Exp. Hematol. 21:774, 1993. U.S. Pat. No. 5,773,255 relates to glucose-responsive insulin secreting pancreatic beta cell lines. U.S. Pat. No. 5,789,246 relates to hepatocyte precursor cells. Other progenitors of interest include but are not limited to chondrocytes, osteoblasts, retinal pigment epithelial cells, fibroblasts, skin cells such as keratinocytes, dendritic cells, hair follicle cells, renal duct epithelial cells, smooth and skeletal muscle cells, testicular progenitors, and vascular endothelial cells.

Scientists at Geron Corporation have discovered that culturing pPS cells or embryoid body cells in the presence of ligands that bind growth factor receptors promotes enrichment for neural precursor cells. The growth environment may contain a neural cell supportive extracellular matrix, such as fibronectin. Suitable growth factors include but are not limited to EGF, bFGF, PDGF, IGF-1, and antibodies to receptors for these ligands. Cofactors such as retinoic acid may also be included. The cultured cells may then be optionally separated based on whether they express a marker such as A2B5. Under the appropriate circumstances, populations of cells enriched for expression of the A2B5 marker may have the capacity to generate both neuronal cells (including mature neurons), and glial cells (including astrocytes and oligodendrocytes). Optionally, the cell populations are further differentiated, for example, by culturing in a medium containing an activator of cAMP. Markers of interest include but are not limited to β-tubulin III or microtubule-associated protein 2 (MAP-2), characteristic of neurons; glial fibrillary acidic protein (GFAP), present in astrocytes; galactocerebroside (GalC) or myelin basic protein (MBP); characteristic of oligodendrocytes; OCT-4, characteristic of undifferentiated hES cells; Nestin or Musashi, characteristic of neural precursors and other cells; and both A2B5 and NCAM, which appear on populations of neural precursors differentiated from pPS cells.

Scientists at Geron Corporation have also discovered that culturing pPS cells or embryoid body cells in the presence of a hepatocyte differentiation agent promotes enrichment for hepatocyte-like cells. The growth environment may contain a hepatocyte supportive extracellular matrix, such as collagen or Matrigel®. Suitable differentiation agents include various isomers of butyrate and their analogs, exemplified by n-butyrate. The cultured cells are optionally cultured simultaneously or sequentially with a hepatocyte maturation factor, such as an organic solvent like dimethyl sulfoxide (DMSO); a maturation cofactor such as retinoic acid; or a cytokine or hormone such as a glucocorticoid, epidermal growth factor (EGF), insulin, transforming growth factors (TGF-α and TGF-β), fibroblast growth factors (FGF), heparin, hepatocyte growth factors (HGF), interleukins (IL-1 and IL-6), insulin-like growth factors (IGF-I and IGF-II), and heparin-binding growth factors (HBGF-1). Hepatocyte lineage cells differentiated from pPS cells will typically display at least three of the following markers: $\alpha_1$-antitrypsin (AAT) synthesis, albumin synthesis, asialoglycoprotein receptor (ASGR) expression, absence of α-fetoprotein, evidence of glycogen storage, evidence of cytochrome p450 activity, and evidence of glucose-6-phosphatase activity.

Cell types present in mixed cell populations derived from pPS cells can be recognized by characteristic morphology and the markers they express. For skeletal muscle: myoD, myogenin, and myf-5. For endothelial cells: PECAM (platelet endothelial cell adhesion molecule), Flk-1, tie-1, tie-2, vascular endothelial (VE) cadherin, MECA-32, and MEC-14.7. For smooth muscle cells: specific myosin heavy chain. For cardiomyocytes: GATA-4, Nkx2.5, cardiac troponin 1, α-myosin heavy chain, and ANF. For pancreatic cells, pdx and insulin secretion. For hematopoietic cells and their progenitors: GATA-1, CD34, β-major globulin, and β-major globulin like gene βH1.

Differentiating pPS cells by directly plating on a suitable surface, or by providing pPS cells in feeder-free culture and changing the medium appropriately, can produce a surprisingly homogeneous population of lineage-restricted cells or terminally differentiated cells. Depending on the conditions used, cell populations that are well over 50% homogeneous (as much as 75%, 90%, or 98% homogeneous) can be obtained—even without having to employ a sorting technique.

For therapeutic use, it is usually desirable that differentiated cell populations be substantially free of undifferentiated pPS cells. One way of depleting undifferentiated stem cells from the population is to transfect them with a vector in which an effector gene under control of a promoter that causes preferential expression in undifferentiated cells. Suitable promoters include the TERT promoter and the OCT-4 promoter. The effector gene may be directly lytic to the cell (encoding, for example, a toxin or a mediator of apoptosis). Alternatively, the effector gene may render the cell susceptible to toxic effects of an external agent, such as an antibody or a prodrug. Exemplary is a herpes simplex thymidine kinase (tk) gene, which causes cells in which it is expressed to be susceptible to ganciclovir. Suitable TERT promoter tk constructs are provided in WO 98/14593 (Morin et al.).

cDNA Libraries

Undifferentiated pPS cells grown with feeder cells or from feeder-free cultures can be used to prepare mRNA and cDNA libraries that reflect the gene expression patterns of these cells. mRNA and cDNA can also be made from differentiated cells, and used to produce subtraction libraries enriched for transcripts that are up- or down-regulated during differentiation.

Isolating mRNA and Making Amplified Copies

Preparing a cDNA library will typically involve isolating mRNA from pPS cells or their differentiated progeny; making a polynucleotide copy of the mRNA, and producing a library that contains the polynucleotide copies in a form that can be replenished. Typically, the polynucleotide copy is cDNA generated by a reverse transcriptase reaction from the mRNA template, but any other type of copy that retains the sequence of the original mRNA population can be used. Optionally, polynucleotide copies from different sources (for example, pPS and differentiated cells) are subtracted to produce a library enriched for copies differentially expressed between the two populations. The selected polynucleotide copies are typically engineered into a cloning vector, but any way of reproducing the copies in a vector, a host cell, or by chemical means are understood to be equivalent.

By way of illustration, hES cells in feeder-free culture are released from the matrix using collagenase and collected by centrifugation, or lysed directly in culture using a suitable solvent. Total RNA is prepared from the cells by an appropriate combination of standard techniques (e.g., acid phenol/chloroform extraction, centrifugation through CsCl, binding to an oligo-dT matrix, etc.; see Sambrook et al., supra). As illustrated in Example 14, total RNA can be isolated from harvested hES cells by lysing the cells in a solution of guanidinium isothiocyanate and binding RNA in the suspension to a suitable matrix (U.S. Pat. No. 5,234,809), such as an RNeasy® spin column (Qiagen Inc., Valencia Calif.).

Total RNA is eluted from the matrix, and then poly A+mRNA is obtained by binding to Oligotex™ beads having bound $dC_{10}T_{30}$ oligonucleotides. The adherent fraction is collected in a low salt buffer, and can be used to prepare a cDNA library.

A variety of methodologies is available to convert mRNA into double-stranded cDNA. Products include primary libraries, designed to represent the starting mRNA population; subtracted libraries, in which mRNA species common to two or more different mRNA population are reduced in the final cDNA preparation to enrich for mRNA preferentially expressed in one population; normalized libraries, in which the relative abundance of independent mRNAs is balanced towards equal representation; and full-length biased libraries, in which the production of cDNA is optimized to produce a high frequency of cDNA that include the entire coding sequence of the original mRNA.

The first reaction in these methods is typically the conversion of mRNA into a single-stranded cDNA using a template-dependent reverse-transcription reaction primed with oligo-dT or random hexamer primers. This reaction is catalyzed by a reverse-transcriptase, a class of enzymes readily obtainable from commercial suppliers. Exemplary is SuperScript II™ (Life Technologies Inc., Bethesda), a modified version of reverse transcriptase in which RNAse H activity of the native enzyme has been reduced, thereby increasing the frequency with which full-length first strand cDNA is produced. Oligo-dT primers are typically modified on the 5' end to incorporate a restriction endonuclease recognition sequence to facilitate cloning. Often, a methylated version of one nucleotide triphosphate is included in the first strand reaction. Thus, the final cDNA is protected from digestion with restriction endonucleases typically used to restrict the final product.

Conversion of the single strand cDNA product of the reverse transcriptase reaction to double-strand cDNA can be accomplished by several means. Typically, the first strand cDNA is adapted to allow the priming of complementary strand synthesis by a suitable DNA polymerase. The SMART™ technology (ClonTech, Palo Alto, Calif.) utilizes a strand switch oligonucleotide that primes second strand synthesis from terminal cytosine residues at the terminus of the first strand product. Other techniques for adapting the first strand cDNA product include introduction of a homopolymeric tail using terminal deoxynucleotidyl transferase followed by second strand priming with the complementary homopolymer, or the ligation of an appropriate oligonucleotide followed by second strand priming with a primer complementary to the ligated oligo. With this latter approach, the ligated oligonucleotide and its complement can be designed to include restriction endonuclease recognition sequences that facilitate cloning.

In one illustration, the action of RNAse H is used to introduce nicks into the RNA/DNA duplex, which then become suitable as priming sites for DNA polymerases, such as PolI from *E. coli*. This method is efficient, but sequence information may be lost from the 5' end of the cDNA, since the priming RNA overlying the 5' end (the terminus opposite of the polyA+ site in the original mRNA) will be lost with subsequent processing of the double-stranded cDNA. Alternatively, double-stranded DNA in which the 5' sequence information is preserved involves ligation of an oligonucleotide primer to the 3' end of first strand cDNA. This ligation reaction is catalyzed by T4 RNA ligase, an enzyme capable of joining the terminal 5' phosphate of a single strand oligonucleotide with the 3'-hydroxyl of the first-strand cDNA product. The oligonucleotide used is synthesized so as to provide a 5'-terminal phosphate, to allow ligation to the cDNA, and a 3'-blocking group, such as an amino- or dideoxy-derivatives, to prevent self-concatemerization. This oligonucleotide also encodes restriction endonuclease recognition sequences that adapt sites appropriate for subsequent cloning into vectors. Following ligation of the oligonucleotide to the first strand cDNA products, second strand cDNA synthesis is primed with an oligonucleotide complementary to the ligated oligo using an appropriate DNA polymerase activity, such as thermostable polymerases. Sequence example: first strand cDNA ligation oligo 5' P-AGGTCGACGAGAGAG-3'NH-X (SEQ. ID NO:1), where P=phosphate, NH—X=amine blocking group; complementary oligo 5' OH-CTCTC TCGTC GACCT-OH-3' (SEQ. ID NO:2), where —OH=hydroxyl group.

Certain procedures can be used to increase the proportion of full-length cDNA in the sample. Suitable for this purpose is technology developed at the RIKEN Institute, Japan (Caminci et al., Methods Enzymol. 303:19, 1999; Itoh et al., Genome Res.9:463, 1999; see also International Patent Application WO 98/20122). mRNA is adapted by adding a biotin to the 7-methyl G cap structure at the 5'-end of the mRNA. Production of the first strand cDNA is achieved as already described, and the cDNA/mRNA hybrid is treated with RNAse I, which degrades single stranded mRNA. mRNA that is not protected by hybridization to a full-length cDNA is hydrolyzed, while full-length cDNA/mRNA hybrids remain. The hybrids are purified using streptavidin-coated beads that bind the biotin at the 5' cap, and converted into double-strand cDNA using standard techniques. The resulting proportion of full-length cDNA in the sample is typically much higher than what is present in libraries made by traditional methods. Several commercial vendors offer services to produce full-length biased cDNA, including Life Technologies Inc. (Bethesda, Md.) and Seqwright Inc. (Houston, Tex.).

Subtracted libraries provide an enriched source of genes whose expression levels differ between two mRNA populations. Methods for making subtracted libraries typically involve amplifying mRNA obtained from pPS cells (for example, by forming a cDNA population as already described); amplifying mRNA obtained from differentiated cells; incubating the two pools together under conditions that permit polynucleotides amplified from mRNA expressed in both the pPS cells and the differentiated cells to cross-hybridize; and then recovering amplified polynucleotides that have not cross-hybridized.

In a similar fashion, subtracted libraries can be made from other combinations of mRNA isolates—for example, pPS cells from feeder cultures vs. pPS cells in feeder-free culture; partially differentiated cells vs. terminally differentiated cells; or differentiated cell populations of two or more different lineages. In another example, cDNA from pPS cells differentiated in monolayer culture (by plating on a matrix or other substrate that promotes differentiation, or by treating with agents such as DMSO or retinoic acid) is subtracted from cDNA from pPS cells grown in feeder-free culture, to correct for the proportion of differentiated cells that form on the periphery around each colony. Subtraction libraries can also be made to ascertain the effect of a compound or change in culture conditions on expression patterns in undifferentiated pPS cells, or their differentiated progeny. Amplified mRNA is made from cells exposed to the compound or condition, and subtracted with amplified mRNA from control cells. The library will thereby be enriched for transcripts that are upregulated or downregulated as a result of the change.

The preparation of subtraction libraries can be illustrated as follows: two independent mRNA pools are prepared, one termed the tester and the other the driver. In this illustration, they are converted into an appropriate form, often single stranded cDNA (one of the pools in sense orientation, the other in antisense orientation), and then mixed to allow hybridization. Transcripts that are common to both mRNA populations will form hybrids, while those transcripts that are found only in one pool, or are expressed at substantially higher levels in one pool, remain unhybridized. The hybrids are then removed, typically by partitioning over chromatographic columns or by retrieval using specific biochemical systems such as streptavidin/biotin. The remaining single-strand sequences, now enriched for genes that are more highly expressed in the tester mRNA pool, are cloned into a suitable vector. Many variations of subtractive library production have been developed. A method that combined the features of subtractive hybridization incorporating normalization is commercially available (Suppressive Subtractive Hybridization (SSH), ClonTech, Palo Alto, Calif.).

Preparing Recombinant Expression Libraries

Double-stranded cDNA made by these techniques can be engineered into a variety of cloning vectors. Suitable vector systems include bacterial plasmids and lambda bacteriophage for cloning in bacterial hosts. When the cDNA is produced with endonuclease-restricted termini, cloning is often accomplished by ligation with correspondingly restricted vector DNA. Plasmid libraries are favored for sequence analysis, since the individual clones can be readily processed by high-throughput purification and PCR amplification protocols.

In certain embodiments of the invention, the cloning vector is also an expression vector, designed so that isolated plaques can be transfected into cells to obtain the gene product. Accordingly, the amplified transcripts are placed in the vector under control of transcription and translation control elements. For instance, the plasmid pCMVSport™ 6.0 (Life Technologies Inc., Bethesda Md.) contains SP6 and T7 viral RNA polymerase promoters on opposite flanks of the multiple cloning site, allowing for the transcription of sense or antisense strands of cloned cDNA. As well, a CMV promoter cassette confers in vivo transcription when introduced into mammalian host cells. Thus, cDNA inserted into such vectors can be tested for expression in a variety of host cells, including pPS cells. This vector also features lambda phage attachment sequences flanking the multiple cloning site, making them compatible with Life Technologies Gateway™ vectors. The Gateway™ system includes vectors that are specifically modified with sequences that allow for the transfer of cloned sequences between vectors by use of a enzyme cocktail of lambda phage and *E. coli* recombinase activities. This obviates the need to use restriction enzyme digestions when transferring sequences between vectors.

Of particular interest are libraries optimized for expression of the cDNA in pluripotent stem cells. Methylation patterns and other regulatory control mechanisms in embryonic cells can suppress transcription of genes under control of promoters such as CMV, which are active in most other eukaryotic cell types. It has been discovered that promoters for house-keeping genes active in pPS cells may be effective for controlling transcription of artificially introduced encoding regions. As illustrated in Example 14, an appropriate promoter can be selected experimentally using reporter constructs comprising test promoter sequences, a reporter gene such as green fluorescent protein or β-galactosidase, and a drug resistance gene. An appropriate promoter will have the characteristic of causing expression of the reporter gene, without substantially increasing the proportion of cells lost to differentiation. Using this selection strategy, the promoter for PGK, EF1α, and UbiC have been determined as effective for construction of libraries expressible in pPS cells.

Characterizing Recombinant Expression Libraries cDNA libraries can be characterized by several criteria. A simple and direct estimation of the length of cDNAs can be made by digesting plasmid preparations from individual clones with restriction enzymes that release the cDNA insert. The digestion products can be sized by electrophoresis using agarose gels, and a median cDNA insert length can be calculated. Certain characteristics of expression libraries can be achieved by comparing sequences generated from the 5' end of individual cDNA clones with sequences found in public databases. Polynucleotide isolates and cloned inserts of this invention can be sequenced using any suitable method in the art. Exemplary are PCR-based sequencing methods that form fluorescent products to be resolved using automated DNA sequencers. The plasmid DNA and a sequencing primer are reacted under PCR reaction conditions that include fluorescently-labeled dideoxynucleotide triphosphates. The resulting reaction products are resolved on an appropriate DNA sequencer, such as the ABI 377 (Perkin-Elmer Biosystems, Foster City Calif.). The fluorescence signal is detected, converted into raw sequence information and processed. DNA sequencing services based substantially on these methods are available commercially from such companies as Lark Technologies, Houston, Tex.; and Incyte Genomics, Palo Alto, Calif. Having obtained the open reading frame of the mRNA encoding sequence, the amino acid sequence of the protein gene product can normally be determined without further experimentation by translating the encoding sequence according to the genetic code.

The sequence data provides a general estimate of the diversity of the cDNA library, based on the number of independent genes represented. For instance, comparing the cDNA sequences to the UNIGENE collection (available at the website of the National Center for Biotechnology Information) allows assignment of a unique cluster identifier for most sequences. By comparing the number of assigned cluster identifiers to the total number of cDNAs evaluated, an estimate of the clone diversity can be achieved.

Libraries that represent less complex mRNA sources have relatively fewer independent gene sequences represented in a given number of cDNAs compared to libraries made from more complex mRNA sources. In certain embodiments of this invention, mRNA preparations, cDNA preparations, and libraries in cloning vectors contain sequences representing at least 100, 1,000, 10,000, or even 50,000 genes expressed at the mRNA level in pPS cells or their differentiated progeny.

Libraries can also be characterized by whether they contain transcripts from cells of a single genotype. Crude sequence data from different plaques are matched with databases of human sequences, and sequences of other species that are also suspected of being present. The library is referred to as "essentially free" of cDNA of other species, vertebrates, mammals, and different genotypes of the same species if less than about 1% of the transcript copies in the library have sequences establishing that they did not originate from the genotype from which the cDNA library is desired. Using the feeder-free culture systems described in this disclosure, the degree of contamination of pPS cell libraries with foreign transcripts can be less than 0.2%, 0.05%, 0.01%, or 0.001%, depending on the number of passages from the last culturing of the pPS cells on a feeder layer.

The 5' sequences from cDNAs can also be compared to collections of annotated full-length mRNA sequences to determine the proportion of cDNAs that represent full-length sequences. In this context, full-length sequences can be defined as those that include the initiator methionine codon for an encoded protein. For example, 5' sequence reads can be compared to the REFSEQ collection (GenBank) using an appropriate search program such as BLAST. For those cDNA sequences that match to a REFSEQ entry, an evaluation of the sequence alignment can indicate whether the cDNA sequence includes the initiator methionine for the protein encoded by the REFSEQ entry and thus the proportion of full-length cDNAs can be estimated. Since the REFSEQ collection is annotated to indicate the estimated size of full-length mRNA, this analysis can be evaluated further to determine the percentage of full-length cDNAs that correspond to mRNAs of a particular size. For example, it is possible to compare the percentage of full-length cDNAs that correspond to mRNAs of less than 1 kb in length, versus the percentage of full-length cDNAs that correspond to mRNAs greater than 1 kb in length.

Depending on the method by which such products are derived, the proportion of cDNA that comprises the entire encoding region of the corresponding mRNA can be at least 15%, 30%, and sometimes 50% of the polynucleotide or vectors in the preparation. The median length of the insert can be at least ~0.5 kb, 1 kb, 2 kb, or 4 kb, depending on the method used to obtain and select the double-stranded cDNA preparation.

Use of Information from Expression Libraries

Once the sequence of an mRNA or cDNA from pPS cells or their differentiated progeny has been determined, it can be used in the manufacture of polynucleotides that contain such sequences, polypeptides they encode, and antibody specific for the polypeptides.

Polynucleotides are manufactured according to techniques of nucleic acid chemistry for any suitable purpose in research, diagnostic, or therapeutic applications. Nucleotide sequences can be modified to remove segments of the native coding region, add additional encoding sequence, or introduce mutations and other changes for any desirable purpose. Substantially identical polynucleotides or polynucleotide fragments hybridize under stringent conditions to cDNA in an expression library from pPS cells or their differentiated progeny, in preference to other nucleotide sequences contained in the human genome or expressed in other cell types. Typical conditions of high stringency for the binding of a probe of about 100 base pairs and above is a hybridization reaction at 65° C. in 2×SSC, followed by repeat washes at 0.1 x SSC. In certain embodiments, a segment of the manufactured polynucleotide is at least ~80%, 90%, 95%, or 100% identical to a sequence or part of a sequence determined for a cDNA obtained as described in this disclosure. The length of consecutive residues in the identical or homologous sequence compared with the exemplary sequence can be at least ~15, 30, 50, 75, 100, 200 or 500 residues in order of increasing preference.

Based on the desired nucleic acid sequence, polynucleotides can be manufactured according to any suitable technique. Oligonucleotides of less than ~50 base pairs are conveniently prepared by chemical synthesis, either through a commercial service or by a known synthetic method, such as the triester method or the phosphite method. A suitable method is solid phase synthesis using mononucleoside phosphoramidite coupling units (Hirose et al., *Tetra. Lett.* 19:2449–2452, 1978; U.S. Pat. No. 4,415,732). Polynucleotides with modified backbones can be prepared, such as those described in U.S. Pat. Nos. 5,578,718; 5,541,307; 5,378,825. Preparation of peptide nucleic acids is described in U.S. Pat. Nos. 5,539,082, 5,766,855, 5,786,461, and EP Application 97918549.2.

Alternatively, polynucleotides can be manufactured by PCR amplification using a template with the desired sequence. Oligonucleotide primers spanning the desired sequence are annealed to the template, elongated by a DNA polymerase, and then melted at higher temperature so that the template and elongated oligonucleotides dissociate. The cycle is repeated until the desired amount of amplified polynucleotide is obtained (U.S. Pat. Nos. 4,683,195 and 4,683,202). Suitable templates include expression libraries prepared from pPS cells or their progeny, or a library from any tissue where the corresponding gene is expressed in humans. Production scale amounts of large polynucleotides are conveniently obtained by inserting the desired sequence into a suitable cloning vector, and either reproducing the clone, or transfecting the sequence into a suitable host cell. Techniques for nucleotide cloning are given in Sambrook, Fritsch & Maniatis (supra) and in U.S. Pat. No. 5,552,524. Polynucleotides can be purified by standard techniques in nucleic acid chemistry, such as phenol-chloroform extraction, agarose gel electrophoresis, and other techniques known in the art, adapted according to the source.

The sequence data of an mRNA or cDNA from pPS cells can also be used to manufacture peptides that comprise a sequence contained in an encoding region. Amino acid sequences can be modified to remove or add segments, or introduce mutations and other changes for any desirable purpose. Substantially identical polypeptides or polypeptide fragments share an epitope recognized by an antibody specific for a protein encoded in a cDNA of an expression library from pPS cells or their differentiated progeny, in preference to other nucleotide sequences contained in the human genome or expressed in other cell types. In certain embodiments, the peptides are 60%, 80%, 90%, 95%, or 100% identical to a peptide or peptide fragment encoded in the mRNA or cDNA, in order of increasing preference. The length of the identical or homologous sequence compared with the prototype polypeptide can be about 7,10, 15, 25, 50 or 100 residues in order of increasing preference, up to the length of the entire protein.

Polypeptides and their variants can be manufactured according to any suitable technique. Short polypeptides can be prepared by solid-phase chemical synthesis. The principles of solid phase chemical synthesis can be found in Dugas & Penney, Bioorganic Chemistry, Springer-Verag N.Y. pp 54–92 (1981), and U.S. Pat. No. 4,493,795. Automated solid-phase peptide synthesis can be performed using devices such as a PE-Applied Biosystems 430A peptide synthesizer (commercially available from Applied Biosystems, Foster City Calif.).

Longer polypeptides are conveniently manufactured by translation in an in vitro translation system, or by expression in a suitable host cell. To produce an expression vector, a polynucleotide encoding the desired polypeptide is operatively linked to control elements for transcription and translation, and then transfected into a suitable host cell, including prokaryotes such as *E. coli*, eukaryotic microorganisms such as the yeast *Saccharomyces cerevisiae*, or higher eukaryotes, such as insect or mammalian cells. A number of expression systems suitable for producing the peptides of this invention are described in U.S. Pat. No. 5,552,524. Expression cloning is available from such commercial services as Lark Technologies, Houston Tex. Following production, the protein is typically purified by standard methods in protein chemistry in appropriate combination, which may include ion exchange chromatography, affinity chromatography, or HPLC.

Polyclonal and monoclonal antibody specific for polypeptides encoded by mRNA and cDNA of this invention can be obtained by determining amino acid sequence from a protein encoding region in an expression library, and immunizing an animal or contacting an immunocompetent cell or particle with a protein containing the determined sequence. Production of monoclonal antibody is described in such standard references as Harrow & Lane (1988), U.S. Pat. Nos. 4,491,632, 4,472,500 and 4,444,887, and Methods in Enzymology 73B:3 (1981). Other methods of obtaining specific antibody molecules (optimally in the form of single-chain variable regions) involve contacting a library of immunocompetent cells or viral particles with the target antigen, and growing out positively selected clones. See Marks et al., New Eng. J. Med. 335:730, 1996, International Patent Publications WO 94/13804, WO 92/01047, WO 90/02809, and McGuiness et al., Nature Biotechnol. 14:1449, 1996. By positively selecting using pPS of this disclosure, and negatively selecting using cells bearing more broadly distributed antigens (such as differentiated embryonic cells) or adult-derived stem cells, the desired specificity can be obtained.

Polynucleotides, polypeptides, and antibody derived from sequence data obtained from mRNA or cDNA of this invention have a number of important commercial applications. For example, genes or proteins that are expressed in pPS cells but decrease during differentiation can be used as molecular markers of the undifferentiated state. Reagents corresponding to these markers, such as antibodies, can be used to eliminate undifferentiated pPS cells from a population of differentiated cells by immunoaffinity isolation or complement-mediated lysis. Genes or proteins that increase expression levels during differentiation can be used in a similar manner to purify, enrich, remove or eliminate specific cell types derived from pPS cells. These markers may serve as indicators of broad classes of cell differentiation, such as genes or proteins expressed in mesodermal, endodermal or ectodermal lineages, or may serve as specific markers of a confined spectrum of highly differentiated cell types.

Genes that are upregulated during expression may also be useful to influence the differentiation of pPS cells into specific lineages. For instance, the forced expression in undifferentiated pPS cells of transgenes encoding transcription factors, growth factors, receptors and signaling molecules can be tested for an ability to influence differentiation into specific cell lineages.

Genetic Alteration of Pluripotent Stem Cells

This disclosure also provides a system for obtaining pPS cells that have been genetically altered, either in a transient or stable fashion. This is desirable for a number of purposes. One of the promises of pPS cells is the potential to obtain reservoirs of different tissue types, for research, diagnostic, and therapeutic purposes. To promote enrichment for particular differentiated cell populations, it may be possible to introduce genes that influence differentiation or help eliminate undifferentiated cells. Methods of genetic selection are described, for example, in U.S. Pat. Nos. 5,602,301, 5,733,727, and 6,015,671; and in International Patent Publications WO 98/32868, WO 99/53022, and WO 99/55841.

In particular embodiments, the present invention provides methods of obtaining genetically altered pPS cells by providing a composition of pPS cells on a layer of feeder cells that are drug-resistant, transferring a polynucleotide into pPS cells in the composition; and selecting genetically altered cells in the composition using the drug to which the feeder cells are resistant. In particular embodiments, the polynucleotide comprises a protein encoding region operably linked to a promoter that promotes transcription of the encoding region in an undifferentiated pPS cell. In other embodiments, the polynucleotide comprises a protein encoding region operably linked to a promoter that promotes transcription of the encoding region in one or more cell types produced by differentiating the pPS cell Other reasons to genetically alter stem cells is to immortalize them by providing an expression system for the catalytic component of telomerase (TERT), or otherwise genetically adapt them for an in vitro use such as drug screening. For therapeutic applications, it may be beneficial to modify cells with therapeutic genes, or to render cells histocompatible with the intended recipient. Genetic alteration can also be used to prepare cells for sorting after differentiation. For example, the hES cells are transfected with a drug susceptibility gene, such as herpes simplex virus thymidine kinase (which renders cells susceptible to ganciclovir), under control of a promoter specific for undifferentiated cells, such as the OCT-4 promoter or the hTERT promoter (WO 98/14593). After the culture has been made to differentiate, residual undifferentiated cells can be eliminated from the population using ganciclovir.

It has been discovered that pPS cells can be genetically altered in a manner that permits the genetic alteration to be either transient, or stable and inheritable as the cells divide. The genetically altered cells can be maintained in undifferentiated pluripotent form in culture, or they can be differentiated into other types of cells still retaining the genetic alteration. Effective methods have been discovered that allow hES cells to be genetically altered when grown on primary feeder cells. Methods are also provided in which hES cells are plated in a feeder-free environment before transfection, which provides a number of important advantages.

The polynucleotide to be transferred in the cell typically provides a function that will change the phenotype of the cell or its progeny in a desirable fashion. For example, it may contain an encoding region under control of a promoter that promotes transcription in undifferentiated hES cells, or in differentiated cells of a particular lineage. It may also affect endogenous gene expression by a suitable mechanism, such as antisense reactivity, triplex formation, or ribozyme action.

Suitable methods for transferring vector plasmids into hES cells include lipid/DNA complexes, such as those described in U.S. Pat. Nos. 5,578,475; 5,627,175; 5,705,308; 5,744,335; 5,976,567; 6,020,202; and 6,051,429. Suitable reagents include lipofectamine, a 3:1 (w/w) liposome formulation of the poly-cationic lipid 2,3-dioleyloxy-N-[2 (sperminecarboxamido)ethyl]-N,N-dimethyl-1-propan-aminium trifluoroacetate (DOSPA) (Chemical Abstracts Registry name: N-[2-(2,5-bis[(3-aminopropyl)amino]-1-oxpentyl}amino) ethyl]-N,N-dimethyl-2,3-bis(9-octadecenyloxy)-1-propanaminium trifluoroacetate), and the neutral lipid dioleoyl phosphatidylethanolamine (DOPE) in membrane filtered water. Exemplary is the formulation Lipofectamine 2000™ (available from Gibco/Life Technologies # 11668019). Other reagents include: FuGENE™ 6 Transfection Reagent (a blend of lipids in non-liposomal form and other compounds in 80% ethanol, obtainable from Roche Diagnostics Corp. # 1814443); and LipoTAXI™ transfection reagent (a lipid formulation from Invitrogen Corp., # 204110).

Suitable viral vector systems for producing hES cells with stable genetic alterations are based on adenovirus and retrovirus, and may be prepared using commercially available virus components.

For many applications, genetic alteration of hES cells requires attention to two different agenda: achieving sufficiently high efficiency of genetic alteration, and performing the alteration in a manner that does not promote differentiation of the hES cells along an undesired pathway. Screening of various transfection and transduction systems, and optimization of reaction timing and conditions, can be conveniently performed in experiments using an expression vector with an encoding region for a detectable label. Particularly convenient labels are intrinsically fluorescent, such as luciferase, or green fluorescent protein (GFP). The label may also be an enzyme that can be detected in histopathology or quantitated by enzyme reaction. Examples include alkaline phosphatase, and β-galactosidase. The label may also be a cell-surface protein that can be stained with labeled antibody and quantitated, for example, in a fluorescence activated cell counting device. Once an effective system has been identified and optimized, the encoding region for the label may then be substituted with the gene of interest.

To monitor genetically altered cells for differentiation, the cells can be tested for expression of markers characteristic of pPS cells, such as SSEA-4, OCT-4, and TERT. Transfection efficiencies can thereby be calculated as a percentage of cells bearing the undifferentiated phenotype. The pluripotency of genetically altered cells can also be confirmed by inducing differentiation, either in vitro (e.g., via embryoid body formation) or in vivo (by teratoma formation), and comparing the types of cells produced with those produced by hES cells not genetically altered.

By these criteria, and tracking transfection with a GFP containing plasmid vector and surface expression of SSEA-4, it has been determined that efficiency of genetic alteration can generally be improved if pPS cells are replated and allowed to stabilize for 48 h before adding the vector. Peak expression of markers such as GFP occur ~24 h later.

Efficiencies of genetic alteration are rarely 100%, and it is usually desirable to enrich the population for cells that have been successfully altered. When hES cultures on fibroblast feeder cells are used, then the efficiency may be 5 to 20% of the undifferentiated cells. The genetically altered cells can be enriched by taking advantage of a functional feature of the new genotype. For example, where the pPS cells are transfected with a label such as GFP, or with an immunostainable surface marker such as NCAM, then the pPS cells can be suspended, separated by fluorescence-activated cell sorting, and replated. The reader is cautioned that complete separation of pPS cells usually promotes differentiation.

A particularly effective way of enriching genetically altered cells is positive selection using resistance to a drug such as neomycin or puromycin. To accomplish this, the cells can be genetically altered by contacting simultaneously with vector systems for the marker gene or gene of interest, and a vector system that provides the drug resistance gene. If the proportion of drug resistance gene in the mixture is low (say, 3:1), then most drug resistant cells should also contain the gene of interest. Alternatively, the drug resistance gene can be built into the same vector as the gene of interest. After transfection has taken place, the cultures are treated with the corresponding drug, and untransfected cells are eliminated. Unfortunately, feeder cells in the hES culture would normally also be susceptible to the drug.

To overcome this problem, this disclosure also provides feeder cells that are drug resistant. Cells that are known to provide the environment suitable for propagating pPS cells without differentiation can be introduced with a drug resistance gene, and then reevaluated for their ability to act as feeder cells. Alternatively, feeder cells (such as primary mouse fibroblasts) can be made from non-human mammals that have been rendered transgenic for a drug resistance gene. Such mice are available commercially; e.g., from Jackson Laboratories. The feeder cells can also be immortalized by genetically altering with an expression system for telomerase reverse transcriptase (TERT), or the SV40 Large T Antigen.

Example 8 illustrates a permanent feeder cell line designated NHG190 that has drug resistance genes for hygromycin, neomycin, and puromycin, and which has been telomerized. Surprisingly, despite all the manipulations and genetic perturbations, the cells are still highly effective feeders, providing the matrix substrate and cofactors that support proliferation of hES cells without differentiation. NHG190 cells are also suitable for making conditioned medium that support hES cells in feeder-free culture. Example 9 illustrates how drug-resistant feeder cells can be used for long-term selection of hES cells genetically altered with a drug-resistant gene.

It has been discovered that pPS cells are especially amenable to genetic alteration when they are grown in feeder-free culture (illustrated in Example 10). Transient transfection using DNA/lipid complexes can be as high as 60%. The cells are easier to manipulate, and there are no feeder cells around to act as a sink for the vector. Drug selection does not require availability of a drug-resistant feeder cell. The number of undifferentiated pPS colonies that grow out after transfection may also be improved.

Following genetic alteration and drug selection (on drug-resistant feeders or feeder-free culture), it is possible to pick colonies that demonstrate the altered phenotype, and culture them separately. The picked colonies are dispersed into small clumps of 25–100 cells, and replated in a suitable environment. Using some or all of the strategies outlined in this section and elsewhere in the disclosure, it is possible to achieve cultures of pPS cells in which at least ~25%, 50%, 75%, or even 90% of the undifferentiated cells have been genetically altered.

Telomerizing Pluripotent Stem Cells and Their Derivatives

Where it is desirable to increase the replicative capacity of pPS cells, fibroblasts, or other cell types, they can be telomerized by genetically altering them with a suitable vector (as illustrated above) so that they express the telomerase catalytic component (TERT). Particularly suitable is the catalytic component of human telomerase (hTERT), provided in International Patent Publication WO 98/14592. For some applications, other TERT sequences can be used (mouse TERT is provided in WO 99/27113).

Typically, the vector will comprise a TERT encoding region under control of a heterologous promoter that will promote transcription in the intended undifferentiated or differentiated cell line. Sequences that can drive expression of the TERT coding region include viral LTRs, enhancers, and promoters (such as MPSV, SV40, MoLV, CMV, MSCV, HSV TK), eukaryotic promoters (such as β-actin, ubiquitin, EF1α, and PGK) or combinations thereof (for example, the CMV enhancer combined with the β-actin promoter). Expression of a marker gene can be driven by the same promoter as the TERT gene, either as a separate expression cassette, as part of a polycistronic transcript (in which the coding regions of TERT and the marker gene are separated by an IRES sequence, allowing both individual proteins to be made from a single transcript driven by a single promoter), or as part of the same cassette (a fusion between the coding regions of both TERT and the marker gene, producing a protein that provides the functions of both TERT and the marker gene). Transfection and expression of telomerase in human cells is described in Bodnar et al., Science 279: 349, 1998 and Jiang et al., Nat. Genet. 21:111, 1999.

Before and after telomerization, telomerase activity and hTERT expression can be determined using standard reagents and methods. For example, pPS cells are evaluated for telomerase using TRAP assay (Kim et al., Science 266:2011, 1997; Weinrich et al., Nature Genetics 17:498, 1997). The following assay kits are available commercially for research purposes: TRAPeze® XK Telomerase Detection Kit (Cat. s7707; Intergen Co., Purchase N.Y.); and TeloTAGGG Telomerase PCR ELISAplus (Cat. 2,013,89; Roche Diagnostics, Indianapolis Ind.). hTERT expression can also be evaluated at the mRNA by RT-PCR. The following assay kit is available commercially for research purposes: LightCycler TeloTAGGG hTERT quantification kit (Cat. 3,012,344; Roche Diagnostics).

Other methods of immortalizing cells are also contemplated, such as genetically altering the cells with DNA encoding the SV40 large T antigen (U.S. Pat. No. 5,869,243, International Patent Publication WO 97/32972), infecting with Epstein Bar Virus, introducing oncogenes such as myc and ras, introducing viral replication genes such as adenovirus E1a, and fusing cells having the desired phenotype with an immortalized cell line. Transfection with oncogenes or oncovirus products is usually less suitable when the cells are to be used for therapeutic purposes.

Other Uses of Propagated pPS Cells and Their Derivatives

This description provides a method by which large numbers of pluripotent cells can be produced commercially without the need of feeder cells, and then differentiated into committed precursor cells or terminally differentiated cells. These cell populations can be used for a number of important purposes.

Preparation of Specific Antibody pPS cells maintained without feeder cells can be used to prepare antibody that is specific for embryo markers, stem cell markers, germ cell markers, and other antigens that may be expressed on the cells. The cells described in this disclosure provide an improved way of raising such antibodies because they are essentially free of contaminating antigen from feeder cells. Polyclonal antibody can be prepared by injecting a vertebrate with cells of this disclosure in an immunogenic form. Methods for production of polyclonal and monoclonal antibody are provided above. By positively selecting using pPS of this disclosure, and negatively selecting using cells bearing more broadly distributed antigens (such as differentiated embryonic cells) or adult-derived stem cells, the desired specificity can be obtained.

Screening Proliferation Factors, Differentiation Factors, and Pharmaceuticals pPS cells can be used to screen for factors (such as small molecule drugs, peptides, polynucleotides, and the like) or conditions (such as culture conditions or manipulation) that affect the characteristics of pPS cells in culture. This system has the advantage of not being complicated by a secondary effect caused by perturbation of the feeder cells by the test compound. In one application, growth affecting substances are tested. The conditioned medium is withdrawn from the culture and a simpler medium (such as KO DMEM) is substituted. Different wells are then treated with different cocktails of soluble factors that are candidates for replacing the components of the conditioned medium. Efficacy of each mixture is determined if the treated cells are maintained and proliferate in a satisfactory manner, optimally as well as in conditioned medium. Potential differentiation factors or conditions can be tested by treating the cells according to the test protocol, and then determining whether the treated cell develops functional or phenotypic characteristics of a differentiated cell of a particular lineage.

Feeder-free pPS cultures can also be used for the testing of pharmaceutical compounds in drug research. Assessment of the activity of candidate pharmaceutical compounds generally involves combining the differentiated cells of this invention with the candidate compound, determining any resulting change, and then correlating the effect of the compound with the observed change. The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp 375–410 in "in vitro Methods in Pharmaceutical Research," Academic Press, 1997). Cytotoxicity can be determined by the effect on cell viability, survival, morphology, on the expression or release of certain markers, receptors or enzymes, on DNA synthesis or repair. measured by[$^3$H]-thymidine or BrdU incorporation, or on sister chromatid exchange, determined by metaphase spread. The reader is referred generally to the standard textbook "In vitro Methods in Pharmaceutical Research", Academic Press, 1997, and U.S. Pat. No. 5,030,015.

Genomics

Cells described in this disclosure can be used to identify expression patterns of transcripts and newly synthesized proteins that are characteristic for precursor cells, and may assist in directing the differentiation pathway or facilitating interaction between cells. Expression patterns of the cell population of interest (e.g., human PS cells differentiated directly or through embryoid bodies, or cells of a particular lineage) are compared with control cell lines (e.g., undifferentiated pPS cells, other types of committed precursor cells, terminally differentiated cells, or differentiated cells of another species such as rhesus monkey PS cells) .

Suitable methods for comparing expression at the protein level include the immunoassay or immunocytochemistry techniques described above. Suitable methods for comparing expression at the level of transcription include methods of differential display of mRNA (Liang et al., Cancer Res. 52:6966, 1992), and matrix array expression systems (Schena et al., Science 270:467, 1995; Eisen et al., Methods Enzymol. 303:179, 1999; Brown et al., Nat. Genet. 21 Suppl 1:33, 1999).

The use of microarray in analyzing gene expression is reviewed generally by Fritz et al Science 288:316, 2000; "Microarray BiochIp Technology", M. Schena ed., Eaton Publishing Company; "Microarray analysis", Gwynne & Page. Science (Aug. 6, 1999 supplement); Pollack et al., Nat Genet 23:41, 1999; Gerhold et al., Trends Biochem. Sci. 24:168, 1999; "Gene Chips (DNA Microarrays)", from the website by Leming Shi, Ph.D. Systems and reagents for performing microarray analysis are available commercially from companies such as Affymetrix, Inc., Santa Clara Calif.; Gene Logic Inc., Columbia Md.; HySeq Inc., Sunnyvale Calif.; Molecular Dynamics Inc., Sunnyvale Calif.; Nanogen, San DIego Calif.; and Synteni Inc., Fremont Calif. (acquired by Incyte Genomics, Palo Alto Calif.).

Solid-phase arrays are manufactured by attaching the probe at specific sites either by synthesizing the probe at the desired position, or by presynthesizing the probe fragment and then attaching it to the solid support. A variety of solid supports can be used, including glasses, plastics, ceramics, metals, gels, membranes, paper, and beads of various composition. U.S. Pat. No. 5,445,934 discloses a method of on-chip synthesis, in which a glass slide is derivatized with a chemical species containing a photo-cleavable protecting group. Each site is sequentially deprotected by irradiation through a mask, and then reacted with a DNA monomer containing a photoprotective group. Methods for attaching a presynthesized probe onto a solid support include adsorption, ultra violet linking, and covalent attachment. In one example, the solid support is modified to carry an active group, such as hydroxyl, carboxyl, amine, aldehyde, hydrazine, epoxide, bromoacetyl, maleimide, or thiol groups through which the probe is attached (U.S. Pat. Nos. 5,474, 895 and 5,514,785).

The probing assay is typically conducted by contacting the array by a fluid potentially containing the nucleotide sequences of interest under suitable conditions for hybridization conditions, and then determining any hybrid formed. For example, mRNA or DNA in the sample is amplified in the presence of nucleotides attached to a suitable label, such as the fluorescent labels Cy3 or Cy5. Conditions are adjusted so that hybridization occurs with precise complementary matches or with various degrees of homology, as appropriate. The array is then washed, and bound nucleic acid is determined by measuring the presence or amount of label associated with the solid phase. Different samples can be compared between arrays for relative levels of expression, optionally standardized using genes expressed in most cells of interest, such as a ribosomal or house-keeping gene, or as a proportion of total polynucleotide in the sample. Alternatively, samples from two or more different sources can be tested simultaneously on the same array, by preparing the amplified polynucleotide from each source with a different label.

An exemplary method is conducted using a Genetic Microsystems array generator, and an Axon GenePix™ Scanner. Microarrays are prepared by first amplifying cDNA fragments encoding marker sequences to be analyzed in a 96 or 384 well format. The cDNA is then spotted directly onto glass slides at a density as high as >5,000 per slide. To compare mRNA preparations from two cells of interest, one preparation is converted into Cy3-labeled cDNA, while the other is converted into Cy5-labeled cDNA. The two cDNA preparations are hybridized simultaneously to the microarray slide, and then washed to eliminate non-specific binding. Any given spot on the array will bind each of the cDNA products in proportion to abundance of the transcript in the two original mRNA preparations. The slide is then scanned at wavelengths appropriate for each of the labels, the resulting fluorescence is quantified, and the results are formatted to give an indication of the relative abundance of mRNA for each marker on the array.

Identifying expression products for use in characterizing and affecting differentiated cells of this invention involves analyzing the expression level of RNA, protein, or other gene product in a first cell type, such as a pluripotent precursor cell, or a cell capable of differentiating along a particular pathway; then analyzing the expression level of the same product in a control cell type; comparing the relative expression level between the two cell types, (typically normalized by total protein or RNA in the sample, or in comparison with another gene product expected to be expressed at a similar level in both cell types, such as a house-keeping gene); and then identifying products of interest based on the comparative expression level.

Products will typically be of interest if their relative expression level is at least about 2-fold, 10fold, or 100-fold elevated (or suppressed) in differentiated pPS cells of this invention, in comparison with the control. This analysis can optionally be computer-assisted, by marking the expression level in each cell type on an independent axis, wherein the position of the mark relative to each axis is in accordance with the expression level in the respective cell, and then selecting a product of interest based on the position of the mark. Alternatively, the difference in expression between the first cell and the control cell can be represented on a color spectrum (for example, where yellow represents equivalent expression levels, red indicates augmented expression and blue represents suppressed expression). The product of interest can then be selected based on the color representing expression of one marker of interest, or based on a pattern of colors representing a plurality of markers.

Genes and proteins that undergo a change in expression level during differentiation are of interest for a number of purposes. For example, where expression is high in pPS cells and decreases during differentiation can be used as molecular markers of the undifferentiated state. Reagents corresponding to these markers, such as antibodies, can be used, for example, to eliminate undifferentiated pPS cells from a population of differentiated cells by immunoaffinity isolation or complement-mediated lysis. Where expression is increased during differentiation, the markers can be used in a similar manner to purify, enrich, remove or eliminate specific cell types derived from pPS cells. These markers may serve as indicators of broad classes of cell differentiation, such as genes or proteins expressed in mesodermal, endodermal or ectodermal lineages, or may serve as markers of highly differentiated cell types.

Genes that are upregulated during expression may also be useful to influence the differentiation of pPS cells into specific lineages. For instance, the forced expression in undifferentiated pPS cells of transgenes encoding transcription factors, growth factors, receptors and signaling molecules can be tested for an ability to influence differentiation into specific cell lineages.

Therapeutic Compositions

Differentiated cells of this invention can also be used for tissue reconstitution or regeneration in a human patient in need thereof. The cells are administered in a manner that permits them to graft to the intended tissue site and reconstitute or regenerate the functionally deficient area.

In one example, neural stem cells are transplanted directly into parenchymal or intrathecal sites of the central nervous system, according to the disease being treated. Grafts are done using single cell suspension or small aggregates at a density of 25,000–500,000 cells per $\mu$L (U.S. Pat. No. 5,968,829). The efficacy of neural cell transplants can be assessed in a rat model for acutely injured spinal cord as described by McDonald et al. (Nat. Med. 5:1410, 1999. A successful transplant will show transplant-derived cells present in the lesion 2–5 weeks later, differentiated into astrocytes, oligodendrocytes, and/or neurons, and migrating along the cord from the lesioned end, and an improvement in gate, coordination, and weight-bearing.

The efficacy of cardiomyocytes can be assessed in an animal model for cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac. Cardiovasc. Surg. 118:715, 1999). Successful treatment will reduce the area of the scar, limit scar expansion, and improve heart function as determined by systolic, diastolic, and developed pressure. Cardiac injury can also be modeled using an embolization coil in the distal portion of the left anterior descending artery (Watanabe et al., Cell Transplant. 7:239, 1998), and efficacy of treatment can be evaluated by histology and cardiac function. Cardiomyocyte preparations embodied in this invention can be used in therapy to regenerate cardiac muscle and treat insufficient cardiac function (U.S. Pat. No. 5,919,449 and WO 99/03973).

Hepatocytes and hepatocyte precursors can be assessed in animal models for ability to repair liver damage. One such example is damage caused by intraperitoneal injection of D-galactosamine (Dabeva et al., Am. J. Pathol. 143:1606, 1993). Efficacy of treatment can be determined by immunocytochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

Cells prepared according to this invention that are useful for human or veterinary therapy are optimally supplied in a pharmaceutical composition, comprising an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. The compositions may be packaged with written instructions for use of the cells in tissue regeneration, or restoring a therapeutically important metabolic function.

The examples that follow are provided by way of further illustration, and are not meant to imply any limitation in the practice of the claimed invention.

EXAMPLES

Example 1

Feeder-free Passage of hES Cells

In this experiment, undifferentiated hES cells that had been maintained on primary mouse embryonic feeder cells were harvested, and then maintained in the absence of feeders. The culture wells were coated with Matrigel®, and the cells were cultured in the presence of conditioned nutrient medium obtained from a culture of irradiated primary fibroblasts.

Preparation of Conditioned Media (CM) from Primary Mouse Embryonic Fibroblasts (mEF)

Fibroblasts were harvested from T150 flasks by washing once with $Ca^{++}/Mg^{++}$ free PBS and incubating in 1.5–2 mL trypsin/EDTA (Gibco) for about 5 min. After the fibroblasts detached from the flask, they were collected in mEF media (DMEM+10% FBS). The cells were irradiated at 4000 rad (508 sec at 140 kV: shelf setting 6 in a Torrex generator), counted and seeded at about 55,000 cells $cm^{-2}$ in mEF media (525,000 cells/well of a 6 well plate). After at least 4 hours the media were exchanged with SR containing ES media, using 3–4 mL per 9.6 cm well of a 6 well plate. Conditioned media was collected daily for feeding of hES cultures. Alternatively, medium was prepared using mEF plated in culture flasks, exchanging medium daily at 0.3–0.4 mL $cm^{-2}$. Before addition to the hES cultures, the conditioned medium was supplemented with 4 ng/mL of human bFGF (Gibco). Fibroblasts cultures were used in this system for about 1 week, before replacing with newly prepared cells.

Matrigel® Coating

Growth Factor Reduced Matrigel® or regular Matrigel® (Becton-Dickinson, Bedford Mass.) was thawed at 4° C. The Matrigel® was diluted 1:10 to 1:500 (typically 1:30) in cold KO DMEM. 0.75–1.0 mL of solution was added to each 9.6 $cm^2$ well, and incubated at room temperature for 1 h, or at 4° C. at least overnight. The coated wells were washed once with cold KO DMEM before adding cells. Plates were used within 2 h after coating, or stored in DMEM at 4° C. and used within ~1 week.

Human ES Culture

Undifferentiated hES colonies were harvested from hES cultures on feeders as follows. Cultures were incubated in ~200 U/mL collagenase IV for about 5 minutes at 37° C. Colonies were harvested by picking individual colonies up with a 20 μL pipet tip under a microscope or by scraping and dissociating into small clusters in conditioned medium (CM). These cells were then seeded onto Matrigel® in conditioned media at 15 colonies to each 9.6 $cm^2$ well (if 1 colony is ~10,000 cells, then the plating density is ~15,000 cells $cm^{-2}$).

The day after seeding on Matrigel®, hES cells were visible as small colonies (~100–2,000 cells) and there were cells in between the colonies that appeared to be differentiating or dying. As the hES cells proliferated, the colonies became quite large and very compact, representing the majority of surface area of the culture dish. The hES cells in the colonies had a high nucleus to cytoplasm ratio and had prominent nucleoli, similar to hES cells maintained on feeder cells. At confluence, the differentiated cells in between the colonies represented less than 10% of the cells in the culture.

Six days after seeding, the cultures had become almost confluent. The cultures were split by incubating with 1 mL ~200 U/mL Collagenase IV solution in KO DMEM for ~5 minutes at 37° C. The collagenase solution was aspirated, 2 mL hES medium was added per well, and the hES cells were scraped from the dish with a pipette. The cell suspension was transferred to a 15 mL conical tube, brought up to a volume of 6 mL, and gently triturated to dissociate the cells into small clusters of 10–2000 cells. The cells were then re-seeded on Matrigel® coated plates in CM, as above. Cells were seeded at a 1:3 or 1:6 ratio, approximately 90,000 to 170,000 cells $cm^{-2}$, making up the volume in each well to 3 mL. Medium was changed daily, and the cells were split and passaged again at 13 d and again at 19 d after initial seeding.

On day 19 after Initial seeding, cells were harvested and evaluated for surface marker expression by immunofluorescence cell cytometry, using labeled antibodies specific for cell surface markers. The results from this experiment are as follows:

TABLE 1

Phenotype of hES Cells
Grown in the Absence of Feeder Cells

| Marker | Specificity | Percentage of Cells Staining |
|---|---|---|
| SSEA-4 | undifferentiated cells | 92% |
| Tra-1-60 | undifferentiated cells | 92% |
| Tra-1-81 | undifferentiated cells | 83% |
| SSEA-1 | differentiated cells | 12% |

For the hES cells maintained in the absence of feeders, a high percentage express SSEA-4, Tra-1-60 or Tra-1-81. These 3 markers are expressed on undifferentiated human ES cells that are maintained on feeders (Thomson et al., 1998). In addition, there is very little expression of SSEA-1, a glycolipid that is not expressed(or expressed at low levels) on undifferentiated ES cells. Immunocytochemical evaluation of SSEA-4, Tra-1-60 and Tra-1-81 indicates that the expression of these markers is localized to the ES colonies, not the differentiated cells in between the colonies.

hES cells grown in the absence of feeder cells can be further characterized by karyotype (assessed by G-banding), expression of OCT-4 (a member of the POU transcription factor family associated with an undifferentiated ES cells, assessed by PCR), ability to form teratomas (1–4 months after injecting SCID/beige mice with $\sim 5 \times 10^6$ cells), and suitability for cryopreservation (in standard medium supplemented with 10% DMSO and 20–30% SR in a controlled rate freezer).

Cultures of hES cells have been grown in the absence of feeder cells for over 147 days after initial seeding, with no apparent change in the proliferative capacity or phenotype. Human ES cells maintained on Matrigel® in mEF conditioned medium have a doubling time of about 31–33 hours, similar to the proliferation rate for hES cells grown on mEF feeder cells. H1 cells after 64 days of feeder-free culture showed a normal karyotype.

Example 2

Matriael® and Laminin Support Feeder-free Growth of hES Cells

The growth of the hES cells has been followed on different matrix components, in medium conditioned using primary mouse embryonic fibroblasts (mEF).

hES cultures were initially harvested from feeder cell cultures maintained in ES medium (80% knockout DMEM (Gibco BRL, Rockville, Md.), 20% knockout serum replacement (Gibco BRL, Rockville, Md.), 1% Non-essential amino acids (Gibco BRL, Rockville, Md.), 1 mM L-glutamine (Gibco), 0.1mM β-mercaptoethanol (Sigma, St. Louis, Mo.), supplemented with 4 ng/mL recombinant human basic fibroblast growth factor (hbFGF; Gibco). Cultures were passaged by incubation in ~200 U/mL collagenase IV for about 5'–10 minutes at 37° C. Colonies are then harvested by removing individual colonies up with a Pipetman™ under a microscope or scraping, followed by gentle dissociation into small clusters in conditioned medium and then seeded onto matrix coated plates.

Harvested hES cells were seeded onto Matrigel® or gelatin in mEF conditioned medium. The day after seeding, cells plated onto Matrigel® attached to the plate and formed small colonies that were less compact than hES colonies on feeder layers. Over the next few days, the colonies increased in size and the cells became more compact. The resulting culture contained very dense undifferentiated colonies surrounded by differentiated cells.

About one week after seeding the cultures became confluent and could be passaged. In contrast, cells seeded onto gelatin showed poor survival and the cells that survived appeared differentiated. Three hES cell lines, H1, H7 and H9 were cultured on Matrigel® in mEF conditioned medium. Cultures maintained under these conditions for over 100 days continued to display ES-like morphology.

The major components of Matrigel® are laminin, collagen IV and heparin sulfate proteoglycan. The ability of these components to support hES cell culture was tested separately. Laminin, collagen IV or fibronectin (all from Sigma) were diluted to a final concentration of 20 μg/mL, 10 μg/mL and 5 pg/mL in PBS, respectively.

The hES cells seeded onto laminin, fibronectin or collagen IV had colonies of undifferentiated hES cells, although the cultures on fibronectin or collagen IV did not contain as many undifferentiated colonies as the cultures on Matrigel® or laminin. When cells on Matrigel® or laminin reached confluence, the cells within the colonies became very compact, were morphologically very similar to the cells maintained on feeders and were serially passaged. After 40 days (6 passages), cells on Matrigel® and laminin contained a high proportion of colonies which continued to display ES-like morphology in long term culture. However, cells maintained on fibronectin or collagen IV had fewer colonies displaying appropriate ES-morphology. As controls, cells cultured on Matrigel® or laminin in non-conditioned medium appeared to be proliferating more slowly and showed a differentiated morphology after a few passages.

FIG. 1 shows the morphology of hES cells in feeder-free culture. Panel A (Left Side) shows morphology of hES cells of the H1 line cultured on feeder cells in non-conditioned medium (mEF/RM), on Matrigel®, laminin, fibronectin, or collagen IV in mEF conditioned medium. Panel B shows morphology of hES cells of the H9 line maintained on Matrigel® in various types of conditioned medium, described in Example 11.

Laminins are major components of all basal laminae in vertebrates, which interact with integrin heterodimers, such as α1β1, α2β1, α3β1, α6β1, and α6β4, on cell surface and mediate cell growth and migration during development. Among these integrins, α6β1 and α6β4 are specific for laminins; other integrins also interact with other matrices. Another experiment tested whether laminin receptors are expressed on hES cells and whether culturing hES on laminin or Matrigel® changes the expression of laminin receptors expression. Expression of integrins including α1, α2, α3, α6, β1, and β4 were examined by FACS analysis on cells maintained on feeders, or on Matrigel® or laminin in conditioned medium. For analyzing integrin expression, cells were stained with a panel of integrin specific antibodies by the laminin-specific integrins investigator kit (Chemicon International, Inc., Temecula, Calif.) and analyzed by FACS as described below.

FIG. 1 Panel C shows integrin expression measured in H1 hES cells maintained on feeders in non-conditioned medium (mEF/RM) or on Matrigel®, or on laminin in mEF conditioned medium (CM).

Cells maintained in Matrigel®/conditioned medium and laminin/conditioned medium were cryopreserved as follows: The cells were frozen in standard hES medium (not conditioned medium) supplemented with 10% DMSO and additional 10% SR (total 30%). The cells were thawed onto Matrigel or laminin in conditioned medium. Cells maintained normal karyotype after being thawed.

Human ES cells maintained on Matrigel® in mEF conditioned medium showed a doubling time of about 31–33 hours, similar to the proliferation rate for hES cells grown on mEF feeder cells. H1 cells after 64 days of feeder-free culture showed a normal karyotype.

Example 3

Phenotypic Markers of hES Cells in Feeder-free Culture

Undifferentiated hES cells express SSEA-4, Tra-1-60, Tra-1-81, OCT-4, and hTERT. In order to assess whether the cells maintained in feeder-free conditions retained these markers, cells were evaluated by immunostaining, reverse transcriptase PCR amplification, and assay for telomerase activity.

FIG. 2 shows surface marker expression in feeder-free cells by FACS analysis. Panel A: Expression of SSEA-4 in H1 cells maintained on feeders in non-conditioned medium (mEF/RM), on Matrigel®, laminin, fibronectin and collagen IV in mEF conditioned medium. Isotype controls are indicated by the dotted lines. Panel B. Mean fluorescence intensity of SSEA-1, SSEA-4, Tra-1-60 and Tra-1-81 in H1 cells cultured on different matrices. Panel C: Mean fluorescence intensity of SSEA-1, SSEA-4, Tra-1 -60 and Tra-1 -81 in H9 cells cultured on Matrigel® in conditioned medium from different cell lines.

For analysis by fluorescence-activated cell sorting (FACS), the hES cells were dissociated in 0.5 mM EDTA in PBS and resuspended to about 5×10$^5$ cells in 50 µL diluent containing 0.1% BSA in PBS. For analyzing surface marker expression, cells were incubated in the primary antibodies, including IgG isotype control (0.5 µg/test), 1 gM isotype control (1:10), SSEA-1 (1:10), SSEA-4 (1:20), Tra-1-60 (1:40) and Tra-1-81 (1:80), diluted in the diluent at 4° C. for 30 min. After washing with the diluent, cells were incubated with rat anti-mouse kappa chain antibodies conjugated with PE (Becton Dickinson, San Jose, Calif.) at 4° C. for 30 min. Cells were washed and analyzed on FACSCalibur™ Flow Cytometer (Becton Dickinson, San Jose, Calif.) using CellQuest™ software.

Similar to the hES cells on feeders, cells on Matrigel®, laminin, fibronectin or collagen IV expressed SSEA-4, Tra-1-60 and Tra-1-81. There was very little expression of SSEA-1, a glycolipid that is not expressed by undifferentiated hES cells.

FIG. 3 shows marker expression detected by histochemistry. For analysis by immunocytochemistry, cells were incubated with primary antibodies, including SSEA-4 (1:20), Tra-1-60 (1:40) and Tra-1-81 (1:80), diluted in knockout DMEM at 37° C. for 30 min. Cells were then washed with warm knockout DMEM and fixed in 2% paraformaldehyde for 15 min. After washing with PBS, cells were incubated with 5% goat serum in PBS at RT for 30 min, followed by incubation with the FITC-conjugated goat anti-mouse antibodies (1:125) (Sigma) at RT for 30 min. Cells were washed, stained with DAPI and mounted. Cells were also examined for expression of alkaline phosphatase, a marker for undifferentiated ES cells. This was performed by culturing the cells on chamber slides, fixing with 4% paraformaldehyde for 15 min, and then washing with PBS. Cells were then incubated with alkaline phosphatase substrate (Vector Laboratories, Inc., Burlingame, Calif.) at room temperature in the dark for 1 h. Slides were rinsed for 2–5 min in 100% ethanol before mounting.

The results show that SSEA-4, Tra-1 -60, Tra-1 -81, and alkaline phosphatase were expressed by the hES colonies on Matrigel® or laminin, as seen for the cells on feeders—but not by the differentiated cells in between the colonies.

FIG. 4 shows OCT-4 and hTERT expression of H1 cells on feeders and off feeders, as detected by reverse-transcriptase PCR amplification. For radioactive relative quantification of individual gene products, QuantumRNA™ Alternate18S Internal Standard primers (Ambion, Austin Tex., USA) were employed according to the manufacturers instructions. Briefly, the linear range of amplification of a particular primer pair was determined, then coamplified with the appropriate mixture of alternate18S primers:competimers to yield PCR products with coinciding linear ranges. Before addition of AmpliTaq™ (Roche) to PCR reactions, the enzyme was pre-incubated with the TaqStart™ antibody (ProMega) according to manufacturers instructions. Radioactive PCR reactions were analyzed on 5% non-denaturing polyacrylamide gels, dried, and exposed to phosphoimage screens (Molecular Dynamics) for 1 hour. Screens were scanned with a Molecular Dynamics Storm 860 and band intensities were quantified using ImageQuant™ software. Results are expressed as the ratio of radioactivity incorporated into the hTERT or OCT-4 band, standardized to the radioactivity incorporated into the 18s band.

Primers and amplification conditions for particular markers are as follows. OCT-4: Sense (SEQ. ID NO:3) 5'-CT-TGCTGCAG MGTGGGTGG AGGAA-3'; Antisense (SEQ. ID NO:4) 5'-CTGCAGTGTG GGTTTCGGGC A-3'; alternate18:competimers 1:4; 19 cycles (94° 30 sec; 60° 30 sec; 72° 30 sec). hTERT: Sense (SEQ. ID NO:5) 5'-CGGM-GAGTG TCTGGAGCM-3'; Antisense (SEQ. ID NO:6) 5'-GGATGAAGCG GAGTCTGGA-3'; alternate18:competimers 1:12; 34 cycles (94° 30 sec; 60° 30 sec; 72° 30 sec).

The transcription factor OCT-4 is normally expressed in the undifferentiated hES cells and is down-regulated upon differentiation. In this experiment, it was found that the cells maintained on Matrigel® or laminin in conditioned medium (CM) for 21 days express OCT-4, whereas cells maintained in Matrigel® in unconditioned regular medium (RM) did not. Cells maintained on fibronectin or collagen IV, which showed a large degree of differentiation, expressed lower levels of OCT-4 compared to cells on feeders, Matrigel® or laminin.

hTERT and OCT-4 expression was seen in all the culture conditions except Matrigel® and regular medium. Furthermore, after exposure of cells to retinoic acid (RA) or dimethyl sulfoxide (DMSO), factors that promote cell differentiation, the expression of hTERT was markedly decreased.

FIG. 5 shows telomerase activity measured by TRAP assay (Kim et al., Science 266:2011, 1997; Weinrich et al., Nature Genetics 17:498, 1997). All the cultures conditions showed positive telomerase activity after 40 days on Matrigel®, laminin, fibronectin or collagen IV in mEF conditioned medium.

Example 4

In Vitro and in Vivo Differentiation

In vitro differentiation was induced in H1 hES cells maintained in conditioned medium on Matrigel®, laminin, fibronectin or collagen IV for 26 days. The hES cells were dissociated into small clumps by incubating in ~200 U/mL collagenase IV at 37° C. for 10 min, and cultured in suspension to form embryoid bodies (EBs) in medium containing DMEM, 20% FBS (Hyclone), 1 mM glutamine, 0.1 mM β-mercaptoethanol, and 0.1 mM non-essential amino acids (Gibco). After 4 days in suspension, the aggregates were transferred onto poly-ornithine-coated plates, and cultured for additional 7 days. The cultures were then examined for the presence of beating cells, and processed for immunocytochemistry.

FIG. 6 shows results of immunocytochemical analysis of these cells. The staining patterns were consistent with cells of the neuron and cardiomyocyte lineages (B-tubulin III and cardiac troponin 1, respectively). About 8 days after differentiation, beating regions were identified in all cultures. There were also cells staining for α-fetoprotein, a marker of endoderm lineage.

hES cells were also tested for their ability to form teratomas by intramuscular injection into SCID mice. Cells maintained on feeders or off feeders were harvested, resuspended in PBS and injected intramuscularly into SCID/beige mice ($5 \times 10^6$ cells per site). Tumors were excised and processed for histological analysis. The hES cells from feeder-free culture generated tumors, which were excised and processed for histological analysis after 78–84 days.

FIG. 7 shows the histopathology of teratomas derived from H7 cells maintained with mEF feeder cells (A), or in feeder-free culture (B). Mucinous epithelial component, cartilage and nerve tissue were observed in teratomas derived form hES cells cultured on feeders. Cystic epithelial structures, probable dental component, cartilage and glandular epithelial or neural components were found in teratomas derived from feeder-free hES cultures.

Example 5

Direct Differentiation of hES Cells

Differentiation using standard methods of aggregate formation was compared with a technique of this invention in which cells are differentiated by plating directly onto a solid surface under certain conditions.

For the aggregate differentiation technique, monolayer cultures of rhesus and human ES lines were harvested by incubating in Collagenase IV for 5–20 min, and the cells were scraped from the plate. The cells were then dissociated and plated in non-adherent cell culture plates in FBS-containing medium (20% non-heat-inactivated FBS (Hyclone), supplemented with 0.1 mM non-essential amino acids, 1 mM glutamine, 0.1 mM p-mercaptoethanol. The EBs were fed every other day by the addition of 2 mL of medium per well (6 well plate). When the volume of medium exceeded 4 mL/well, the EBs were collected and resuspended in fresh medium. The plates were placed into a 37° C. incubator, and in some instances, a rocker was used to facilitate maintaining aggregates in suspension. After 4–8 days in suspension, aggregate bodies formed and were plated onto a substrate to allow for further differentiation.

For the direct differentiation technique, suspensions of rhesus and human ES cells were prepared in a similar fashion. The cells were then dissociated by trituration to clusters of ~50–100 cells, and plated onto glass coverslips treated with poly-ornithine. The cells were maintained in serum containing medium, or defined medium for 7–10 days before analysis. Cells were tested by immunoreactivity for β-tubulin III and MAP-2, which are characteristic of neurons, and glial fibrillary acidic protein (GFAP), which is characteristic of astrocytes.

Six different ES lines differentiated into cells bearing markers for neurons and astrocytes, using either the aggregate or direct differentiation technique. In cultures derived from rhesus ES cells, percentage of aggregates that contained neurons ranged from 49% to 93%. In cultures derived from human ES cells, the percentage of aggregates containing neurons ranged from 60% to 80%. Double labeling for GABA and β-tubulin indicated that a sub-population of the neurons express the inhibitory neurotransmitter GABA. Astrocytes and oligodendrocytes were identified with GFAP immune reactivity and GalC immune reactivity, respectively. Therefore, the human and rhesus ES cells have the capacity to form all three major cell phenotypes in the central nervous system.

The effect of several members of the neurotrophin growth factor family was examined. hES cells were differentiated by harvesting with collagenase, dissociating, and reseeding onto poly-ornithine coated cover slips. The cells were plated into DMEMW/F12+N2+10% FBS overnight. The following day, the serum was removed from the medium and replaced with 10 ng/mL human bFGF and the growth factor being tested. After 24 hours, bFGF was removed from the medium. These cultures were fed every other day. They were fixed after 7 days of differentiation and immunostained for analysis. The number of neurons was evaluated by counting cells positive for β-tubulin. Cultures maintained in the presence of 10 ng/mL brain derived neurotrophic factor (BDNF) formed approximately 3-fold more neurons than the control cultures. Cultures maintained in neurotrophin-3 (1 ng/mL) formed approximately 2-fold more neurons than control cultures.

To assess cardiomyocyte formation, EBs were transferred to gelatin-coated plates or chamber slides after 4 days in the suspension cultures. The EBs attached to the surface after seeding, proliferated and differentiated into different types of cells. Spontaneously contracting cells were observed in various regions of the culture at differentiation day 8 and the number of beating regions increased until about day 10. In some cases, more than 75% of the EBs had contracting regions. Beating cells were morphologically similar to mouse ES cell-derived beating cardiomyocytes. In these cultures 100% of the contracting areas were immunoreactive with cardiac troponin I (cTnI), while minimal immunoreactivity was observed in the non-beating cells.

Cultures of differentiated EBs were subjected to Western blot analysis using monoclonal antibody against cTnI. This assay gave a strong 31 kDa protein signal, corresponding to the size of the purified native human cTnI. It was detected in differentiated human ES cells containing contracting cells, but not in undifferentiated ES cells or differentiated cultures with no evidence of contracting cells. As a control, the blot was reprobed with β-actin specific antibody, confirming the presence of similar amounts of proteins in all samples.

In other experiments, EBs were cultured for 8 or 16 days and maintained as adherent cultures for an additional 10 days. RNA was prepared from the differentiated human ES cells and semiquantitative RT-PCR was performed to detect the relative expression of the endoderm-specific products $\alpha_1$-anti-trypsin, AFP, and albumin. Low levels of $\alpha_1$-anti-trypsin and AFP were detected in the undifferentiated cultures; little or no albumin was detected in the same cultures. All 3 markers were detected at significantly higher levels after differentiation. Expression of all 3 endoderm markers was higher in cultures derived from 8 day embryoid bodies than 16 day embryoid bodies.

Example 6

Microarray Analysis of Expression by Undifferentiated and Differentiated Cells

An analysis of differential gene expression was performed by contrasting mRNA from undifferentiated H9 cultures with mRNA from corresponding EBs. The EBs were maintained in growth medium for 8 days, or kept in growth medium for 4 days, followed by 4 days of treatment with 0.5 µM retinoic acid. EBs were harvested after 2d, 4d, or 8d and the resulting mRNA was compared directly with mRNA from undifferentiated cultures. This analysis tracks the transformation of a relatively homogenous cell population into a complex mix of differentiated cell types, and thus the readouts are affected both by the magnitude of the change in gene expression, and, in the case of expression changes specific to a differentiated cell type, by the representation of that cell type in the culture. The arrays used in these experiments sample approximately 10,000 cDNAs selected to represent a large portion of characterized human genes.

Total RNA was harvested from human ES cultures or their differentiated derivatives using the Qiagen RNAeasy™ Miniprep kit according to the manufacturer's instructions. RNA was quantified by measuring ultraviolet absorption at 260 nm. Poly A$^+$ mRNA was prepared from the total RNA preparations using Qiagen Oligotex™ Minipreps according to the instructions of the manufacturer. Final mRNA preparations were quantified by $A_{260}$ measurements, then visually inspected following electrophoresis on native agarose gels. Sample RNAs were sent to a contract laboratory (Incyte Pharmaceuticals, Palo Alto, Calif.) for conversion into Cy3- or Cy5 labeled cDNA probe, which was subsequently hybridized to UNIGEM 1.0 arrays.

Following processing of the hybridized arrays, fluorescence measurements were quantified and the results returned for analysis. Probe pairings were performed with samples from undifferentiated ES cells in the Cy3 channel, and the differentiated ES cell samples in the Cy5 channel. A change in expression (as measured by comparing the Cy3 and Cy5 channels) was generally considered significant if the difference was at least 2.5-fold.

The differentiation of hES cells involves the activation and repression of many genes, including ESTs with no known function. Interestingly, the addition of retinoic acid to the suspension culture for the final 4 days of differentiation had relatively minor effect on the gene expression pattern (compare 4d−/4d+ with 8d).

Genes whose expression is reduced during differentiation sample a wide range of functions, including metallothioneins, growth factors (e.g., FGF9), secreted cysteine-rich proteins (e.g., osteopontin, AGF-BP5, Cyr61, connective tissue growth factor), the selenium donor protein selD, and many others. In general, the most significant alterations in expression occur after 4 days of suspension culture, and correspond with the onset of changes in cell morphologies. Of interest, the expression of two genes involved in the catabolism of α-D-Glucose phosphate, UDP-glucose phosphorylase and phophoglucomutase, are dramatically reduced upon differentiation, suggesting a potential alteration in glucose metabolism.

The arrays used in these experiments do not contain cDNA features corresponding to hTERT; however, a marked decrease in the expression of the mRNA for TRF1 was observed. TRF1 is a principal telomere binding factor whose expression has been correlated with a shortening of telomere lengths. Thus, the expression of both positive (hTERT) and negative (TRF1) regulators of telomere length is reduced during ES cell differentiation.

Several genes associated with visceral endoderm and early hepatic differentiation were predominant in this analysis, including α-fetoprotein, apoplipoprotein A-II, apoplipoprotein AI regulatory protein-1, $α_1$-antitrypsin, and the α, β, and γ chains of fibrinogen. This induction is apparent within 2 days of differentiation, and is not substantially affected by retinoid treatment. The induced expression of cellular retinoic acid binding proteins 1 and 2 (CRABP I, II) is not observed in retinoid treated cultures, consistent with a proposed negative feedback loop in which retinoids specifically inhibit the transcription of the promoter of the CRAB I gene.

Expression of the IL-6 receptor gp130 is low in hES cultures, and is induced upon differentiation. These results provide a molecular basis for the lack of LIF responsiveness in hES cultures (Thomson et al., 1999; Reubinoff et al., 2000) and indicate a substantially different role for gp130 in human vs. mouse ES cells, where LIF signaling is directly implied in the maintenance of the undifferentiated state.

Other differentiation-induced genes include the protein homologs pleiotropin and midkine. These secreted cytokine have proposed roles as mitogens for neuronal and hepatic cell types, or as generalized angiogenic factors (Owada et al., 1999; Sato et al., 1999), and as such may play a similar role in ES cell differentiation. The induction of DNA binding proteins, such as homeobox b5 protein and meis1, likely reflects the central role of transcriptional regulators in differentiation processes.

Example 7

Genetic Alteration of hES Cells Maintained on Primary mEF Feeder Layers

This example provides conditions for introducing genetic alterations into hES cells grown on primary mEFs as already described. Before transfecting, hES cells were removed from the feeder layer with collagenase (~200 units/mL), suspended in a final volume of 18 mL, and plated at 3 mL/well in 6 well plates pre-coated with gelatin and primary mEF feeder cells.

The replated cells were then tested with different transfection systems, including: Mammalian Transfection Kit (CaPO4 and DEAE reagents), Stratagene cat # 200285; TransIT-LT1 Mirus (Panvera), cat # MIR 2310; Polybrene (Sigma); Poly-L-Lysine (Sigma); Superfect™ (Qiagen); Effectene™ (Qiagen); Lipofectin™ (Life Technologies); Lipofectamine (differs from Lipofectamine 200™) (Life Technologies); Cellfectin™ (Life Technologies); DMRIE-C (Life Technologies); Lipofectamine 2000 (Life Technologies); and electroporation using BioRad™ Gene pulser.

Under the conditions used, Lipofectamine 2000™ (Gibco Life Technologies cat # 11668019, patent pending) and FuGENE™ (trademark of Fugent L.L.C.; a proprietary blend of lipids and other components, purchased from Roche Diagnostic Corporation cat #1 814 443) both resulted in good transfection efficiency. The efficiency was generally best if these reagents were contacted with replated hES cells ~48 h after the replating.

Transfection using Lipofectamine 2000™ was conducted as follows: The plasmid DNA (3–5 µg of pEGFP-C1, ClonTech cat. # 6084-1) was diluted in water to a final volume of 100 µl. In pilot experiments, 5 to 30 µL of Lipofectamine 2000™ (Gibco, cat # 11668-019) were diluted in OptiMEM™ (Gibco, cat # 11-58-021) to a final volume of 100 µL. The DNA solution was then added slowly to the Lipofectamine2000™ solution and mixed gently. The mixture was incubated at room temperature for 20–30 min before being supplemented with 800 µl of OptiMEM™. Cells were washed with 3 mL of pre-warmed OptiMEM™ and incubated in 0.5–1 mL of the DNA/lipid mixture solution at 37° C. for 4 h, per well (9.6 cm$^2$). In some experiments, at 4 h the complex was removed before the addition of 4 mL of mEF-conditioned medium; in others sufficient mEF-conditioned medium was added to the wells to reach a final volume of 3.5 mL and the mixture was left on the cells overnight. In other experiments the DNA:lipid mixture was added to wells containing sufficient mEF-conditioned medium such that the final volume was 3.5 mL, and the cells were incubated in this mixture overnight.

Transfection using FuGENE™ was conducted as follows. Each well was transfected with 10 µg DNA using FuGENE™ 6 (Roche Diagnostics Corp.), at a ratio of 3:2 FuGENE™ reagent to DNA as described by the manufacturer's directions. OptiMEM™ serum-free medium was used in the transfections. In the "old protocol", 4 h after the addition of the FuGENE™-DNA complex, 2.5 mL of standard hES medium was added to each transfected well. In the revised protocol ("3:2 L"), transfected wells were not re-fed with standard hES medium. Twenty-four hours after transfection, GFP-expression was assessed by flow cytometry.

Forty-eight hours before transfection, hES cells were seeded onto 6 well plates that had been coated with gelatin and mEF feeder layers as described above. hES cells were transfected using FuGENE™ 6 (Roche) or Lipofectamine 2000™ (Gibco) according to the manufacturers' instructions. Twenty-four hours after transfection, cells were assessed for GFP expression by inspection under a fluorescent microscope or flow cytometry. In the experiment shown in FIG. 1, three methods were compared: the standard Lipofectamine 2000™ protocol, the standard FuGENE™ protocol, and a variant FuGENE™ protocol in which the DNA/lipid mix was left on the cells overnight. The results demonstrated that while Lipofectamine 2000™ consistently yielded a higher percentage of GFP-expressing cells, the variant FuGENE™ protocol resulted in GFP-expressing cells with a higher mean fluorescence intensity.

Transient transductions using adenoviral vectors were conducted as follows. The vector Ad5CMV5-GFP (referred to here as Ad5GFP) contains the green fluorescent protein encoding region under control of the CMV promoter, and was purchased from Quantum Biotechnologies, cat # ADVO030. Seventy-two hours before transduction, hES cells were seeded onto 24 well plates that had been coated with gelatin and mEF feeder layers as described above. Before transduction, 3 wells of hES cells were detached with a solution of 0.05% trypsin/5 mM EDTA (Sigma) at 37°, resuspended in 500 µL of standard mEF growth medium, and counted with a hemocytometer (the 75,000 mEF feeder cells were subtracted from each well) to establish the cell number before transfection. The adenovirus stock was thawed on ice immediately prior to use.

For infection with Ad5GFP, growth media was aspirated from the wells containing hES cells and replaced with 1 mL of hES medium plus 9 µL of Ad5 GFP stock (MOI of 40). Two hours later, the virus-containing medium was replaced with 1 mL of hES medium per well. Each transduced well was refed with 1 mL of fresh hES medium every 24 hours. GFP expression was assessed by flow cytometry. The results from a typical experiment indicated that expression was highest at 24 hr after transduction but persisted for at least 8 days at low levels (by the later time points, extensive differentiation had occurred due to overgrowth of the hES cells).

FIG. 8 shows FACS analysis of hES cells plated on feeder layers and infected 48 h later with either the adenoviral vector Ad5GFP (MOI of 30) or the retroviral vector GRN354 (MOI of 40, Example 9). After 24 h 48 h respectively, the cells were harvested, stained with an antibody against the stem cell marker SSEA-4, and assessed for GFP expression by flow cytometry. Upper panels show the background fluorescence and SSEA-4 positive staining in mock-infected cultures. Lower panels show the level of green fluorescence resulting from expression of the GFP.

Example 8

Preparation of Immortalized Feeder Cells

Primary mouse embryonic fibroblasts (Robertson, supra) can be immortalized by genetically altering them to express human telomerase reverse transcriptase (hTERT). The fibroblasts (mEF) are infected with a retroviral construct pBABE puro hTERT, containing the hTERT coding sequence driven by the MoLV LTR and the puromycin-resistance gene driven by the SV40 early promoter. Isolates of primary mEFs are cultured in growth medium containing 10% fetal calf serum (HyClone), 2 mM glutamine (Gibco/BRL), and 90% high glucose DMEM (Gibco/BRL). mEFs are split every 3 days at a ratio of 1:2.

After 4 such splits, $5 \times 10^5$ mEFs are plated onto a 100 mM dish. On the next day, cells are infected by replacing the growth medium with a mixture containing 5 mL of retroviral stock ($1 \times 10^6$ pfu/mL) and 4 µg/mL polybrene, and incubating at 37° C. After 8 h, an additional 5 mL of the retrovirus/polybrene mixture is added and the cells are incubated at 37° C., On the next day, the retrovirus/polybrene mixture is removed and replaced with fresh growth medium. After 4 hr, the mEFs are removed from the plate with 0.5% trypsin/500 mM EDTA (Gibco/BRL) and replated into 2 T150 flasks in 25 mL growth medium/flask. On the next day, the medium is replaced with growth medium supplemented with 0.5 micrograms/mL puromycin.

Cells are split once a week at a ratio of 1:4 for 8 weeks and maintained in puromycin-containing medium. After 8 weeks, cells are trypsinized and replated at a density of 2,000 cells per 150 mm plate. Individual colonies are isolated with cloning cylinders 26 days later, expanded, and screened for telomerase activity.

Mouse Feeder Cell Line NH190

A permanent mouse cell line has been established that is suitable for conditioning medium for the culture of primate pluripotent stem (pPS) cells. The NHG190 line is a mouse embryonic fibroblast cell line immortalized with telomerase that is triple drug resistant, and expresses green fluorescent protein (GFP).

Two mouse strains were obtained from Jackson Laboratory (Bar Harbor, Me.) that have a transgene for resistance to the antibiotics neomycin or hygromycin. The C57BU6J TgN(pPGKneobpA)3Ems mice and C57BU6J-TgN (pPWL512hyg)1 Ems mice from Jackson Labs were crossbred. Embryos that were both neomycin- and hygromycin-resistant were dissected at day 13.5 post conception according to standard protocols for preparing mouse embryonic fibroblasts (mEF) for feeder layers (E. J. Robertson, pp. 71–112 in *Teratocarcinoma and Embryonic Stem Cell Lines*, ed. E. J. Robertson, Oxford: IRL Press, 1987). The derived mEF cells were stored frozen.

The mEFs were thawed in growth medium containing 20% fetal calf serum (Hyclone), 2 mM L-glutamine (Gibco/BRL), 80% DMEM (Gibco/BRL). The cells were expanded using 1:2 split ratios for 4 passages. Two flasks that had reached ~75% confluence were fed with fresh medium 4 h before electroporation. Cells were removed from the flasks with 0.5% trypsin/500 mM EDTA (Gibco/BRL), pelleted at 400×g for 5 min at room temperature, and resuspended in the growth medium at a concentration of $4 \times 10^6$ cells/mL.

The cell suspension was divided into two 500 µL aliquots and transferred to two 0.4 cm gap electroporation cuvettes (BioRad). One cuvette received 5 µg of the control plasmid (pBS212; puromycin-resistance gene driven by the SV40 early enhancer/promoter); the other received 5 µg of pGRN190, comprising the murine telomerase reverse transcriptase (mTERT) coding region driven by MPSV promoter plus purotnycin resistance gene driven by the SV40 early enhancer/promoter. The cells and DNA were mixed by hand, and electroporated using a BioRad gene Pulser with a BioRad capacitance extender at a setting of 300V, 960 µF.

Each aliquot of cells was transferred to an individual 150 cm plate containing 25 mL of growth medium. The medium on the plates was exchanged on the following day, and on the next day, growth medium was replaced by growth medium plus 0.5 µg/mL puromycin. The medium on the plates was exchanged for fresh puromycin-containing medium every 48 hrs until 29 days after electroporation. At this time, large individual colonies of puromycin-resistant cells were evident in both the pBS212- and pGRN190-electroporated plates. Ten colonies from the control plate and 12 from the pGRN190-electroporated plate were isolated with cloning cylinders and each colony was transferred to 1 well of a 48-well plate (1 well per colony).

One week later, all surviving colonies that had expanded to reach confluence in the 48 well plate (three control colonies, 1 pGRN190-electroporated colony) were transferred individually to wells of a 24 well plate. Six days later, the only colony that had continued to expand was derived from the pGRN190-electroporated plate, and was subsequently designated NH190. The cells were maintained in growth medium plus 0.5 µg/mL puromycin. Analysis for telomerase activity by TRAP assay (Kim et al., Nucleic Acids Res. 25:2595, 1997) demonstrated that NH190 cells express functional telomerase activity.

To facilitate monitoring of the cells in mixed culture populations and in vivo, NH190 cells were further infected with a retroviral construct conferring expression of green fluorescent protein (GFP). The enhanced GFP sequence from plasmid pEGFP-1 is one of the Living Colors™ fluorescent protein vectors, available from ClonTech. It contains an enhanced GFP encoding region, with changes that alter restriction nuclease cleavage sites, and shift the excitation and emission wavelengths of the encoded protein. The EGFP-1 sequence was cloned into the vector pMSCV-.neo, ClonTech cat # K1062-1. NH190 cells were transduced with the engineered vector, and GFP positive cells were separated by FACS sorting. The GFP expressing cell line was designated NHG190. These cells have been carried in culture for over 3 months.

Example 9

Genetic Alteration of hES Cells Maintained on the Drug-resistant NHG190 Feeder Cell Line NHG190 cells described in Example 8 were cultured in DMEM (Gibco) plus 20% fetal bovine serum (HyClone) and 5 mM glutamine. Cells were split 1:10 every 3 days. Subconfluent cultures were detached with trypsin, suspended in 10 mL medium, and irradiated with a cumulative dose of 3500 rads with a Torrex 150D X-ray generator. Irradiated cells were pelleted at 400×g for 5 min and resuspended at $1.25 \times 10^5$ cells per mL in either NHG190 medium or standard hES medium.

hES cells were transfected by replating on a 6-well plate precoated with Matrigel® and NHG190 feeder cells. Forty-eight hours after seeding, the hES cells were transfected with 10 µg DNA per well using FuGENE™ 6 (Roche) according to manufacturer's protocol in OptiMEM™ serum-free medium. The DNA was a plasmid containing the PGK promoter driving neor. Four h later, 3 mL of NHG190-conditioned medium was added to each transfected well. Cells were re-fed daily with 3 mL conditioned medium. Forty-eight h after transfection, the cells were layered with NHG190 conditioned medium containing 200 µg/mL added geneticin (Sigma), which was replaced daily thereafter. After 3 days of selection, additional irradiated NHG190 feeder cells were added ($1.25 \times 10^5$ cells/well in hES medium). Twenty-four h later, the medium was again replaced with NHG190-conditioned medium containing 200 µg/mL geneticin, replaced daily.

Individual colonies were isolated and expanded through another round of selection. After a further 5 days, individual colonies were identified by microscope and marked on the outside of the dish. Medium was removed, and replaced with collagenase (~200 U/mL). Individual colonies were picked using a p20 pipet tip, and transferred to individual tubes containing 2 mL NHG190 conditioned medium (without geneticin). The suspension was triturated 5 times to disaggregate colonies, and the contents of each tube were transferred to a well of a 12-well plate coated with gelatin and irradiated NHG190 cells ($1.875 \times 10^5$ cells/well). Cells were fed 24 h later with 2 mL fresh conditioned medium. Two days after seeding, cells were layered with 2 mL conditioned medium containing 200µg/mL geneticin, replaced daily for 5 days. As each well became 50–75% confluent, the cells were detached with collagenase, transferred to 6 mL conditioned medium, and triturated 10–12 times. 3 mL cell suspension was added to each of 2 wells of a 6-well plated coated with gelatin and irradiated NHG190 cells ($3.75 \times 10^5$ cells/well); the cells were refed with 3 mL conditioned medium at 24 h. The cells were then selected for 5 days using 3 mL conditioned medium containing geneticin, and split 1:6 as before.

Stable transduction using retrovirus was conducted as follows. Retroviral vector designated GRN354 was constructed at Geron Corp. using PMSCVneo vector purchased from ClonTech (cat # K1062-1). The eGFP encoding region was inserted downstream from the MSCV LTR. The LTR drives expression of GFP, and the vector also contains the neo gene driven by the murine PGK promoter. Plates were coated with 0.5% gelatin and NHG190 feeder cells ($7.5 \times 10^4$ in 1 mL NHG190 medium for 24 well plates; $3.75 \times 10^5$ in 3 medium for 6 well plates). The hES line H7 was seeded onto a 24 well prepared plate in hES medium (1 mL/well). Forty-eight h later, 3 wells of hES cells were detached using 0.05% trypsin/5 mM EDTA (Sigma) at 37° C., resuspended in 500 µL NHG190 medium, and counted. Stock of retrovirus construct pGRN354 was thawed on ice immediately prior to use. Growth medium was aspirated from the wells and replaced with 400 µL hES medium plus 8 µL retrovirus (MOI of 10) and 4 µL of 8 mg/mL polybrene solution (Sigma). Two h later, 800 µL hES medium were added per well. Each transduced well was refed with 1 mL fresh hES medium every 24 h.

Four days after transduction, medium was replaced with 1 mL hES medium containing 200 µg/mL geneticin. After 3 days of geneticin selection, the cells were detached with collagenase, triturated, resuspended in 3 mL hES medium, reseeded into one well of a 6-well plate coated with gelatin and NHG190 feeders, and refed with hES medium after 24 h. The medium was then again replaced with hES medium containing geneticin and refed every 24 h. Undifferentiated colonies survived the selection, and have been maintained for over 3 months. FACS analysis showed that 50–65% of the selected cells express GFP, albeit at low levels. The karyotype of the cells was normal.

The cells were then transferred to suspension culture to form embryoid bodies, allowed to differentiate for 4 days, and then plated in 20% FBS medium for 1 week. After extensive differentiation occurred, the cultures were fixed in 4% paraformaldehyde and prepared for fluorescence microscopy. Many of the differentiated cells expressed higher levels of GFP than the undifferentiated transfected hES cell line, consistent with differential activation of the MESV-LTR in different cell types.

Example 10

Transfection of hES Cells in Feeder-free Culture hES cells maintained in feeder-free culture on laminin in conditioned medium were genetically modified by transfecting with a plasmid carrying green fluorescent protein (GFP) driven by the CMV promoter.

mEF conditioned medium was prepared as described earlier. mEFs were irradiated and seeded at about $5.7 \times 10^4$ cells cm$^{-2}$. After at least 16 hours the medium was exchanged with hES medium including 4 ng/mL added hbFGF. Conditioned medium was collected daily for feeding of hES cultures. Before addition to the hES cultures, this medium was supplemented with an additional 4 ng/mL of hbFGF. Where needed for selection of stable transfectants, the mEF-conditioned medium was supplemented with 200 µg/mL geneticin (Sigma cat. #G5013).

H9 hES cells maintained on mEF feeder layers were harvested from cultures by incubation with ~200 units/mL collagenase IV at 37° C. for 10 min. Cells were dissociated and resuspended in regular hES medium or mEF-conditioned medium. Cells in the regular medium were then re-seeded onto mEF feeder layers and cells in the mEF-conditioned medium were plated onto Matrigel® or laminin. Seeding density for all cultures was approximately $4 \times 10^4$ cells/cm$^2$. Cells on feeder layers were maintained in regular medium while cells on matrices were maintained in mEF-conditioned medium for 1 or 2 days before the transfection. Conditioned medium was replaced every 24 h.

hES cell cultures were transfected with Lipofectamine 2000™ as described above. FACS analysis of GFP expression was conducted as follows. hES cells were harvested using 0.5mM EDTA in PBS and resuspended at approximately $1 \times 10^6$ cells/test. Cells were washed in a solution containing PBS plus 2% FBS, 0.1% sodium azide, and 2 mM EDTA. SSEA-4 staining was performed in the same buffer using antibody obtained from the Developmental Studies Hybridoma Bank (University of Iowa, Iowa City) at 1:15 dilution. Isotype matched controls were obtained from Sigma, (St. Louis Mo., USA). Cells were incubated with antibodies in a final volume of 100 µl for 30 min at 4° C., washed and incubated with rat anti-mouse K chain antibodies conjugated with PE (Becton Dickinson, San Jose, Calif.) at 4° C. for 30 min. Samples were washed as before and analyzed for GFP and SSEA-4 expression on FACScalibur™ flow cytometer (Becton Dickinson, San Jose, Calif.) using CellQuest™ software.

hES cells of the H9 line maintained on laminin in mEF-conditioned medium were transfected with a plasmid carrying GFP driven by the CMV promoter at 24 or 48 h after plating. Initial experiments used a mixture of 5 µg of plasmid and 12 µL of Lipofectamine 2000™. Cells received 1 mL of DNA/lipid complex and were incubated for 4 h at 37° before the addition of 3 mL of mEF-conditioned medium, and then monitored for GFP expression 24 h after transfection.

FIG. 9 shows the results of this experiment. Panel A: morphology of H9 cells maintained on laminin. Panel B: GFP-positive cells observed in the same colony shown in A. Panel C: FACS analysis of % GFP-positive cells in SSEA-4 high population(undifferentiated cells). Cells were transfected 24 (bar 1 and 2) or 48 h (bar 3 and 4) after the seeding and analyzed 24 (bar 1 and 3) or 48 h (bar 2 and 4) after the transfection. Bright green cells were observed in compact areas of undifferentiated ES colonies on laminin 24 h after transfection (Panels A & B). Transfection at 48 h after initial seeding gave the highest efficiency: 38% of the cells were GFP-positive as determined by FACS analysis 24 h after the transfection (Panel C).

The next experiment compared the transfection efficiency of H9 cells maintained on Matrigel® or laminin-coated plates in mEF-conditioned medium with cells maintained on mEF feeders. Cells on feeder layers maintained in regular medium were used as a control. Morphological differences between cells on feeders and cells off feeders were observed 1 or 2 days after seeding. Colonies on feeders were more compact than cells maintained off feeder layers; individual hES cells in feeder-free cultures were less compact and flatter. There was no significant difference in cell or colony morphology between cells on laminin and cells on Matrigel. These cells were transfected with a plasmid expressing GFP driven by the CMV promoter 2 days after seeding. Twenty-four hours after the transfection, cells were examined for GFP expression under a fluorescence microscope.

Figure 10A:
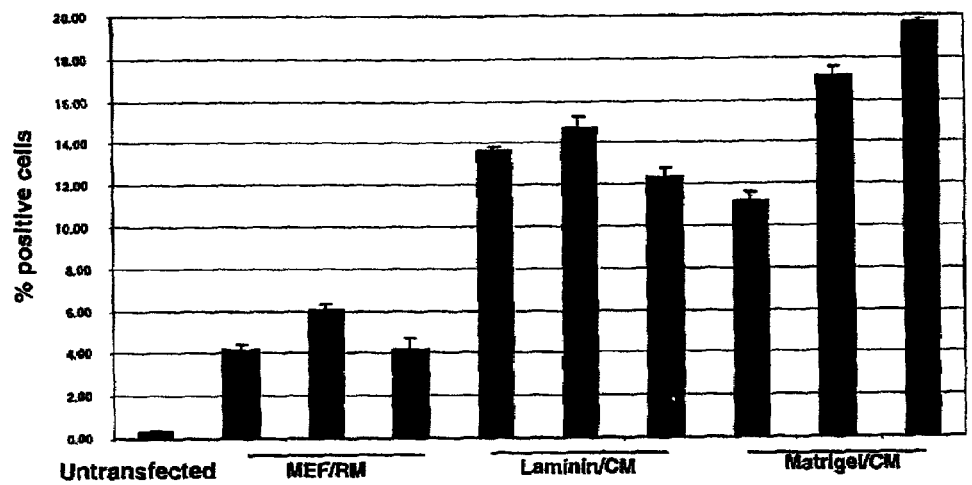

The cells were maintained on mEF feeders in regular medium (mEF/RM), on laminin in medium conditioned by mEF (Laminin/CM) or on Matrigel® in the conditioned medium (Matrigel/CM). As shown in FIG. 10(A), bright green cells were observed in undifferentiated hES colonies of feeder-free cultures. In contrast, very few green cells were found in colonies on feeders. FACS analysis showed that 16% of cells on Matrigel® and 14% of cells on laminin were GFP positive in SSEA-4 high population while only 5% of cells on feeders were positive. These results indicate that transfection efficiency is significantly increased by using feeder-free conditions.

The next experiments evaluated the effects of 1) the ratio of DNA:lipid; 2) adding the DNA/lipid complex to cells 4 h prior to the addition of mEF-conditioned medium vs. addition of the complex to cells in the presence of mEF-conditioned medium; and 3) use of Lipofectamine 2000™ vs. FuGENE™.

Transfection using Lipofectamine2000™ is described above. Transfection with FuGENE™ was conducted as follows. The plasmid DNA (5–10 μg of pEGFP-C1, Clon-Tech cat. # 6084-1) was diluted in water to a final volume of 100 μl. In pilot experiments, 5–30 μL of FuGENE™ were added to sufficient OptiMEM™ to achieve a final volume of 100 μL. The DNA solution was then added slowly to the FuGENE™ solution and mixed gently. The mixture was incubated at room temperature for 30 min before being supplemented with 800 μl of OptiMEM™. Cells were washed with 3 mL of pre-warmed OptiMEM™ and incubated in 1 mL of the DNA/lipid mixture solution at 37° C. for 4 h. In some experiments, at 4 h the wells received an additional 2 mL of mEF-conditioned medium; in others the DNA/lipid mixture was added to wells containing 2 mL of mEF-conditioned medium and the cells were incubated in this mixture overnight.

Figure 10B:
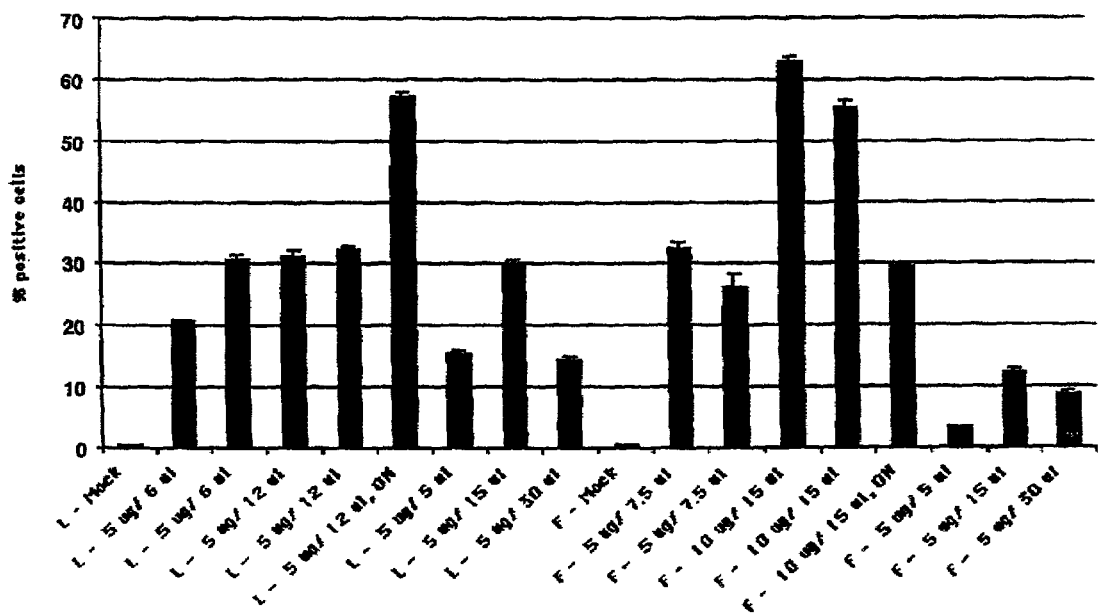

The results are shown in FIG. 10(B). Highest efficiencies were obtained under the following conditions: Bar 1=a mixture of 5 μg plasmid plus 12 μl of Lipofectamine 2000™, adding 1 mL of the DNA/lipid mixture to wells containing 2.5 mL of mEF-conditioned medium and incubating the cells in this mixture overnight. Bars 2 & 3=a mixture of 10 μg plasmid plus 15 μl of FuGENE™ and incubating the cells in 1 mL of the DNA/lipid mixture for 4 h before adding 2.5 mL of mEF-conditioned medium. L=Lipofectamine2000™; F=FuGENE™.

In another series of experiments, hES cells were transfected after being detached from the matrix in feeder-free culture using a solution of 0.5 mM EDTA in sterile PBS (instead of collagenase). Cells were incubated for 5 min at 37° C., until individual cells began to round up. The EDTA solution was then removed, and ~1 mL of conditioned medium was pipetted into the well, detaching the cells. The resultant clusters were then replated in a new feeder-free culture at a split ratio of 1:3 or 1:6. Under these conditions, the highest transient transfection efficiency was achieved when the cells were lipofected 24 h after seeding.

To investigate whether the feeder-free hES cells undergo stable genetic modification, H1 hES cells maintained on Matrigel® were cotransfected with a mixture of 7.5 μg plasmid carrying β-galactosidase driven by the EF1a promoter, and 2.5 μg of plasmid carrying the PGK promoter driving the neophosphotransferase gene. The cells were transfected 48 h after plating them on Matrigel® in mEF-conditioned medium. 10 μg of plasmid plus 15 μl of FuGENE™ were incubated with the cells in 1 mL for 4 h before adding 2.5 mL of mEF-conditioned medium. After 48 h, medium was exchanged for mEF-conditioned medium supplemented with 200 μg/mL geneticin. Cultures were maintained in this geneticin-containing medium with daily medium exchange for over 21 days. All mock-transfected cultures (i.e., those that received FuGENE™ mixed with water rather than plasmid) died within 48–72 h. Drug resistant colonies arose in the wells transfected with both FuGENE™ and plasmid at a frequency of about 1 in to $10^5$ originally transfected cells. The colonies were maintained in geneticin-containing mEF-conditioned medium and expanded.

Example 11

Alternative Sources of Conditioned Medium for Feeder-free Culture

Conditioned media from several cell lines were tested for their ability to support the growth of hES cells in feeder-free culture. Isolation of primary mouse embryonic fibroblasts (mEF) and the NHG190 telomerized mEF line have already been described. STO is a transformed mouse fibroblast line available from the ATCC. BJ 5ta is a telomerized human foreskin fibroblast cell line. hTERT-RPE is a telomerized human retinal epithelial cell line.

Medium used for growing cells was as follows. 1. mEF medium: 90% DMEM (Gibco BRL, Rockville, Md.), 10% fetal bovine serum (FBS) (heat inactivated) (Hyclone), and 2 mM L-glutamine. 2. STO medium: mEF medium supplemented with 0.1 mM non-essential amino acids. 3. BJ 5ta medium: 90% DMEM and 10% Cosmic calf serum (not heat inactivated). 4. NHG190 medium: mEF medium supplemented with additional 10% FBS. 5. RPE medium: 90% DMEM/F12, 10% FBS (not heat inactivated), 10 ml L-glutamine and 3.48 g/L sodium bicarbonate. 6. Differentiation medium: 80% knockout Dulbecco's modified Eagles medium (KO DMEM), 1 mM L-glutamine, 0.1 mM β-mercaptoethanol and 1% nonessential amino acids, supplemented with 20% FBS.

To prepare conditioned medium, the respective cell lines were harvested by washing once with $Ca^{++}/Mg^{++}$ free PBS, incubating in trypsin/EDTA (Gibco) for about 5 min, and suspending in mEF medium. The cells were irradiated at ~4000 rad (~508 sec at 140 kV: shelf setting 6 in a Torrex generator, EG&G Astrophysics Research Corp., Long Beach Calif.). They were then counted, and seeded at ~55,000 cells/$cm^2$ for mEFs, ~38,000/$cm^2$ for NHG190 cells, ~95,000/$cm^2$ for STO cells, ~80,000/$cm^2$ for BJ 5ta cells, ~90,000/$cm^2$ for RPE cells. After at least 4 h, the medium was exchanged with ES medium containing 4 ng/mL bFGF. Conditioned medium was collected daily thereafter, and used for feeding of hES cultures. Before addition to the hES cultures, each conditioned medium was supplemented with 4 ng/mL of human basic fibroblast growth factor (hbFGF; Gibco).

FIG. 1, Panel B (Right Side) shows morphology of hES cells of the H9 line maintained on Matrigel® in medium conditioned by mEF, NHG190, STO and BJ 5ta cells, compared with unconditioned regular medium (RM). The cells in RPE conditioned medium differentiated within the first week of culture. The cells in the other conditioned mediums all had hES colonies with appropriate ES-morphology. Based on the morphology, confluence of the culture, and the ratio of differentiated to undifferentiated cells the conditioned medium can be ranked in order of decreasing preference as follows: primary mEF, NHG190, STO, and BJ 5ta.

Similar to cells maintained in conditioned medium from primary mEF, cells on Matrigel® or laminin in medium conditioned by other cell lines, including NHG190, STO and BJ 5ta, expressed high levels of SSEA-4, Tra-1-60 and Tra-1-81 but low levels of SSEA-1 as analyzed by FACS analysis (FIG. 2C). Cells on Matrigel® or laminin in mEF conditioned medium or NHG190 conditioned medium were able to differentiate into three germ layer cell types. Immunocytochemical analysis of the differentiated cultures showed positive staining for β-tubulin III consistent with neurons (ectoderm lineage), cardiac troponin I consistent with cardiomyocytes (mesoderm lineage), and α-fetoprotein, consistent with cells of the endoderm lineage.

In Examples 1–3, medium was prepared by adding 4 ng/mL hbFGF to the medium before conditioning with the mEFs, and then again when the conditioned medium was collected and used for feeding of the hES cells. To determine if both additions of hbFGF to the medium are necessary to maintain the ES cells in the undifferentiated state, experiments were performed in which one or both additions of hbFGF were eliminated.

Cultures maintained in conditioned medium without the second addition of hbFGF did not appear healthy at early passages, and appeared differentiated after 29 days in culture. Cells maintained in conditioned medium without the first addition of hbFGF displayed mostly differentiated morphology, but still formed smaller undifferentiated colonies after 27 days in culture. Cells maintained in conditioned medium without either addition of hbFGF completely differentiated after 18 days. In contrast, cells cultured in conditioned medium prepared with both additions of bFGF appeared healthy and undifferentiated in long-term culture. Thus, preparing conditioned medium by adding bFGF both before and after culturing with the feeder cells helps prevent differentiation of hES cells in the subsequent feeder-free culture.

Storage of conditioned medium was tested as follows: Batch medium was prepared by conditioning for 1–2 days in mEF cell cultures as described, and stored at 4° C. in sealed culture flasks. Feeder-free hES cell cultures were maintained with stored medium exchanged daily. Characteristic morphological features of undifferentiated stem cells were still present after at least 7 days, comparable to hES cells maintained in freshly conditioned medium.

To determine if leukemia inhibitory factor (LIF) can substitute for conditioned medium in maintaining hES cells without feeders, cells of the H1 and H9 line were cultured on Matrigel® in ES medium containing LIF at a final concentration of 1500, 1,000, or 500 U/mL (recombinant LIF from R&D systems; Catalog # 250-L). Cells were simultaneously cultured in mEF conditioned medium as the positive control, and unconditioned ES medium as negative control. After one week, cultures in medium either with or without LIF showed a large degree of differentiation, while cultures maintained in mEF conditioned medium contained predominately undifferentiated colonies. These data indicate that LIF will not maintain hES cells in an undifferentiated state in the absence of feeder cells.

Example 12

Medium Conditioned by Human Embryonic Fibroblast-like Cells from the H9 Stem Cell Line Cells were derived from hES cells that have the morphological criteria of fibroblasts and mesenchymal cells. They are capable of supporting hES cells in feeder-free culture.

The H9 hES cell line was obtained as described elsewhere in this disclosure. To form embryoid bodies, the hES cells were harvested after incubation with ~200 U/mL collagenase IV at 37° C. for 10 min, and dissociated into small clusters in differentiation media and cultured in non-adherent cell culture plates (Costar) to form aggregates in suspension. ~2×10$^6$ cells were seeded into each well (9.6 cm$^2$). After 2 days in suspension, the aggregates were transferred into gelatin-coated plates. They attached to the plates and continued to differentiate into cells with different morphologies. Fibroblast-like cells were observed in clusters of 100–1000 cells in the mixed population of the differentiated cells after an additional 11 days.

To isolate the fibroblast-like cells, the culture was incubated in ~200 U/mL collagenase IV for 3 min at 37° C. Clusters of fibroblast-like cells were removed with a Pipetman™ under a microscope and either transferred directly to a tube containing the differentiation media or released into the collagenase solution, and subsequently collected. The cells were spun, resuspended in differentiation media and plated onto one well of a 6-well plate. The cells proliferated, and were serially passaged. The cultures were switched to mEF media in the third passage. In all procedures, cells were fed every 2–3 days.

To introduce telomerase into the fibroblast-like cells, they were infected with retrovirus expressing hTERT as follows. Cells were seeded onto 6-well plates at 8.6×10$^4$ cells/well (9.6 cm$^2$) one day before infection, incubated with virus-containing media supplemented with 4 µg/mL polybrene for 8 h before being changed to mEF medium. Different wells were infected with pBABE-hTERT or a pBABE vector control. pBABE-hTERT was constructed by cloning an hTERT encoding sequence (5'UTR and 3'UTR removed and a Kozak consensus translation initiation site at positions −1 to −5 from the ATG start codon) into the EcoRI site of commercially available pBABE.puro, placing the hTERT encoding region in the same orientation as the 5' LTR (Ouellette et al., Hu. Mol. Gen. 9:403, 2000). The cells were cultured for additional 6 days, and selected in puromycin at a final concentration of 1.6 µg/mL for an additional 8 days. The cells were then harvested and re-seeded in mEF medium.

The cells were expanded and continued to display fibroblast-like morphology for 50 days. Cells were collected for TRAP assay 20 days after the infection. The cells were maintained in mEF medium from day 0 to 27 and were switched to differentiation media from day 28 to day 43. Cells were counted at each passage after the selection and the population doubling was calculated.

Both the telomerized and control cell lines (non-transduced or transduced with control retrovirus) proliferated in culture for ~7 or 8 doublings during 50 days in culture. Cells transduced with the hTERT expression cassette showed positive telomerase activity in the TRAP assay, whereas the control cells did not show any. The hTERT-hEF cells serially passaged with a similar proliferation rate as that of the control cells.

To prepare conditioned medium, the hTERT transfected cells were harvested by washing once with Ca$^{++}$/Mg$^{++}$ free PBS and incubating in 1.5–2 mL trypsin/EDTA (Gibco) for about 2 min. After the cells detached from the plate, they were collected in mEF medium. They were irradiated at 4000 rad, counted and seeded at about 3.7–5×10$^5$ cells/well. After at least 16 h, the medium was exchanged with hES media +4 ng/mL bFGF (serum replacement medium described above, with 4 ng/mL exogenously added human basic fibroblast growth factor). Three to four mL were used per well of a 6 well plate.

Conditioned medium was collected daily for feeding of hES cultures. Before addition to the hES cultures, the conditioned medium was supplemented with 4 ng/mL of hbFGF (Gibco). The hTERT-hEF cultures were used in this system for 1–2 weeks.

The ability of the medium to support hES cell growth was tested on the H1 hES cell line. Cultures of hES cells replated in feeder-free culture on Matrigel® supported by hEF conditioned medium (Panels C & F), formed colonies with morphology characteristic of undifferentiated hES cells. The cultures appeared indistinguishable from hES cells grown directly on a layer of primary mEF feeder cells or on Matrigel® in medium conditioned by primary mEF. Healthy colonies of hES cells increased in size, and had characteristic features of undifferentiated embryonic stem cells. A few colonies showed a degree of differentiation, but the extent of differentiation was similar under each of the culture conditions.

Seven days after the seeding, the cultures had become almost confluent and were split at a 1:3 or 1:4 ratio, ~130,000 to 170,00 cells cm$^{-2}$. Cells were been maintained under this condition for over 30 days while displaying morphology characteristic of hES cells.

Example 13

Medium Conditioned by hEFs From the H1 Line

A second human embryonic fibroblast (hEF) like cell line was developed from a different hES cell line designated H1. Embryoid bodies were formed as before, and after 4 days in suspension culture were plated onto gelatin-coated plates for an additional 9 days.

In this example, fibroblasts were developed from bulk culture rather than being selected out by pipette. The cultures were incubated in 2 mg/mL Collagenase type 11 in PBS for 30 min at 37° C. The cells were harvested, dissociated, centrifuged, resuspended in differentiation medium, and plated in a 6-well plate. The proliferating cells were passaged in hEF medium (90% DMEM, 10% heat-inactivated FBS, 0.1 mM non-essential amino acids, and 2 mM L-glutamine), and fed every 2–3 days. After two passages, the cell population appeared homogeneous with morphological characteristics of fibroblasts. This hEF cell line was designated HEF1.

Subpopulations were transduced with the retrovirus telomerase expression vector (pBABE-hTERT), or with vector control, as in Example 12.

FIG. 11 (Panel A) shows the morphology of the HEF1 cell line. Panel B (below) shows telomerase activity, as measured in the TRAP assay. Cells transduced with the hTERT expression cassette showed positive telomerase activity at 20 or 65 days after transduction. The untransduced cell line, or cells transduced with the vector control showed no telomerase activity.

FIG. 12 shows the growth curves of the hTERT-transduced HEF1 cells, and cells transduced with vector control. Both lines doubled about once every 2 days, until the 38 day point, when the control cells stopped dividing (presumably because they had reached the Hayflick limit). The hTERT-transfected cells continued proliferating beyond the 60 day point (30 doublings) at a consistent growth rate.

FIG. 13 is a micrograph of the hTERT transduced cells and control cells, after staining for senescence-associated β-galactosidase, a known biomarker for cellular aging (Dimitri et al., Proc. Natl. Acad. Sci. USA 92:9363, 1995). Cells grown on chamber slides were fixed 2 min in 0.2% glutaraldehyde in PBS, washed with PBS, and incubated overnight in 1 mg/mL 5-bromo-4-chloro-3-indolyl-D-galactosidase (X-gal), 5 mM $K_4Fe(CN)_6$, 5 mM $K_3Fe(CN)_6$, 150 mM NaCl, 2 mL $MgCl_2$, in 40 mM citric acid phosphate buffer pH 6.0. The HEF1 control cells stained heavily for β-galactosidase, whereas the hTERT transduced sells did not. The combined results indicate that the expression of hTERT extends the life-span characteristics of the HEF1 cells.

Medium was conditioned as in Example 12, using HEF1 cells irradiated at 6000 rad, and seeded at ~4.1 to 5.5×10$^4$ cells cm$^{-2}$. The medium was tested for its ability to support growth of the H9 hES cell line cultured on a Matrigel® substrate.

FIG. 14 shows colonies of hES cells after passaging into medium conditioned either by mouse embryonic fibroblasts, or by the HEF1 cell line. The hES cells have been maintained using the HEF1 conditioned medium for 4 passages, continuing to display the morphology of undifferentiated ES cells. The hES cells were found to maintain expression of hTERT and OCT-4. As shown in Panel B, they also continued to demonstrate telomerase activity, as measured in the TRAP assay, which is characteristic of undifferentiated hES cells.

Example 14 cDNA Libraries

Poly A+ mRNA was isolated from undifferentiated and differentiated pPS cells as follows.

Human embryonic stem cells were obtained either from cultures grown on feeder cells, or in a feeder-free environment, as described elsewhere in this disclosure. cDNA libraries have been obtained from both. Using feeder-free cultures has the advantage of producing libraries that are free of contaminating mouse RNA, and can be more easily scaled to produce large numbers of cells for mRNA isolation.

Total RNA was isolated from hES cells using the RNeasy™ protocol and reagents (Qiagen, Germany) according to manufacturers directions. Briefly, cells were lysed directly in the culture dish using a solution of guanidinium isothiocyanate (GITC) and the resulting extract was bound to the RNeasy™ matrix under conditions in which RNA is bound, but contaminants and genomic DNA are not. After washing the matrix with the prescribed buffers supplied by the manufacturer, the total RNA was eluted with water and quantified by absorbance at 260 nm.

Poly A+ mRNA was then purified from the total RNA preparation by using the Oligotex™ protocol and reagents (Qiagen, Germany). Briefly, bead matrices containing covalently bound $dC_{10}T_{30}$ oligonucleotides were mixed with total RNA, allowing interaction between the polyA+ tails of mRNAs with the $dC_{10}T_{30}$-bound beads. After washing with specified wash solutions, the bound mRNA was released in a low salt buffer, and the yield was quantified by absorbance at 260 nm. Gel electrophoresis confirmed the overall purity of the poly A+ mRNA. cDNA synthesis was accomplished using a standard protocol (SuperScript™ Lambda System, Life Technologies, Rockville, Md.). One μg of poly A+ mRNA was converted to single-stranded cDNA using an oligo dT-NotI primer/adaptor and SuperScript™ II reverse transcriptase. [$^{32}$P]dCTP was included in the reaction to allow for the calculation of the first strand conversion efficiency. The single stranded cDNA was then converted into double stranded cDNA using DNA polymerase in the presence of DNA ligase and RNaseH (all enzymes of *E. coli* origin). The double-stranded cDNA was ligated with SalI adaptors and then resolved by gel exclusion chromatography. A portion of each column fraction was analyzed by gel electrophoresis, and fractions containing cDNA with a predicted median size of 2 kbp or larger were pooled. The size-selected cDNA pool was then restricted with NotI endonuclease, and ligated with NotI/SalI-restricted pSport1 plasmid (Life Technologies). The ligation products were used to transform UltraMax™ competent *E. coli* (Life Technologies), which were subsequently plated onto medium plates containing ampicillin. Libraries produced by these methods typically consisted of 5×10$^6$ or more independent clones with a median cDNA insert size of ~1.2 kbp, as judged by PCR of plasmid preparations from individual colonies.

cDNA libraries have also been prepared from embryoid body (EB) cells, which comprise a mixed population of cells differentiated from hES cells. To prepare EBs, monolayer cultures of hES cells were harvested by incubating with ~200 U/mL collagenase IV for ~5–20 min at 37° C. The hES cells were dissociated into clusters and plated in non-adherent cell culture plates (Costar) in Differentiation Medium, composed of 80% KO DMEM (Gibco), 20% non-heat-inactivated FBS (Hyclone), 0.1 mM non-essential amino acids, 1 mM glutamine, and 0.1 mM β-mercaptoethanol.

The EB were then seeded at a 1:2 ratio in 2 mL medium per 9.6 cm$^2$ well. The EBs were fed every other day by adding 2 mL of medium per well up to 4 mL/well, and then collecting and resuspending in 2 mL fresh medium. Total RNA was prepared after ~2–8 days in suspension culture. Alternatively, EBs were maintained in suspension culture for ~4 days, and then plated onto gelatin coated plates and cultured for a further 7 days. This results in formation of a diverse cell population, and improves the yield of RNA, probably because of higher cell density. Yield of total RNA from ~20 to 500×10$^6$ cells was ~25 to 2500 μg.

Selection of Promoters for Expression in hES Cells

A variety of promoters was tested for their ability to drive stable long-term gene expression in undifferentiated hES cells. Constructs were introduced either by retroviral transduction, or by FuGENE™ mediated lipofection.

hES cells plated in 6 well plates were removed from the feeder layer with collagenase (~200 units/mL) at 370 for 7–10 min. When colonies began to detach, the collagenase from each well was aspirated and replaced with 2 mL of standard hES medium/well. The hES cells were removed by scraping the surface of a single well with a 5 mL pipet and transferred to a 50 mL conical tube. Additional hES medium was added to a final volume of 10 mL. The cell suspension was triturated 10–12 times with a 10 mL pipet, and an additional 8 mL of standard hES medium added. Three mL of the cell suspension were added to each well of 6 well plates that were pre-coated with gelatin and mEF feeder layers as described above (i.e., 1 well of a 6 well plate was sufficient to seed 6 wells of a new plate).

Transduction using retrovirus was conducted as follows. Retroviral vector designated GRN354 was constructed at Geron Corp. using PMSCVneo vector purchased from ClonTech (cat # K1062-1). The eGFP encoding region was inserted downstream from the MSCV LTR. The LTR drives expression of GFP, and the vector also contains the neo gene driven by the murine PGK promoter.

Plates were coated with 0.5% gelatin and NHG190 feeder cells (7.5×10$^4$ in 1 mL NHG190 medium for 24 well plates; 3.75×10$^5$ in 3 mL medium for 6 well plates). The hES line H7 was seeded onto a 24 well prepared plate in hES medium (1 mL/well). Forty-eight h later, 3 wells of hES cells were detached using 0.05% trypsin/5 mM EDTA (Sigma) at 37° C., resuspended in 500 μL NHG190 medium, and counted. Stock of retrovirus construct pGRN354 was thawed on ice immediately prior to use. Growth medium was aspirated from the wells and replaced with 400 μL hES medium plus 8 μL retrovirus (MOI of 10) and 4 μL of 8 mg/mL polybrene solution (Sigma). Two h later, 800 μL hES medium were added per well. Each transduced well was refed with 1 mL fresh hES medium every 24 h.

Four days after transduction, medium was replaced with 1 mL hES medium containing 200 μg/mL geneticin. After 3 days of geneticin selection, the cells were detached with collagenase, triturated, resuspended in 3 mL hES medium, reseeded into one well of a 6-well plate coated with gelatin and NHG190 feeders, and refed with hES medium after 24 h. The medium was then again replaced with hES medium containing geneticin and refed every 24 h.

Lipofection using FuGENE™ 6 (Roche) was conducted according to manufacturers directions. The plasmid DNA (5–10 μg of pEGFP-C1, ClonTech cat. #6084-1) was diluted in water to a final volume of 100 μl. In pilot experiments, 5–30 μL of FuGENE™ were added to sufficient Opti-MEM™ solution (Gibco, cat # 11-58-021) to achieve a final volume of 100 μL. The DNA solution was then added slowly to the FuGENE™ solution and mixed gently. The mixture was incubated at room temperature for 30 min before being supplemented with 800 μl of OptiMEM™.

Forty-eight hours before transfection, hES cells were seeded onto 6 well plates that had been coated with gelatin and mEF feeder layers. Cells were washed with 3 mL of pre-warmed OptiMEM™ and incubated in DNA/lipid mixture solution at 37° C. for 4 h. In some experiments, after 4 h the wells received an additional 2 mL of mEF-conditioned medium; in others the DNA/lipid mixture was added to wells containing 2 mL of mEF-conditioned medium and the cells were incubated in this mixture overnight.

In subsequent experiments, feeder-free cultures of hES cells were transfected using FuGENE™. In these experiments, undifferentiated hES cells were seeded onto Matrigel®-coated 6-well plates (at a typical density of ~1.5×10$^4$ cells cm$^{-2}$) in mEF conditioned medium plus an additional 4 ng/mL hbFGF. Forty-eight h after plating, the cells were transfected with FuGENE™ as already described. Forty-eight h after transfection, cells were re-fed with mEF conditioned medium plus 4 ng/mL hbFGF and 200 μG/mL geneticin. Subsequently, the cells were re-fed with medium containing 200 μG/mL geneticin on a daily basis.

Results of representative experiments are summarized in Table 2.

TABLE 2

Testing of Promoters for Expression in human Embryonic Stem Cells

| Method | Constructs (promoter/ORF combination) | Number of Undifferentiated Lines Derived | Result |
|---|---|---|---|
| Retrovirus Transduction | MSCV-LTR/GFP; PGK/neo (single vector) | mixed culture | 100% G418 resistant 50–65% GFP positive |

TABLE 2-continued

Testing of Promoters for Expression in human Embryonic Stem Cells

| Method | Constructs (promoter/ORF combination) | Number of Undifferentiated Lines Derived | Result |
|---|---|---|---|
| Lipofection | CMV/β-galactosidase; SV/neo (single vector) | 3 | 100% G418 resistant β-galactosidase negative |
| Lipofection | CMV/GFP; PGK/neo (2 vectors cotransfected) | 5–6 pooled colonies | 100% G418 resistant GFP negative |
| Lipofection | UbiC*/β-galactosidase; PGK/neo (2 vectors cotransfected) | 1 | 100% G418 resistant β-galactosidase negative |
| Lipofection | EF1α/β-galactosidase; PGK/neo (2 vectors cotransfected) | 13 individual lines, 4–5 pooled colonies | 100% G418 resistant GFP negative |
| Lipofection | MSCV LTR/neo; PGK/hTERT (single vector) | 0 | 100% G418 resistant differentiated cells only |
| Lipofection | EF1α/neo | 16 | 100% G418 resistant |
| Lipofection | UbiC*/neo | 3 | 100% G418 resistant |

By these criteria, the PGK, EF1α, and UbiC promoters are appropriate for stable long-term expression of cDNA clones in undifferentiated hES cells.

It will be recognized that the compositions and procedures provided in the description can be effectively modified by those skilled in the art without departing from the spirit of the invention embodied in the claims that follow.

What is claimed is:

1. A method of screening a substance, comprising:
   a) obtaining a composition comprising undifferentiated pPS cells proliferating on an extracellular matrix instead of feeder cells, but in a medium conditioned by fibroblast feeder cells;
   b) optionally causing or permitting the pPS cells to differentiate; then
   c) combining the cells with the substance; and
   d) determining any effect of the substance on the cells.

2. The method of claim 1, wherein the extracellular matrix upon which the undifferentiated pPS cells are cultured is Matrigel® basement membrane matrix, laminin, or collagen.

3. The method of claim 1, wherein the cells are undifferantiated when contacted with the substance.

4. The method of claim 1, wherein the cells have been caused or permitted to differentiate before being contacted with the substance.

5. The method of claim 4, wherein the cells have been caused to differentiate by a process comprising replating them onto a surface that promotes differentiation.

6. The method of claim 4, wherein the cells have been caused to differentiate by adding component(s) to the medium that promote differentiation towards a particular cell lineage.

7. The method of claim 4, comprising causing the cells to differentiate into cells having characteristics of neuronal cells, glial cells, or neural precursors.

8. The method of claim 4, comprising causing the cells to differentiate into cells having characteristics of hepatocytes.

9. The method of claim 1, wherein the pPS cells are human embryonic stem (hES) cells.

10. The method of claim 1, comprising determining the effect of the substance on growth of the cells.

11. The method of claim 1, comprising determining whether the substance affects differentiation of the cells.

12. The method of claim 1, comprising determining whether the substance affects expression of a marker or receptor by the cells.

13. The method of claim 1, comprising determining whether the substance affects release of a mwter or enzyme from the cells.

14. The method of claim 1, comprising determining whether the substance affects DNA synthesis or repair in the cells.

15. The method of claim 1, comprising analyzing the cells by metaphase spread.

16. The method of claim 1, comprising determining whether the substance is toxic to the cells.

17. A method of screening a substance for its effect on undifferentiated human embryonic stem (hES) cells, comprising:
   a) obtaining a composition comprising undifferentiated pPS cells proliferating on an extracellular matrix instead of feeder cells, but in a medium conditioned by fibroblast feeder cells;
   b) combining the undifferentiated hES cells with the substance; and
   c) determining any effect of the substance on the cells.

18. The method of claim 17, comprising determining the effect of the substance on growth of the cells.

19. The method of claim 17, comprising determining whether the substance affects differentiation of the cells.

20. The method of claim 17, comprising determining whether the substance affects expression of a marker or receptor by the cells.

21. The method of claim 17, comprising determining whether the substance is toxic to the cells.

22. A method of screening a substance, comprising:
a) obtaining a composition comprising undifferentiated hES cells proliferating on an extracellular matrix instead of feeder cells, in a medium conditioned by fibroblast feeder cells;
b) differentiating said hES cells;
c) contacting the population of differentiated cells with the substance;
d) determining any phenotypic or metabolic change in the cell that results from contact with the substance, and
e) correlating the change with cellular toxicity or modulation.

23. The method of claim 22, comprising causing the cells to differentiate into cells having characteristics of neuronal cells, glial cells, or neural precursors.

24. The method of claim 22, comprising causing the cells to differentiate into cells having characteristics of hepatocytes.

25. The method of claim 22, comprising determining the effect of the substance on growth of the cells.

26. The method of claim 22, comprising determining whether the compound affects expression of a marker or receptor by the cells.

27. The method of claim 22, comprising determining whether the compound is toxic to the cells.

* * * * *